(12) United States Patent
Heil et al.

(10) Patent No.: US 10,501,441 B2
(45) Date of Patent: Dec. 10, 2019

(54) SUBSTITUTED IMIDAZOLYLCARBOXAMIDES AS PESTICIDES

(71) Applicant: BAYER CROPSCIENCE AKTIENGESELLSCHAFT, Monheim am Rhein (DE)

(72) Inventors: Markus Heil, Leichlingen (DE); Reiner Fischer, Monheim (DE); Johannes-Rudolf Jansen, Monheim (DE); David Wilcke, Düsseldorf (DE); Matthieu Willot, Düsseldorf (DE); Susanne Kübbeler, Düsseldorf (DE); Kerstin Ilg, Köln (DE); Sascha Eilmus, Leichlingen (DE); Peter Lösel, Leverkusen (DE); Wolfram Andersch, Bergisch Gladbach (DE); Ulrich Görgens, Ratingen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 16/076,797

(22) PCT Filed: Feb. 6, 2017

(86) PCT No.: PCT/EP2017/052497
§ 371 (c)(1),
(2) Date: Aug. 9, 2018

(87) PCT Pub. No.: WO2017/137337
PCT Pub. Date: Aug. 17, 2017

(65) Prior Publication Data
US 2019/0047987 A1   Feb. 14, 2019

(30) Foreign Application Priority Data

Feb. 11, 2016   (EP) .................................. 16155136

(51) Int. Cl.
| | | |
|---|---|---|
| *C07D 401/14* | (2006.01) |
| *C07D 403/14* | (2006.01) |
| *A01N 43/50* | (2006.01) |
| *A01N 43/56* | (2006.01) |
| *A01N 43/653* | (2006.01) |
| *A01N 43/84* | (2006.01) |
| *C07D 401/12* | (2006.01) |

(52) U.S. Cl.
CPC .......... *C07D 401/14* (2013.01); *A01N 43/50* (2013.01); *A01N 43/56* (2013.01); *A01N 43/653* (2013.01); *A01N 43/84* (2013.01); *C07D 401/12* (2013.01); *C07D 403/14* (2013.01)

(58) Field of Classification Search
CPC ...... A61K 43/50; A61K 43/56; A61K 43/653; A61K 43/84; C07D 401/12; C07D 401/14; C07D 403/14
See application file for complete search history.

(56) References Cited

FOREIGN PATENT DOCUMENTS

| WO | 02/070483 A1 | 9/2002 | |
| WO | WO-2005051949 A1 * | 6/2005 | ........... C07D 471/04 |
| WO | 2011/009804 A2 | 1/2011 | |
| WO | WO-2016128298 A1 * | 8/2016 | ............. A01N 43/52 |

OTHER PUBLICATIONS

International Search Report of International Patent Application No. PCT/EP2017/052497 dated Mar. 20, 2017.

* cited by examiner

*Primary Examiner* — Joseph R Kosack
(74) *Attorney, Agent, or Firm* — McBee Moore Woodward & Vanik IP, LLC

(57) ABSTRACT

The present invention relates to compounds of the general formula (I)

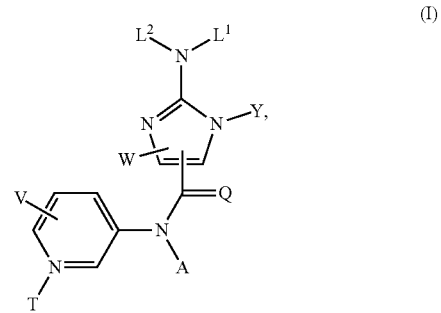

in which Q, V, T, W, Y, $L^1$, $L^2$ and A have the meanings given in the description—and to their use for controlling animal pests.

14 Claims, No Drawings

SUBSTITUTED IMIDAZOLYLCARBOXAMIDES AS PESTICIDES

CROSS-REFERENCE TO RELATED APPLICATIONS

This application is a National Stage entry of International Application No. PCT/EP2017/052497, filed 6 Feb. 2017, which claims priority to European Patent Application No. 16155136.1, filed 11 Feb. 2016.

BACKGROUND

Field

The present application relates to novel heterocyclic compounds, processes and intermediates for their preparation and their use for controlling animal pests.

Description of Related Art

WO 2011/009804 A2 describes heterocyclic compounds including, inter alia, imidazolylcarboxamides which can be used as insecticides. However, imidazolylcarboxamides which are substituted directly at the imidazolyl ring by amino groups are not described. The imidazolylcarboxamides listed in WO 2011/009804 A2 have considerable weaknesses in their insecticidal action.

Modern insecticides have to meet many demands, for example in relation to extent, persistence and spectrum of their action and possible use. Questions of toxicity, sparing of beneficial species and pollinators, environmental properties, application rates, combinability with other active ingredients or formulation auxiliaries play a role, as does the question of the effort required for the synthesis of an active ingredient; furthermore, resistances may occur, to mention only some parameters. For all these reasons alone, the search for novel crop protection compositions cannot be considered complete, and there is a constant need for novel compounds having improved properties compared to the known compounds, at least in relation to individual aspects.

SUMMARY

It was an object of the present invention to provide compounds which widen the spectrum of the pesticides in various aspects.

This object, and further objects which are not stated explicitly which can be discerned or derived from the connections discussed herein, are achieved by the provision of compounds of the formula (I)

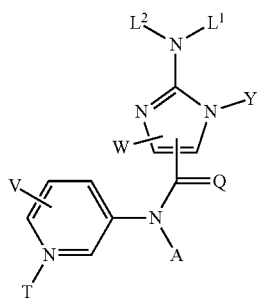

(I)

in which (embodiment (0))
Q represents oxygen or sulphur,
V represents a radical from the group consisting of hydrogen, halogen, alkyl, haloalkyl, alkoxy, haloalkoxy and cyano,
W represents a radical from the group consisting of hydrogen, halogen, alkyl, haloalkyl, alkoxy, haloalkoxy and cyano,
Y represents a radical from the group consisting of hydrogen, cyano, optionally substituted alkyl, alkenyl or alkynyl, optionally substituted cycloalkyl which is optionally interrupted by heteroatoms, optionally substituted cycloalkylalkyl which is optionally interrupted by heteroatoms, arylalkyl or hetarylalkyl,
A represents a radical from the group consisting of hydrogen, optionally substituted alkyl, alkenyl or alkynyl and optionally substituted cycloalkyl or cycloalkylalkyl which are optionally interrupted by heteroatoms,
T represents oxygen or an electron pair,
$L^1$ represents a radical from the group consisting of hydrogen, optionally substituted alkyl, alkenyl, alkynyl or cycloalkyl and represents the radicals $C(O)R^2$, $C(O)N(R^3)(R^4)$, $C(O)OR^5$ and $SO_2R^6$,
$L^2$ represents a radical from the group consisting of hydrogen, $N(R^{3a})(R^{4a})$, optionally substituted alkyl, alkenyl, alkynyl or alkoxy, optionally substituted cycloalkyl or cycloalkylalkyl which is optionally interrupted by heteroatoms, and optionally substituted aryl, arylalkyl, hetaryl or hetarylalkyl, or
$L^1$ and $L^2$ represent, together with the nitrogen atom to which they are attached, an optionally substituted saturated, partially saturated or aromatic heterocycle having 3 to 7 ring atoms which can optionally be interrupted by further heteroatoms and/or by one or two C=O groups,
$R^2$ represents a radical from the group consisting of hydrogen, optionally substituted alkyl, alkenyl or alkynyl, optionally substituted cycloalkyl, optionally substituted aryl or hetaryl and optionally substituted arylalkyl or hetarylalkyl,
$R^3$ and $R^4$ each independently of one another represent a radical from the group consisting of hydrogen, optionally substituted alkyl, alkenyl or alkynyl, optionally substituted saturated or unsaturated cycloalkyl, cycloalkylalkyl, aryl, hetaryl, arylalkyl or hetarylalkyl, or
$R^3$ and $R^4$ together form an optionally substituted three- to seven-membered aliphatic ring which optionally contains a nitrogen, sulphur or oxygen atom,
$R^{3a}$ represents a radical from the group consisting of hydrogen, optionally substituted alkyl, optionally substituted cycloalkyl, aryl, hetaryl, arylalkyl or hetarylalkyl,
$R^{4a}$ represents a radical from the group consisting of hydrogen, optionally substituted alkyl, optionally substituted $C_3$-$C_6$-cycloalkyl and represents the radicals $C(O)R^2$, $C(O)OR^5$ and $SO_2R^6$,
$R^5$ represents optionally substituted alkyl, alkenyl or alkynyl, optionally substituted cycloalkyl or cycloalkylalkyl,
$R^6$ represents a radical from the group consisting of optionally substituted alkyl, alkenyl or alkynyl, optionally substituted cycloalkyl, cycloalkylalkyl, aryl, arylalkyl, hetaryl or hetarylalkyl
and salts thereof.

DETAILED DESCRIPTION OF A PREFERRED EMBODIMENT

Preferred substituents or ranges for the radicals listed in the compounds of the formula (I) are illustrated below. The combination thereof forms the range of preference (1-1).
Q represents oxygen or sulphur, V represents a radical from the group consisting of hydrogen, halogen, $C_1$-$C_4$-alkyl, $C_1$-$C_4$-haloalkyl, $C_1$-$C_4$-alkoxy, $C_1$-$C_4$-haloalkoxy and cyano, W represents a radical from the group consisting of hydrogen, halogen, $C_1$-$C_4$-alkyl, $C_1$-$C_4$-haloalkyl, $C_1$-$C_4$-alkoxy, $C_1$-$C_4$-haloalkoxy and cyano, Y represents a radical from the group consisting of hydrogen, $C_1$-$C_6$-alkyl, $C_3$-$C_6$-alkenyl or $C_3$-$C_6$-alkynyl, optionally mono- to polysubstituted independently of one another by halogen, $C_1$-$C_4$-alkoxy, $C_1$-$C_4$-alkyl-S(O)$_n$— or cyano, $C_3$-$C_8$-cycloalkyl, optionally mono- to disubstituted independently of one another by halogen, $C_1$-$C_4$-alkyl, $C_1$-$C_4$-haloalkyl, $C_1$-$C_4$-alkoxy or cyano, straight-chain or branched $C_3$-$C_8$-cycloalkyl-$C_1$-$C_4$-alkyl, optionally interrupted once or twice independently of one another by O, S(O)$_n$, CO or NR$^{4a}$ and optionally mono- to tetrasubstituted independently of one another by halogen, $C_1$-$C_4$-alkyl, $C_1$-$C_4$-haloalkyl, $C_1$-$C_4$-alkoxy or cyano, aryl-$C_1$-$C_4$-alkyl or hetaryl-$C_1$-$C_4$-alkyl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, nitro or cyano, A represents a radical from the group consisting of hydrogen, $C_1$-$C_6$-alkyl, $C_3$-$C_6$-alkenyl or $C_3$-$C_6$-alkynyl, optionally mono- to polysubstituted independently of one another by halogen, $C_1$-$C_4$-alkoxy, $C_1$-$C_4$-alkyl-S(O)$_n$— or cyano and $C_3$-$C_6$-cycloalkyl or $C_3$-$C_8$-cycloalkyl-$C_1$-$C_4$-alkyl, optionally mono- to disubstituted independently of one another by halogen, $C_1$-$C_4$-alkyl, $C_1$-$C_4$-haloalkyl, $C_1$-$C_4$-alkoxy or cyano and $C_1$-$C_6$-alkyl, $C_3$-$C_6$-alkenyl or $C_3$-$C_6$-alkynyl, optionally mono- to polysubstituted independently of one another by halogen, $C_1$-$C_4$-alkoxy, $C_1$-$C_4$-alkyl-S(O)$_n$— or cyano, and straight-chain or branched $C_3$-$C_8$-cycloalkyl-$C_1$-$C_4$-alkyl, optionally mono- to disubstituted independently of one another by halogen, $C_1$-$C_4$-alkyl, $C_1$-$C_4$-haloalkyl, $C_1$-$C_4$-alkoxy or cyano, T represents oxygen or an electron pair, $L^1$ represents a radical from the group consisting of hydrogen, $C_1$-$C_4$-alkyl, $C_3$-$C_6$-alkenyl or $C_3$-$C_6$-alkynyl, optionally mono- to trisubstituted independently of one another by halogen, $C_1$-$C_4$-alkoxy, $C_1$-$C_4$-alkyl-S(O)$_n$— or cyano, $C_3$-$C_6$-cycloalkyl, optionally mono- to disubstituted independently of one another by halogen, $C_1$-$C_4$-alkyl, $C_1$-$C_4$-haloalkyl, $C_1$-$C_4$-alkoxy or cyano and represents the radicals C(O)R$^2$, C(O)N(R$^3$)(R$^4$), C(O)OR$^5$ and SO$_2$R$^6$, $L^2$ represents a radical from the group consisting of hydrogen, —N(R$^{3a}$)(R$^{4a}$), $C_1$-$C_4$-alkyl, $C_3$-$C_6$-alkenyl, $C_3$-$C_6$-alkynyl or $C_1$-$C_4$-alkoxy, optionally mono- to trisubstituted independently of one another by halogen, $C_1$-$C_4$-alkoxy, $C_1$-$C_4$-alkyl-S(O)$_n$— or cyano, straight-chain or branched $C_3$-$C_8$-cycloalkyl or $C_3$-$C_8$-cycloalkyl-$C_1$-$C_4$-alkyl, optionally interrupted once or twice independently of one another by O, S(O)$_n$, CO or NR$^{4a}$ and optionally mono- to tetrasubstituted independently of one another by halogen, $C_1$-$C_4$-alkyl, $C_1$-$C_4$-haloalkyl, $C_1$-$C_4$-alkoxy or cyano, aryl, hetaryl, arylalkyl or hetarylalkyl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, nitro or cyano, or $L^1$ and $L^2$ together with N represent a heterocycle from the group U-1 to U-36,

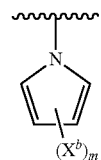 U-1

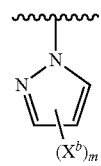 U-2

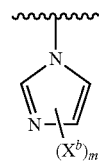 U-3

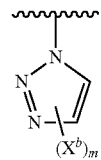 U-4

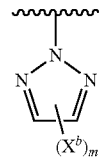 U-5

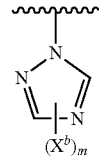 U-6

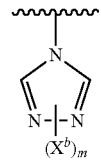 U-7

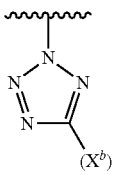 U-8

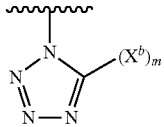 U-9

-continued
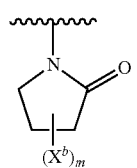 U-10
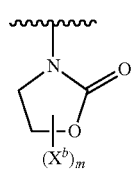 U-11
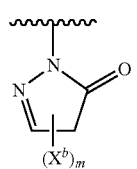 U-12
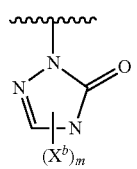 U-13
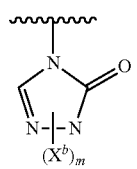 U-14
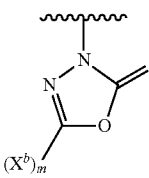 U-15
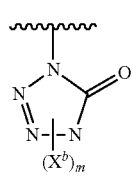 U-16
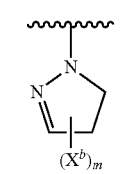 U-17
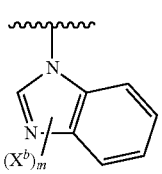 U-18
-continued
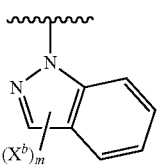 U-19
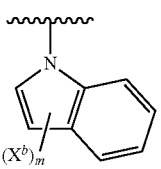 U-20
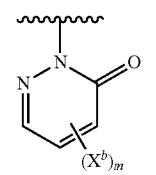 U-21
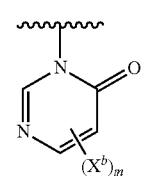 U-22
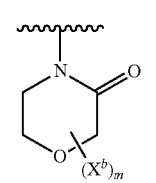 U-23
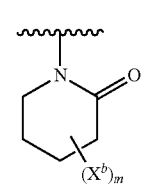 U-24
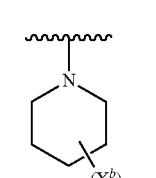 U-25
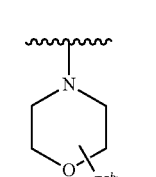 U-26
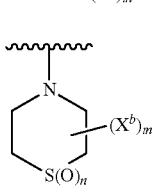 U-27

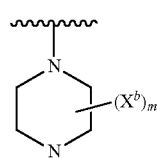

$X^b$ represents a radical from the group consisting of halogen, nitro, cyano, $C_1$-$C_4$-alkyl, $C_3$-$C_6$-cycloalkyl, $C_1$-$C_5$-halogenalkyl, $C_1$-$C_4$-alkoxy, $C_1$-$C_4$-haloalkoxy, $C_3$-$C_6$-halocycloalkyl, $C_1$-$C_4$-alkoxy-$C_1$-$C_4$-alkyl, cyano-$C_1$-$C_4$-alkyl, $C_3$-$C_6$-cycloalkyl-$C_1$-$C_4$-alkyl, $C_2$-$C_6$-alkenyl, $C_3$-$C_6$-alkynyl, $C_1$-$C_4$-alkyl-S(O)$_n$—, $C_1$-$C_4$-alkylcarbonyl, $C_1$-$C_6$-haloalkylcarbonyl, $C_1$-$C_6$-alkoxycarbonyl, $C_1$-$C_6$-alkylaminocarbonyl, di-($C_1$-$C_6$)alkylaminocarbonyl, $C_1$-$C_6$-alkyl-carbonylamino, aryl and hetaryl, where the substituents aryl and hetaryl may optionally be mono- or polysubstituted by identical or different substituents from the group consisting of halogen, cyano, nitro, $C_1$-$C_6$-alkyl, $C_2$-$C_6$-alkenyl, $C_2$-$C_6$-alkynyl, $C_1$-$C_4$-alkoxy, $C_1$-$C_4$-haloalkyl, $C_1$-$C_6$-haloalkoxy and $C_1$-$C_4$-alkylthio and where the ring nitrogen atoms in U-13, U-14, U-16, U-28 and U-35 are not substituted by halogen, nitro, cyano, $C_1$-$C_4$-alkoxy, $C_1$-$C_4$-haloalkoxy, $C_1$-$C_4$-alkoxy-$C_1$-$C_4$-alkyloxy, $R^2$ represents a radical from the group consisting of hydrogen, $C_1$-$C_8$-alkyl, $C_3$-$C_8$-alkenyl or $C_3$-$C_8$-alkynyl, optionally mono- to polysubstituted independently of one another by halogen, $C_1$-$C_4$-alkoxy or $C_1$-$C_4$-alkyl-S(O)$_n$—, $C_3$-$C_8$-cycloalkyl, optionally mono- to disubstituted independently of one another by halogen, $C_1$-$C_4$-alkyl, $C_1$-$C_4$-haloalkyl, $C_1$-$C_4$-alkoxy or cyano, aryl or hetaryl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, nitro or cyano and straight-chain or branched aryl-$C_1$-$C_4$-alkyl or hetaryl-$C_1$-$C_4$-alkyl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, nitro or cyano, $R^3$, $R^4$ independently of one another represent a radical from the group consisting of hydrogen, $C_1$-$C_8$-alkyl, $C_3$-$C_8$-alkenyl or $C_3$-$C_8$-alkynyl, optionally mono- to polysubstituted independently of one another by halogen, $C_1$-$C_4$-alkoxy or $C_1$-$C_4$-alkyl-S(O)$_n$—, $C_3$-$C_8$-cycloalkyl, optionally mono- to disubstituted independently of one another by halogen, $C_1$-$C_4$-alkyl, $C_1$-$C_4$-haloalkyl, $C_1$-$C_4$-alkoxy or cyano, aryl or hetaryl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, nitro or cyano and straight-chain or branched aryl-$C_1$-$C_4$-alkyl or hetaryl-$C_1$-$C_4$-alkyl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, nitro or cyano, $R^{3a}$ represents a radical from the group consisting of hydrogen, $C_1$-$C_8$-alkyl, optionally mono- to polysubstituted independently of one another by halogen, cyano or $C_1$-$C_4$-alkoxy, $C_3$-$C_8$-cycloalkyl, optionally mono- to disubstituted independently of one another by halogen, $C_1$-$C_4$-alkyl, $C_1$-$C_4$-haloalkyl or $C_1$-$C_4$-alkoxy, aryl or hetaryl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, nitro or cyano and straight-chain or branched aryl-$C_1$-$C_4$-alkyl or hetaryl-$C_1$-$C_4$-alkyl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)—, $C_1$-$C_4$-haloalkoxy, nitro or cyano, $R^{4a}$ represents a radical from the group consisting of hydrogen, $C_1$-$C_4$-alkyl, optionally mono- to polysubstituted independently of one another by halogen or $C_1$-$C_4$-alkoxy, $C_3$-$C_6$-cycloalkyl, optionally mono- to disubstituted independently of one another by halogen, $C_1$-$C_4$- alkyl, $C_1$-$C_4$-haloalkyl or $C_1$-$C_4$-alkoxy and represents the radicals $C(O)R^2$, $C(O)OR^5$ and $SO_2R^6$, $R^5$ represents $C_1$-$C_8$-alkyl, $C_3$-$C_8$-alkenyl or $C_3$-$C_8$-alkynyl, optionally mono- to polysubstituted independently of one another by halogen, $C_1$-$C_4$-alkoxy or $C_1$-$C_4$-alkyl-$S(O)_n$—, $C_3$-$C_8$-cycloalkyl, optionally mono- to disubstituted independently of one another by halogen, $C_1$-$C_4$-alkyl, $C_1$-$C_4$-haloalkyl, $C_1$-$C_4$-alkoxy or cyano, $R^6$ represents a radical from the group consisting of $C_1$-$C_8$-alkyl, $C_3$-$C_8$-alkenyl or $C_3$-$C_8$-alkynyl, optionally mono- to polysubstituted independently of one another by halogen, $C_1$-$C_4$-alkoxy or $C_1$-$C_4$-alkyl-$S(O)_n$—, $C_3$-$C_8$-cycloalkyl, optionally mono- to disubstituted independently of one another by halogen, $C_1$-$C_4$-alkyl, $C_1$-$C_4$-haloalkyl, $C_1$-$C_4$-alkoxy or cyano, aryl or hetaryl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-$S(O)_n$—, $C_1$-$C_4$-haloalkoxy, $C_1$-$C_4$-haloalkyl-$S(O)_n$—, nitro or cyano, m represents a number 0, 1, 2 or 3, n represents a number 0, 1 or 2, and salts thereof.

Further preferred substituents or ranges for the radicals listed in the compounds of the formula (I) are illustrated below. The combination thereof forms the range of preference (1-2), where Q, V, W, Y, A, T, $L^1$, $L^2$, $R^2$, $R^3$, $R^4$, $R^{3a}$, $R^{4a}$, $R^5$, $R^6$, m and n are as defined in the range of preference (1-1) and $X^b$ represents a radical from the group consisting of halogen, nitro, cyano, amino, $C_1$-$C_4$-alkyl, $C_3$-$C_6$-cycloalkyl, $C_1$-$C_5$-haloalkyl, $C_1$-$C_4$-alkoxy, $C_1$-$C_4$-haloalkoxy, $C_3$-$C_6$-halocycloalkyl, $C_1$-$C_4$-alkoxy-$C_1$-$C_4$-alkyl, cyano-$C_1$-$C_4$-alkyl, $C_3$-$C_6$-cycloalkyl-$C_1$-$C_4$-alkyl, $C_2$-$C_6$-alkenyl, $C_3$-$C_6$-alkynyl, $C_1$-$C_4$-alkyl-$S(O)_n$—, $C_1$-$C_4$-alkylcarbonyl, $C_1$-$C_6$-haloalkylcarbonyl, $C_1$-$C_6$-alkoxycarbonyl, $C_1$-$C_6$-alkylaminocarbonyl, di-($C_1$-$C_6$)alkylaminocarbonyl, $C_1$-$C_6$-alkylcarbonylamino, aryl and hetaryl, where the substituents aryl and hetaryl may optionally be mono- or polysubstituted by identical or different substituents from the group consisting of halogen, cyano, nitro, $C_1$-$C_6$-alkyl, $C_2$-$C_6$-alkenyl, $C_2$-$C_6$-alkynyl, $C_1$-$C_4$-alkoxy, $C_1$-$C_4$-haloalkyl, $C_1$-$C_6$-haloalkoxy and $C_1$-$C_4$-alkylthio and where the ring nitrogen atoms in U-13, U-14, U-16 and U-28 are not substituted by halogen, nitro, cyano, $C_1$-$C_4$-alkoxy, $C_1$-$C_4$-haloalkoxy, $C_1$-$C_4$-alkoxy-$C_1$-$C_4$-alkyloxy, or $X^b$ represents a $C_2$-$C_5$-carbon chain which optionally contains 1 heteroatom from the group consisting of N, S and O, which is attached at two adjacent ring positions and which forms an aliphatic, aromatic, heteroaromatic or heterocyclic ring, in which case m equals 2.

Particularly preferred substituents or ranges for the radicals listed in the compounds of formula (I) are elucidated below. The combination thereof forms the range of preference (2-1).

Q represents oxygen,

V represents a radical from the group consisting of hydrogen, fluorine, chlorine, bromine, methyl and ethyl, W represents a radical from the group consisting of hydrogen, fluorine, chlorine, bromine, cyano and methyl, Y represents a radical from the group consisting of hydrogen, $C_1$-$C_4$-alkyl, $C_3$-$C_4$-alkenyl or $C_3$-$C_4$-alkynyl, optionally mono- to pentasubstituted independently of one another by fluorine, chlorine, bromine, methoxy or ethoxy, and $C_3$-$C_6$-cycloalkyl, optionally mono- to disubstituted independently of one another by fluorine, chlorine, bromine, methyl, ethyl, trifluoromethyl, methoxy, ethoxy or cyano, A represents a radical from the group consisting of hydrogen, $C_1$-$C_6$-alkyl, $C_3$-$C_6$-alkenyl or $C_3$-$C_6$-alkynyl, optionally mono- to pentasubstituted independently of one another by fluorine, chlorine, bromine, methoxy, ethoxy or cyano, and $C_3$-$C_6$-cycloalkyl, optionally mono- to disubstituted independently of one another by fluorine, chlorine, bromine, methyl, ethyl, trifluoromethyl, methoxy, ethoxy or cyano, T represents an electron pair, $L^1$ and $L^2$ represent, together with N, a heterocycle from the group U-1, U-2, U-3, U-4, U-5, U-6, U-7, U-25, U-26, U-27, U-28, U-29 and U-30, $X^b$ represents a radical from the group consisting of halogen, nitro, cyano, $C_1$-$C_4$-alkyl, $C_3$-$C_6$-cycloalkyl, $C_1$-$C_2$-haloalkyl, $C_1$-$C_4$-alkoxy, $C_1$-$C_4$-haloalkoxy, $C_3$-$C_6$-halocycloalkyl, $C_1$-$C_4$-alkoxy-$C_1$-$C_4$-alkyl, $C_1$-$C_6$-alkylthio, $C_1$-$C_4$-alkoxycarbonyl, $C_1$-$C_4$-alkylaminocarbonyl, $C_1$-$C_6$-alkylsulphonyl, $C_1$-$C_6$-alkylcarbonylamino and phenyl, wherein phenyl may optionally be mono- to trisubstituted by fluorine, chlorine, bromine, methyl, ethyl, difluoromethyl, trifluoromethyl, methoxy, ethoxy, Me-$S(O)_n$—, Et-$S(O)_n$—, difluoromethoxy, trifluoromethoxy, trifluoromethyl-$S(O)_n$—, difluoroethyl-$S(O)_n$—, trifluoroethyl-$S(O)_n$—, nitro or cyano, m represents a number 0, 1 or 2, n represents a number 0, 1 or 2, and salts thereof.

Further preferred substituents or ranges for the radicals listed in the compounds of the formula (I) are illustrated below. The combination thereof forms the range of preference (2-2), where Q, V, W, Y, A, T, $L^1$, $L^2$, m and n are as defined in the range of preference (2-1) and $X^b$ represents a radical from the group consisting of halogen, nitro, cyano, amino, $C_1$-$C_4$-alkyl, $C_3$-$C_6$-cycloalkyl, $C_1$-$C_2$-haloalkyl, $C_1$-$C_4$-alkoxy, $C_1$-$C_4$-haloalkoxy, $C_3$-$C_6$-halocycloalkyl, $C_1$-$C_4$-alkoxy-$C_1$-$C_4$-alkyl, $C_1$-$C_6$-alkylthio, $C_1$-$C_4$-alkoxycarbonyl, $C_1$-$C_4$-alkylaminocarbonyl, $C_1$-$C_6$-alkylsulphonyl, $C_1$-$C_6$-alkylcarbonylamino and phenyl, wherein phenyl may optionally be mono- to trisubstituted by fluorine, chlorine, bromine, methyl, ethyl, difluoromethyl, trifluoromethyl, methoxy, ethoxy, Me-$S(O)_n$—, Et-$S(O)_n$—, difluoromethoxy, trifluoromethoxy, trifluoromethyl-$S(O)_n$, difluoroethyl-$S(O)_n$—, trifluoroethyl-$S(O)_n$—, nitro or cyano, or $X^b$ represents a $C_3$-$C_5$-carbon chain, which is attached to two adjacent ring positions and forms an aliphatic ring, in which case m is equal to 2.

Very particularly preferred substituents or ranges of the radicals listed in the compounds of the formula (I) are illustrated below. Taking into account the position of the carboxamide group at the imidazole radical, the very particularly preferred structure (I-1) is obtained. The combination thereof forms the range of preference (3-1).

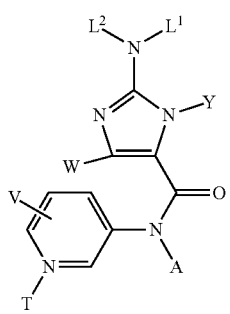

(I-1)

V represents a radical from the group consisting of hydrogen, fluorine, chlorine, methyl and cyano, W represents a radical from the group consisting of hydrogen, fluorine, chlorine, bromine and methyl, Y represents a radical from the group consisting of methyl, ethyl, propyl, allyl or propargyl, optionally mono- to trisubstituted independently of one another by fluorine, methoxy, ethoxy or cyano, A represents a radical from the group consisting of hydrogen and methyl, ethyl, propyl, allyl, propargyl or cyclopropyl, optionally mono- to trisubstituted independently of one another by fluorine, methoxy, ethoxy or cyano, T represents an electron pair, $L^1$ and $L^2$ represent, together with N, a heterocycle from the group U-1, U-2, U-3, U-4, U-5, U-6, U-7, U-25, U-26, U-27, U-29 and U-30, $X^b$ represents a radical from the group consisting of fluorine, chlorine, bromine, cyano, methyl, ethyl, n- and isopropyl, cyclopropyl, trifluoromethyl, difluoromethyl, trifluoroethyl, methoxy, ethoxy, n- and isopropoxy, trifluoromethoxy, methoxymethyl, ethoxymethyl, methoxyethyl, ethoxyethyl, methyl-$S(O)_n$—, ethyl-$S(O)_n$—, methoxycarbonyl, ethoxycarbonyl, methylaminocarbonyl, methylcarbonylamino or phenyl, where phenyl may optionally be mono- to trisubstituted by fluorine, chlorine, bromine, methyl, ethyl, difluoromethyl, trifluoromethyl, methoxy, ethoxy, nitro or cyano, m represents a number 0, 1 or 2, n represents a number 0, 1 or 2, and salts thereof.

Taking into account the position of the carboxamide group at the imidazole radical, formula (I) gives the very particularly preferred structure (I-1). Very particularly preferred substituents or ranges of the radicals listed in the compounds of the formula (I-1) are illustrated below. The combination thereof forms the range of preference (3-2), where V, W, Y, A, T, $L^1$, $L^2$, m and n are as defined in the range of preference (3-1) and $X^b$ represents a radical from the group consisting of fluorine, chlorine, bromine, cyano, amino, methyl, ethyl, n- and isopropyl, cyclopropyl, trifluoromethyl, difluoromethyl, trifluoroethyl, methoxy, ethoxy, n- and isopropoxy, trifluoromethoxy, methoxymethyl, ethoxymethyl, methoxyethyl, ethoxyethyl, methyl-$S(O)_n$—, ethyl-$S(O)_n$—, methoxycarbonyl, ethoxycarbonyl, methylaminocarbonyl, methylcarbonylamino or phenyl, where phenyl may optionally be mono- to trisubstituted by fluorine, chlorine, bromine, methyl, ethyl, difluoromethyl, trifluoromethyl, methoxy, ethoxy, nitro or cyano, or $X^b$ represents a $C_3$-$C_5$-carbon chain, which is attached to two adjacent ring positions and forms an aliphatic ring, in which case m is equal to 2.

Especially preferred substituents or ranges for the radicals listed in the compounds of the formula (I-1) are elucidated below. Its combination with the especially preferred substituents forms the preferred range (4-1), where

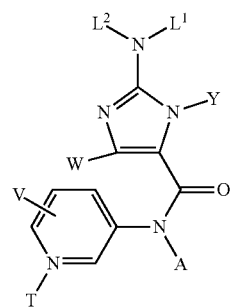

(I-1)

V represents hydrogen,

W represents hydrogen,

Y represents a radical from the group consisting of hydrogen, methyl, ethyl, allyl and propargyl, A represents a radical from the group consisting of hydrogen, methyl and ethyl, T represents an electron pair, $L^1$ and $L^2$ represent, together with N, a heterocycle from the group U-1, U-2, U-3, U-6, U-25, U-26 and U-29, $X^b$ represents a radical from the group consisting of fluorine, chlorine, bromine, cyano, methyl, ethyl, n- and isopropyl, trifluoromethyl, methoxy, ethoxy, methylthio and phenyl, where phenyl may optionally be mono- to trisubstituted by fluorine, chlorine, methyl or methoxy, m represents a number 0, 1 or 2, and salts thereof.

Especially preferred substituents or ranges for the radicals listed in the compounds of the formula (I-1) are elucidated below. Its combination with the especially preferred substituents forms the preferred range (4-2), where V, W, Y, T, $L^1$, $L^2$ and m are as defined in the range of preference (4-1) and A represents a radical from the group consisting of hydrogen, methyl, ethyl and cyclopropyl, and $X^b$ represents a radical from the group consisting of fluorine, chlorine, bromine, cyano, amino, methyl, ethyl, n- and isopropyl, trifluoromethyl, methoxy, ethoxy, methylthio and phenyl, where phenyl may optionally be mono- to trisubstituted by fluorine, chlorine, methyl or methoxy, or $X^b$ represents a $C_3$-$C_4$-carbon chain, which is attached to two adjacent ring positions and forms an aliphatic ring, in which case m is equal to 2.

Very particularly preferred substituents or ranges of the radicals listed in the compounds of the formula (I-1) are illustrated below. The combination thereof forms the range of preference (5-1).

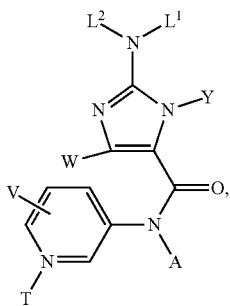

(I-1)

V represents hydrogen,
W represents hydrogen,
Y represents methyl,
A represents methyl or ethyl,
T represents an electron pair,
$L^1$ and $L^2$ represent, together with N, a heterocycle from the group U-1, U-2, U-3, U-6, U-25, U-26 and U-29,
$X^b$ represents a radical from the group consisting of chlorine, cyano, methyl, trifluoromethyl, methylthio and phenyl,
m represents a number 0, 1 or 2,
and salts thereof.

Very particularly preferred substituents or ranges of the radicals listed in the compounds of the formula (I-1) are illustrated below. The combination thereof forms the range of preference (5-2),
where
V, W, Y, T, $L^1$, $L^2$ and m are as defined in the range of preference (5-1) and
A represents methyl, ethyl or cyclopropyl, and
$X^b$ represents a radical from the group consisting of chlorine, cyano, amino, methyl, isopropyl, trifluoromethyl, methylthio and phenyl, or
$X^b$ represents —$(CH_2)_3$—, which is attached to two adjacent ring positions and forms an aliphatic ring, in which case m is equal to 2.

In a preferred embodiment, the invention relates to the compounds of the formula (I) or of the formula (I-1), where the radicals Q, V, W, Y, A, T and n are as defined in range of preference (1-1) or range of preference (1-2) or range of preference (2-1) or range of preference (2-2) or range of preference (3-1) or range of preference (3-2) or range of preference (4-1) or range of preference (4-2) or range of preference (5-1) or range of preference (5-2) and
$L^1$, $L^2$, $X^b$, $R^2$, $R^3$, $R^4$, $R^{3a}$, $R^{4a}$, $R^5$, $R^6$ and m have the meanings described in embodiment (0).

In a preferred embodiment, the invention relates to the compounds of the formula (I) or of the formula (I-1), where the radicals Q, V, W, Y, A, T and n are as defined in embodiment (0) or range of preference (2-1) or range of preference (2-2) or range of preference (3-1) or range of preference (3-2) or range of preference (4-1) or range of preference (4-2) or range of preference (5-1) or range of preference (5-2) and
$L^1$, $L^2$, $X^b$, $R^2$, $R^3$, $R^4$, $R^{3a}$, $R^{4a}$, $R^5$, $R^6$ and m have the meanings described in range of preference (1-1) or (1-2).

In a preferred embodiment, the invention relates to the compounds of the formula (I) or of the formula (I-1), where the radicals Q, V, W, Y, A, T and n are as defined in embodiment (0-1) or embodiment (0-2) or range of preference (1-1) or range of preference (1-2) or range of preference (3-1) or range of preference (3-2) or range of preference (4-1) or range of preference (4-2) or range of preference (5-1) or range of preference (5-2) and
$L^1$, $L^2$, $X^b$ and m have the meanings described in range of preference (2-1) or (2-2).

In a preferred embodiment, the invention relates to the compounds of the formula (I) or of the formula (I-1), where the radicals Q, V, W, Y, A, T and n are as defined in embodiment (0-1) or embodiment (0-2) or range of preference (1-1) or range of preference (1-2) or range of preference (2-1) or range of preference (2-2) or range of preference (4-1) or range of preference (4-2) or range of preference (5-1) or range of preference (5-2) and
$L^1$, $L^2$, $X^b$ and m have the meanings described in range of preference (3-1) or (3-2).

In a preferred embodiment, the invention relates to the compounds of the formula (I) or of the formula (I-1), where the radicals Q, V, W, Y, A, T and n are as defined in embodiment (0-1) or embodiment (0-2) or range of preference (1-1) or range of preference (1-2) or range of preference (2-1) or range of preference (2-2) or range of preference (3-1) or range of preference (3-2) or range of preference (5-1) or range of preference (5-2) and
$L^1$, $L^2$, $X^b$ and m have the meanings described in range of preference (4-1) or range of preference (4-2).

In a preferred embodiment, the invention relates to the compounds of the formula (I) or of the formula (I-1), where the radicals Q, V, W, Y, A, T and n are as defined in embodiment (0-1) or embodiment (0-2) or range of preference (1-1) or range of preference (1-2) or range of preference (2-1) or range of preference (2-2) or range of preference (3-1) or range of preference (3-2) or range of preference (4-1) or range of preference (4-2) and
$L^1$, $L^2$, $X^b$ and m have the meanings described in range of preference (5-1) or range of preference (5-2).

In preferred range (1-1) or (1-2), unless stated otherwise,
halogen is selected from the group of fluorine, chlorine, bromine and iodine, preferably in turn from the group of fluorine, chlorine and bromine,
hetaryl (synonymous with heteroaryl, including as part of a larger unit, for example hetarylalkyl) is selected from the group consisting of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzoisofuryl, benzothienyl, benzoisothienyl, indolyl, isoindolyl, indazolyl, benzothiazolyl, benzoisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl,
heterocyclyl represents a saturated 3-, 4-, 5- or 6-membered ring which contains 1 or 2 nitrogen atoms and/or one oxygen atom and/or one sulphur atom, but where 2 nitrogen atoms shall not be directly vicinal, for example aziridinyl, azetidinyl, azolidinyl, azinanyl, oxiranyl, oxetanyl, oxolanyl, oxanyl, dioxanyl, thiiranyl, thietanyl, thiolanyl, thianyl and tetrahydrofuryl.

In preferred range (2-1) or (2-2), unless stated otherwise,
halogen represents fluorine, chlorine, bromine and iodine, preferably fluorine, chlorine and bromine,
hetaryl (including as part of a larger unit, such as hetarylalkyl) represents pyridyl, pyrimidyl, thiazolyl, oxazolyl, pyrazolyl, thienyl, furanyl, benzyl, pyridinylmethyl and thiazolylmethyl, and heterocyclyl (including as part of a larger unit, such as heterocyclylalkyl) represents a saturated or unsaturated 3-, 4- or 5-membered ring which contains 1 or 2 nitrogen atoms and/or one oxygen atom and/or one sulphur atom, but where 2 nitrogen atoms shall not be directly vicinal, for example 1- or 2-aziridinyl, 2-oxiranyl, 2-thiiranyl, 1- or 2-azetidinyl, 2- or 3-oxetanyl, 2- or 3-thietanyl, 1,3-dioxetan-2-yl, 1-, 2- or 3-pyrrolidinyl.

In preferred range (3-1) or (3-2), unless stated otherwise,
halogen represents fluorine, chlorine, bromine and iodine, preferably fluorine, chlorine and bromine, and
heterocyclyl (including as part of a larger unit, such as heterocyclylalkyl) represents a saturated or unsaturated 3- or 4-membered ring which contains 1 or 2 nitrogen atoms and/or one oxygen atom and/or one sulphur atom, but where 2 nitrogen atoms shall not be directly vicinal, for example 1- or 2-aziridinyl, 2-oxiranyl, 2-thiiranyl, 1- or 2-azetidinyl, 2- or 3-oxetanyl, 2- or 3-thietanyl or 1,3-dioxetan-2-yl. Halogen-substituted radicals, for example haloalkyl, are, unless otherwise specified, monohalogenated or polyhalogenated up to the maximum number of possible substituents. In the case of polyhalogenation, the halogen atoms may be identical or different. In this case, halogen is fluorine, chlorine, bromine or iodine, especially fluorine, chlorine or bromine.

Saturated or unsaturated hydrocarbon radicals, such as alkyl or alkenyl, may each be straight-chain or branched if possible, including in combination with heteroatoms, as, for example, in alkoxy.

Unless stated otherwise, optionally substituted radicals may be mono- or polysubstituted, where the substituents in the case of polysubstitutions may be the same or different.

If, in the compounds of the formula (I), T represents oxygen, these compounds are present as N-oxides.

If, in the compounds of the formula (I), T represents an electron pair, these compounds are present as pyridines.

The radical definitions or elucidations given in general terms or listed within areas of preference apply correspondingly to end products and to starting materials and intermediates. These radical definitions can be combined with one another as desired, i.e. including combinations between the respective ranges of preference.

Preference according to the invention is given to using compounds of the formula (I) which contain a combination of the meanings listed above as being preferred (preferred range (1-1) or (1-2)).

Particular preference according to the invention is given to using compounds of the formula (I) which contain a combination of the meanings listed above as being particularly preferred (preferred range (2-1) or (2-2)).

Very particular preference according to the invention is given to using compounds of the formula (I) which contain a combination of the definitions listed above as being very particularly preferred (preferred range (3-1) or (3-2)).

Special preference according to the invention is given to using compounds of the formula (I) which contain a combination of the definitions listed above as being very particularly preferred (preferred range (4-1) or (4-2)).

Even more preference according to the invention is given to using compounds of the formula (I) which contain a combination of the definitions listed above as being very particularly preferred (preferred range (5-1) or (5-2)).

Hereinbelow, the statements concerning the compounds of the formula (I) do, of course, also apply to the compounds of the formulae (I-1) which are embraced by formula (I).

Isomers

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. The invention therefore encompasses both pure stereoisomers and any desired mixtures of these isomers.

Methods and Uses

The invention also relates to methods for controlling animal pests, in which compounds of the formula (I) are allowed to act on animal pests and/or their habitat. The control of the animal pests is preferably conducted in agriculture and forestry, and in material protection. This preferably excludes methods for surgical or therapeutic treatment of the human or animal body and diagnostic methods carried out on the human or animal body.

The invention further relates to the use of the compounds of the formula (I) as pesticides, in particular crop protection agents.

In the context of the present application, the term "pesticide" in each case also always encompasses the term "crop protection agent".

The compounds of the formula (I), given good plant tolerance, favourable endotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, especially nematodes and molluscs, which are encountered in agriculture, in horticulture, in animal husbandry, in aquatic cultures, in forests, in gardens and leisure facilities, in the protection of stored products and of materials, and in the hygiene sector.

In the context of the present patent application, the term "hygiene" should be understood to mean any and all measures, provisions and procedures which have the aim of preventing diseases, especially infection diseases, and which serve to protect the health of humans and animals and/or protect the environment and/or maintain cleanliness. According to the invention, this especially includes measures for cleaning, disinfection and sterilization, for example of textiles or hard surfaces, especially surfaces made of glass, wood, cement, porcelain, ceramic, plastic or else metal(s), in order to ensure that these are free of hygiene pests and/or their secretions. The scope of protection of the invention in this regard preferably excludes surgical or therapeutic treatment procedures to be applied to the human body or the bodies of animals, and diagnostic procedures which are conducted on the human body or the bodies of animals.

The term "hygiene sector" covers all areas, technical fields and industrial applications in which these hygiene measures, provisions and procedures are important, for example with regard to hygiene in kitchens, bakeries, airports, bathrooms, swimming pools, department stores, hotels, hospitals, stables, animal keeping, etc.

The term "hygiene pest" should therefore be understood to mean one or more animal pests whose presence in the hygiene sector is problematic, especially for reasons of health. A main aim is therefore that of avoiding, or limiting to a minimum degree, the presence of hygiene pests and/or the exposure to these in the hygiene sector. This can especially be achieved through the use of a pesticide which can be used both for prevention of infestation and for prevention of an existing infestation. It is also possible to use formulations which prevent or reduce exposure to pests. Hygiene pests include, for example, the organisms mentioned below.

The term "hygiene protection" thus covers all acts by which these hygiene measures, provisions and procedures are maintained and/or improved.

The compounds of the formula (I) can preferably be used as pesticides. They are active against normally sensitive and resistant species and also against all or specific stages of development. The abovementioned pests include:

pests from the phylum of the Arthropoda, especially from the class of the Arachnida, for example *Acarus* spp., e.g. *Acarus siro, Aceria kuko, Aceria sheldoni, Aculops* spp., *Aculus* spp., e.g. *Aculus fockeui, Aculus schlechtendali, Amblyomma* spp., *Amphitetranychus viennensis, Argas* spp., *Boophilus* spp., *Brevipalpus* spp., e.g. *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., e.g. *Eotetranychus hicoriae, Epitrimerus pyri, Eutetranychus* spp., e.g. *Eutetranychus banksi, Eriophyes* spp., e.g. *Eriophyes pyri, Glycyphagus domesticus, Halotydeus destructor, Hemitarsonemus* spp., e.g. *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., e.g. *Oligonychus coffeae, Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., e.g. *Panonychus citri* (=*Metatetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., e.g. *Tarsonemus confusus, Tarsonemus pallidus, Tetranychus* spp., e.g. *Tetranychus canadensis, Tetranychus cinnabarinus, Tetranychus turkestani, Tetranychus urticae, Trombicula alfreddugesi, Vaejovis* spp., *Vasates lycopersici*; from the class of the Chilopoda, for example *Geophilus* spp., *Scutigera* spp.;

from the order or the class of the Collembola, for example *Onychiurus armatus; Sminthurus viridis;* from the class of the Diplopoda, for example *Blaniulus guttulatus;* from the class of the Insecta, for example from the order of the Blattodea, e.g. *Blatta orientalis, Blattella asahinai, Blattella germanica, Leucophaea maderae, Loboptera decipiens, Neostylopyga rhombifolia, Panchlora* spp., *Parcoblatta* spp., *Periplaneta* spp., e.g. *Periplaneta americana, Periplaneta australasiae, Pycnoscelus surinamensis, Supella longipalpa;* from the order of the Coleoptera for example *Acalymma vittatum, Acanthoscelides obtectus, Adoretus* spp., *Aethina tumida, Agelastica alni, Agriotes* spp., e.g. *Agriotes linneatus, Agriotes mancus, Alphitobius diaperinus, Amphimallon solstitialis, Anobium punctatum, Anoplophora* spp., *Anthonomus* spp., e.g. *Anthonomus grandis, Anthrenus* spp., *Apion* spp., *Apogonia* spp., *Atomaria* spp., e.g. *Atomaria linearis, Attagenus* spp., *Baris caerulescens, Bruchidius obtectus, Bruchus* spp., e.g. *Bruchus pisorum, Bruchus rufimanus, Cassida* spp., *Cerotoma trifurcata, Ceutorrhynchus* spp., e.g. *Ceutorrhynchus assimilis, Ceutorrhynchus quadridens, Ceutorrhynchus rapae, Chaetocnema* spp., e.g. *Chaetocnema confinis, Chaetocnema denticulata, Chaetocnema ectypa, Cleonus mendicus, Conoderus* spp., *Cosmopolites* spp., e.g. *Cosmopolites sordidus, Costelytra zealandica, Ctenicera* spp., *Curculio* spp., e.g. *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dermestes* spp., *Diabrotica* spp., e.g. *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epicaerus* spp., *Epilachna* spp., e.g. *Epilachna borealis, Epilachna varivestis, Epitrix* spp., e.g. *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., e.g. *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., e.g. *Leucoptera coffeella, Lissorhoptrus oryzophilus, Listronotus* (=*Hyperodes*) spp., *Lixus* spp., *Luperodes* spp., *Luperomorpha xanthodera, Lyctus* spp., *Megascelis* spp., *Melanotus* spp., e.g. *Melanotus longulus oregonensis, Meligethes aeneus, Melolontha* spp., e.g. *Melolontha melolontha, Migdolus* spp., *Monochamus* spp., *Naupactus xanthographus, Necrobia* spp., *Neogalerucella* spp., *Niptus hololeucus, Oryctes rhinoceros, Oryzaephilus surinamensis, Oryzaphagus oryzae, Otiorhynchus* spp., e.g. *Otiorhynchus cribricollis, Otiorhynchus ligustici, Otiorhynchus ovatus, Otiorhynchus rugosostriarus, Otiorhynchus sulcatus, Oulema* spp., e.g. *Oulema melanopus, Oulema oryzae, Oxycetonia jucunda, Phaedon cochleariae, Phyllophaga* spp., *Phyllophaga helleri, Phyllotreta* spp., e.g. *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., e.g. *Psylliodes affinis, Psylliodes chrysocephala, Psylliodes punctulata, Ptinus* spp., *Rhizobius ventralis, Rhizopertha dominica, Rhynchophorus* spp., *Rhynchophorus ferrugineus, Rhynchophorus palmarum, Sinoxylon perforans, Sitophilus* spp., e.g. *Sitophilus granarius, Sitophilus linearis, Sitophilus oryzae, Sitophilus zeamais, Sphenophorus* spp., *Stegobium paniceum, Sternechus* spp., e.g. *Sternechus paludatus, Symphyletes* spp., *Tanymecus* spp., e.g. *Tanymecus dilaticollis, Tanymecus indicus, Tanymecus palliatus, Tenebrio molitor, Tenebrioides mauretanicus, Tribolium* spp., e.g. *Tribolium audax, Tribolium castaneum, Tribolium confusum, Trogoderma* spp., *Tychius* spp., *Xylotrechus* spp., *Zabrus* spp., e.g. *Zabrus tenebrioides;* from the order of the Dermaptera, for example *Anisolabis maritime, Forficula auricularia, Labidura riparia;* from the order of the Diptera, for example *Aedes* spp., e.g. *Aedes aegypti, Aedes albopictus, Aedes sticticus, Aedes vexans, Agromyza* spp., e.g. *Agromyza frontella, Agromyza parvicornis, Anastrepha* spp., *Anopheles* spp., e.g. *Anopheles quadrimaculatus, Anopheles gambiae, Asphondylia* spp., *Bactrocera* spp., e.g. *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., e.g. *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., e.g. *Culex pipiens, Culex quinquefasciatus, Culicoides* spp., *Culiseta* spp., *Cuterebra* spp., *Dacus oleae, Dasineura* spp., e.g. *Dasineura brassicae, Delia* spp., e.g.

*Delia antiqua, Delia coarctata, Delia florilega, Delia platura, Delia radicum, Dermatobia hominis, Drosophila* spp., e.g. *Drosphila melanogaster, Drosophila suzukii, Echinocnemus* spp., *Euleia heraclei, Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., e.g. *Liriomyza brassicae, Liriomyza huidobrensis, Liriomyza sativae, Lucilia* spp., e.g. *Lucilia cuprina, Lutzomyia* spp., *Mansonia* spp., *Musca* spp., e.g. *Musca domestica, Musca domestica vicina, Oestrus* spp., *Oscinella frit, Paratanytarsus* spp., *Paralauterborniella subcincta, Pegomya oder Pegomyia* spp., e.g. *Pegomya betae, Pegomya hyoscyami, Pegomya rubivora, Phlebotomus* spp., *Phorbia* spp., *Phormia* spp., *Piophila casei, Platyparea poeciloptera, Prodiplosis* spp., *Psila rosae, Rhagoletis* spp., e.g. *Rhagoletis cingulata, Rhagoletis completa, Rhagoletis fausta, Rhagoletis indifferens, Rhagoletis mendax, Rhagoletis pomonella, Sarcophaga* spp., *Simulium* spp., e.g. *Simulium meridionale, Stomoxys* spp., *Tabanus* spp., *Tetanops* spp., *Tipula* spp., e.g. *Tipula paludosa, Tipula simplex, Toxotrypana curvicauda;* from the order of the Hemiptera, for example *Acizzia acaciabaileyanae, Acizzia dodonaeae, Acizzia uncatoides, Acrida turrita, Acyrthosipon* spp., e.g. *Acyrthosiphon pisum, Acrogonia* spp., *Aeneolamia* spp., *Agonoscena* spp., *Aleurocanthus* spp., *Aleyrodes proletella, Aleurolobus barodensis, Aleurothrixus floccosus, Allocaridara malayensis, Amrasca* spp., e.g. *Amrasca bigutulla, Amrasca devastans, Anuraphis cardui, Aonidiella* spp., e.g. *Aonidiella aurantii, Aonidiella citrina, Aonidiella inornata, Aphanostigma piri, Aphis* spp., e.g. *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., e.g. *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., e.g. *Cacopsylla pyricola, Calligypona marginata, Capulinia* spp., *Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus aonidum, Chrysomphalus ficus, Cicadulina mbila, Coccomytilus halli, Coccus* spp., e.g. *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes chittendeni, Dialeurodes citri, Diaphorina citri, Diaspis* spp., *Diuraphis* spp., *Doralis* spp., *Drosicha* spp., *Dysaphis* spp., e.g. *Dysaphis apiifolia, Dysaphis plantaginea, Dysaphis tulipae, Dysmicoccus* spp., *Empoasca* spp., e.g. *Empoasca abrupta, Empoasca fabae, Empoasca maligna, Empoasca solana, Empoasca stevensi, Eriosoma* spp., e.g. *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Fiorinia* spp., *Furcaspis oceanica, Geococcus coffeae, Glycaspis* spp., *Heteropsylla cubana, Heteropsylla spinulosa, Homalodisca coagulata, Hyalopterus arundinis, Hyalopterus pruni, Icerya* spp., e.g. *Icerya purchasi, Idiocerus* spp., *Idioscopus* spp., *Laodelphax striatellus, Lecanium* spp., e.g. *Lecanium corni* (=*Parthenolecanium corni*), *Lepidosaphes* spp., e.g. *Lepidosaphes ulmi, Lipaphis erysimi, Lopholeucaspis japonica, Lycorma delicatula, Macrosiphum* spp., e.g. *Macrosiphum euphorbiae, Macrosiphum lilii, Macrosiphum rosae, Macrosteles facifrons, Mahanarva* spp., *Melanaphis sacchari, Metcalfiella* spp., *Metcalfa pruinosa, Metopolophium dirhodum, Monellia costalis, Monelliopsis pecanis, Myzus* spp., e.g. *Myzus ascalonicus, Myzus cerasi, Myzus ligustri, Myzus ornatus, Myzus persicae, Myzus nicotianae, Nasonovia ribisnigri, Neomaskellia* spp., *Nephotettix* spp., e.g. *Nephotettix cincticeps, Nephotettix nigropictus, Nettigoniclla spectra, Nilaparvata lugens, Oncometopia* spp., *Orthezia praelonga, Oxya chinensis, Pachypsylla* spp., *Parabemisia myricae, Paratrioza* spp., e.g. *Paratrioza cockerelli, Parlatoria* spp., *Pemphigus* spp., e.g. *Pemphigus bursarius, Pemphigus populivenae, Peregrinus maidis, Perkinsiella* spp., *Phenacoccus* spp., e.g. *Phenacoccus madeirensis, Phloeomyzus passerinii, Phorodon humuli, Phylloxera* spp., e.g. *Phylloxera devastatrix, Phylloxera notabilis, Pinnaspis aspidistrae, Planococcus* spp., e.g. *Planococcus citri, Prosopidopsylla flava, Protopulvinaria pyriformis, Pseudaulacaspis pentagona, Pseudococcus* spp., e.g. *Pseudococcus calceolariae, Pseudococcus comstocki, Pseudococcus longispinus, Pseudococcus maritimus, Pseudococcus viburni, Psyllopsis* spp., *Psylla* spp., e.g. *Psylla buxi, Psylla mali, Psylla pyri, Pteromalus* spp., *Pulvinaria* spp., *Pyrilla* spp., *Quadraspidiotus* spp., e.g. *Quadraspidiotus juglansregiae, Quadraspidiotus ostreaeformis, Quadraspidiotus perniciosus, Quesada gigas, Rastrococcus* spp., *Rhopalosiphum* spp., e.g. *Rhopalosiphum maidis, Rhopalosiphum oxyacanthae, Rhopalosiphum padi, Rhopalosiphum rufiabdominale, Saissetia* spp., e.g. *Saissetia coffeae, Saissetia miranda, Saissetia neglecta, Saissetia oleae, Scaphoideus titanus, Schizaphis graminum, Selenaspidus articulatus, Sipha flava, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., e.g. *Toxoptera aurantii, Toxoptera citricidus, Trialeurodes vaporariorum, Trioza* spp., e.g. *Trioza diospyri, Typhlocyba* spp., *Unaspis* spp., *Viteus vitifolii, Zygina* spp.;

from the suborder of the Heteroptera, for example *Aelia* spp., *Anasa tristis, Antestiopsis* spp., *Boisea* spp., *Blissus* spp., *Calocoris* spp., *Campylomma livida, Cavelerius* spp., *Cimex* spp., e.g. *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., e.g. *Euschistus heros, Euschistus servus, Euschistus tristigmus, Euschistus variolarius, Eurydema* spp., *Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., e.g. *Lygocoris pabulinus, Lygus* spp., e.g. *Lygus elisus, Lygus hesperus, Lygus lineolaris, Macropes excavatus, Megacopta cribraria, Miridae, Monalonion atratum, Nezara* spp., e.g. *Nezara viridula, Nysius* spp., *Oebalus* spp., *Pentomidae, Piesma quadrata, Piezodorus* spp., e.g. *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera, for example *Acromyrmex* spp., *Athalia* spp., e.g. *Athalia rosae, Atta* spp., *Camponotus* spp., *Dolichovespula* spp., *Diprion* spp., e.g. *Diprion similis, Hoplocampa* spp., e.g. *Hoplocampa cookei, Hoplocampa testudinea, Lasius* spp., *Linepithema* (*Iridiomyrmex*) *humile, Monomorium pharaonis, Paratrechina* spp., *Paravespula* spp., *Plagiolepis* spp., *Sirex* spp., *Solenopsis invicta, Tapinoma* spp., *Technomyrmex albipes, Urocerus* spp., *Vespa* spp., e.g. *Vespa crabro, Wasmannia auropunctata, Xeris* spp.;

from the order of the Isopoda, for example *Armadillidium vulgare, Oniscus asellus, Porcellio scaber*;

from the order of the Isoptera, for example *Coptotermes* spp., e.g. *Coptotermes formosanus, Cornitermes cumulans, Cryptotermes* spp., *Incisitermes* spp., *Kalotermes* spp., *Microtermes obesi, Nasutitermes* spp., *Odontotermes* spp., *Porotermes* spp., *Reticulitermes* spp., e.g. *Reticulitermes flavipes, Reticulitermes hesperus*;

from the order of the Lepidoptera, for example *Achroia grisella, Acronicta major, Adoxophyes* spp., e.g. *Adoxophyes orana, Aedia leucomelas, Agrotis* spp., e.g. *Agrotis segetum, Agrotis ipsilon, Alabama* spp., e.g. *Alabama argillacea, Amyelois transitella, Anarsia* spp., *Anticarsia* spp., e.g. *Anticarsia gemmatalis, Argyroploce* spp., *Autographa* spp., *Barathra brassicae, Blastodacna atra, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., e.g. *Chilo plejadellus, Chilo suppressalis, Choreutis pariana, Choristoneura* spp., *Chrysodeixis chalcites, Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., e.g. *Cydia nigricana, Cydia pomonella, Dalaca noctuides, Diaphania* spp., *Diparopsis* spp., *Diatraea saccharalis, Earias* spp., *Ecdytolopha aurantium, Elasmopalpus lignosellus, Eldana saccharina, Ephestia* spp., e.g. *Ephestia elutella, Ephestia kuehniella, Epinotia* spp., *Epiphyas postvittana, Erannis* spp., *Erschoviella musculana, Etiella* spp., *Eudocima* spp., *Eulia* spp., *Eupoecilia ambiguella, Euproctis* spp., e.g. *Euproctis chrysorrhoea, Euxoa* spp., *Feltia* spp., *Galleria mellonella, Gracillaria* spp., *Grapholitha* spp., e.g. *Grapholita molesta, Grapholita prunivora, Hedylepta* spp., *Helicoverpa* spp., e.g. *Helicoverpa armigera, Helicoverpa zea, Heliothis* spp., e.g. *Heliothis virescens Hofmannophila pseudospretella, Homoeosoma* spp., *Homona* spp., *Hyponomeuta padella, Kakivoria flavofasciata, Lampides* spp., *Laphygma* spp., *Laspeyresia molesta, Leucinodes orbonalis, Leucoptera* spp., e.g. *Leucoptera coffeella, Lithocolletis* spp., e.g. *Lithocolletis blancardella, Lithophane antennata, Lobesia* spp., e.g. *Lobesia botrana, Loxagrotis albicosta, Lymantria* spp., e.g. *Lymantria dispar, Lyonetia* spp., e.g. *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Omphisa* spp., *Operophtera* spp., *Oria* spp., *Orthaga* spp., *Ostrinia* spp., e.g. *Ostrinia nubilalis, Panolis flammea, Parnara* spp., *Pectinophora* spp., e.g. *Pectinophora gossypiella, Perileucoptera* spp., *Phthorimaea* spp., e.g. *Phthorimaea operculella, Phyllocnistis citrella, Phyllonorycter* spp., e.g. *Phyllonorycter blancardella, Phyllonorycter crataegella, Pieris* spp., e.g. *Pieris rapae, Platynota stultana, Plodia interpunctella, Plusia* spp., *Plutella xylostella* (=*Plutella maculipennis*), *Prays* spp., *Prodenia* spp., *Protoparce* spp., *Pseudaletia* spp., e.g. *Pseudaletia unipuncta, Pseudoplusia includens, Pyrausta nubilalis, Rachiplusia nu, Schoenobius* spp., e.g. *Schoenobius bipunctifer, Scirpophaga* spp., e.g. *Scirpophaga innotata, Scotia segetum, Sesamia* spp., e.g. *Sesamia inferens, Sparganothis* spp., *Spodoptera* spp., e.g. *Spodoptera eradiana, Spodoptera exigua, Spodoptera frugiperda, Spodoptera praefica, Stathmopoda* spp., *Stenoma* spp., *Stomopteryx subsecivella, Synanthedon* spp., *Tecia solanivora, Thaumetopoea* spp., *Thermesia gemmatalis, Tinea cloacella, Tinea pellionella, Tineola bisselliella, Tortrix* spp., *Trichophaga tapetzella, Trichoplusia* spp., e.g. *Trichoplusia ni, Tryporyza incertulas, Tuta absoluta, Virachola* spp.;

from the order of the Orthoptera or Saltatoria, for example *Acheta domesticus, Dichroplus* spp., *Gryllotalpa* spp., e.g. *Gryllotalpa gryllotalpa, Hieroglyphus* spp., *Locusta* spp., e.g. *Locusta migratoria, Melanoplus* spp., e.g. *Melanoplus devastator, Paratlanticus ussuriensis, Schistocerca gregaria*;

from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera, for example *Ceratophyllus* spp., *Ctenocephalides* spp., e.g. *Ctenocephalides canis, Ctenocephalides felis, Pulex irritans, Tunga penetrans, Xenopsylla cheopis*;

from the order of the Thysanoptera, for example *Anaphothrips obscurus, Baliothrips biformis, Chaetanaphothrips leeuweni, Drepanothrips reuteri, Enneothrips flavens, Frankliniella* spp., e.g. *Frankliniella fusca, Frankliniella occidentalis, Frankliniella schultzei, Frankliniella tritici, Frankliniella vaccinii, Frankliniella williamsi, Haplothrips* spp., *Heliothrips* spp., *Hercinothrips femoralis, Kakothrips* spp., *Rhipiphorothrips cruentatus, Scirtothrips* spp., *Taeniothrips cardamomi, Thrips* spp., e.g. *Thrips palmi, Thrips tabaci*;

from the order of the Zygentoma (=Thysanura), for example *Ctenolepisma* spp., *Lepisma saccharina, Lepismodes inquilinus, Thermobia domestica*;

from the class of the Symphyla, for example *Scutigerella* spp., e.g. *Scutigerella immaculata*; pests from the phylum of the Mollusca, for example from the class of the Bivalvia, e.g. *Dreissena* spp.; and also from the class of the Gastropoda, for example *Arion* spp., e.g. *Arion ater rufus, Biomphalaria* spp., *Bulinus* spp., *Deroceras* spp., e.g. *Deroceras laeve, Galba* spp., *Lymnaea* spp., *Oncomelania* spp., *Pomacea* spp., *Succinea* spp.;

plant pests from the phylum of the Nematoda, i.e. plant-parasitic nematodes, in particular *Aglenchus* spp., e.g. *Aglenchus agricola, Anguina* spp., e.g. *Anguina tritici, Aphelenchoides* spp., e.g. *Aphelenchoides arachidis, Aphelenchoides fragariae, Belonolaimus* spp., e.g. *Belonolaimus gracilis, Belonolaimus longicaudatus, Belonolaimus nortoni, Bursaphelenchus* spp., e.g. *Bursaphelenchus cocophilus, Bursaphelenchus eremus, Bursaphelenchus xylophilus, Cacopaurus* spp., e.g. *Cacopaurus pestis, Criconemella* spp., e.g. *Criconemella curvata, Criconemella onoensis, Criconemella ornata, Criconemella rusium, Criconemella xenoplax* (=*Mesocriconema xenoplax*), *Criconemoides* spp., e.g. *Criconemoides ferniae, Criconemoides onoense, Criconemoides ornatum, Ditylenchus* spp., e.g. *Ditylenchus dipsaci, Dolichodorus* spp., *Globodera* spp., e.g. *Globodera pallida, Globodera rostochiensis, Helicotylenchus* spp., e.g. *Helicotylenchus dihystera, Hemicriconemoides* spp., *Hemicycliophora* spp., *Heterodera* spp., e.g. *Heterodera avenae, Heterodera glycines, Heterodera schachtii, Hirschmaniella* spp., *Hoplolaimus* spp., *Longidorus* spp., e.g. *Longidorus africanus, Meloidogyne* spp., e.g. *Meloidogyne chitwoodi, Meloidogyne fallax, Meloidogyne hapla, Meloidogyne incognita, Meloinema* spp., *Nacobbus* spp., *Neotylenchus* spp., *Paralongidorus* spp., *Paraphelenchus* spp., *Paratrichodorus* spp., e.g. *Paratrichodorus minor, Paratylenchus* spp., *Pratylenchus* spp., e.g. *Pratylenchus penetrans, Pseudohalenchus* spp., *Psilenchus* spp., *Punctodera* spp., *Quinisulcius* spp., *Radopholus* spp., e.g. *Radopholus*

*citrophilus, Radopholus similis, Rotylenchulus* spp., *Rotylenchus* spp., *Scutellonema* spp., *Subanguina* spp., *Trichodorus* spp., e.g. *Trichodorus obtusus, Trichodorus primitivus, Tylenchorhynchus* spp., e.g. *Tylenchorhynchus annulatus, Tylenchulus* spp., e.g. *Tylenchulus semipenetrans, Xiphinema* spp., e.g. *Xiphinema index*.

The compounds of the formula (I) can optionally, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (*mycoplasma*-like organisms) and RLO (*rickettsia*-like organisms). They can, as the case may be, also be used as intermediates or precursors for the synthesis of other active ingredients.

Formulations

The present invention further relates to formulations and use forms prepared therefrom as pesticides, for example drench, drip and spray liquors, comprising at least one compound of the formula (I). Optionally, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemically active compounds.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are produced in a known manner, for example by mixing the compounds of the formula (I) with auxiliaries, for example extenders, solvents and/or solid carriers and/or other auxiliaries, for example surfactants. The formulations are produced either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed-dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the simple and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle, it is possible to use all suitable solvents. Examples of suitable solvents are aromatic hydrocarbons, for example xylene, toluene or alkylnaphthalenes, chlorinated aromatic or chlorinated aliphatic hydrocarbons, for example chlorobenzene, chloroethylene or methylene chloride, aliphatic hydrocarbons, for example cyclohexane, paraffins, petroleum fractions, mineral and vegetable oils, alcohols, for example methanol, ethanol, isopropanol, butanol or glycol and their ethers and esters, ketones, for example acetone, methyl ethyl ketone, methyl isobutyl ketone or cyclohexanone, strongly polar solvents, for example dimethyl sulphoxide, and water.

In principle, it is possible to use all suitable carriers. Useful carriers especially include, for example, ammonium salts and natural, finely ground rocks, such as kaolins, aluminas, talc, chalk, quartz, attapulgite, montmorillonite or diatomaceous earth, and synthetic, finely ground rocks, such as highly disperse silica, aluminium oxide and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, maize cobs and tobacco stalks.

It is also possible to use liquefied gaseous extenders or solvents. Especially suitable extenders or carriers are those which are gaseous at standard temperature and under atmospheric pressure, for example aerosol propellants such as halogenated hydrocarbons, and also butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the compounds of the formula (I) and/or one of the inert carriers is insoluble in water and when the application takes place in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components which may be present are stabilizers, such as cold stabilizers, preservatives, antioxidants, light stabilizers, or other agents which improve chemical and/or physical stability. Foam generators or antifoams may also be present.

In addition, the formulations and the use forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

It is possible if appropriate for still further auxiliaries to be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce dynamic surface tension, for example dioctyl sulphosuccinate, or increase viscoelasticity, for example hydroxypropylguar polymers.

Useful penetrants in the present context are all those substances which are typically used to improve the penetration of active agrochemical ingredients into plants. Penetrants are defined in this context by their ability to penetrate from the (generally aqueous) application liquor and/or from the spray coating into the cuticle of the plant and hence to increase the mobility of the active ingredients in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001% and 98% by weight of the compound of the formula (I), more preferably between 0.01% and 95% by weight of the compound of the formula (I), most preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form.

Application is accomplished in a customary manner appropriate for the use forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active ingredient combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

In addition, the compounds of the formula (I) may be present in a mixture with other active compounds or semiochemicals such as attractants and/or bird repellents and/or plant activators and/or growth regulators and/or fertilizers. Likewise, the compounds of the formula (I) can be used to improve plant properties, for example growth, yield and quality of the harvested material.

In a particular embodiment according to the invention, the compounds of the formula (I) are present in formulations or in the use forms prepared from these formulations in a mixture with further compounds, preferably those as described below.

If one of the compounds mentioned below can occur in different tautomeric forms, these forms are also included even if not explicitly mentioned in each case. All the mixing components mentioned, as the case may be, may also form salts with suitable bases or acids if they are capable of doing so on the basis of their functional groups.

Insecticides/acaricides/nematicides

The active ingredients specified here with their common names are known and are described for example in "The Pesticide Manual", 16th ed., British Crop Protection Council 2012, or can be searched for on the Internet (e.g. http://www.alanwood.net/pesticides). The classification is based on the IRAC Mode of Action Classification Scheme applicable at the time of filing of this patent application.

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, for example cyclodiene-organochlorines, e.g. chlordane and endosulfan or phenylpyrazoles (fiproles), e.g. ethiprole and fipronil.

(3) Sodium channel modulators, for example pyrethroids, e.g. acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomer], deltamethrin, empenthrin [(EZ)-(1R) isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans isomer], prallethrin, pyrethrins (pyrethrum), resmethrin, silafluofen, tefluthrin, tetramethrin, tetramethrin [(1R) isomer], tralomethrin and transfluthrin or DDT or methoxychlor.

(4) Nicotinic acetylcholine receptor (nAChR) competitive modulators, for example neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, for example spinosyns, e.g. spinetoram and spinosad.

(6) Glutamate-gated chloride channel (GluCl) allosteric modulators, for example avermectins/milbemycins, e.g. abamectin, emamectin benzoate, lepimectin and milbemectin.

(7) Juvenile hormone mimetics, for example juvenile hormone analogues, e.g. hydroprene, kinoprene and methoprene or fenoxycarb or pyriproxyfen.

(8) Miscellaneous non-specific (multisite) inhibitors, for example alkyl halides, e.g. methyl bromide and other alkyl halides; or chloropicrin or sulphuryl fluoride or borax or tartar emetic or methyl isocyanate generator, e.g. diazomet and metam.

(9) Chordotonal organ modulators, e.g. pymetrozine or flonicamide.

(10) Mite growth inhibitors, for example clofentezine, hexythiazox and diflovidazin or etoxazole.

(11) Microbial disruptors of the insect midgut membrane, for example *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis* and B.t. plant proteins: Cry1Ab, Cry1Ac, Cry1Fa, Cry1A.105, Cry2Ab, VIP3A, mCry3A, Cry3Ab, Cry3Bb, Cry34Ab1/35Ab1.

(12) Inhibitors of mitochondrial ATP synthase, such as ATP disruptors, for example diafenthiuron or organotin compounds, e.g. azocyclotin, cyhexatin and fenbutatin oxide or propargite or tetradifon.

(13) Uncouplers of oxidative phosphorylation via disruption of the proton gradient, for example chlorfenapyr, DNOC and sulfluramid.

(14) Nicotinic acetylcholine receptor channel blockers, for example bensultap, cartap hydrochloride, thiocyclam, and thiosultap-sodium.

(15) Inhibitors of chitin biosynthesis, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting disruptors (especially in the case of Diptera), for example cyromazine.

(18) Ecdysone receptor agonists, for example chromafenozide, halofenozide, methoxyfenozide and tebufenozide.

(19) Octopamine receptor agonists, for example amitraz.

(20) Mitochondrial complex III electron transport inhibitors, for example hydramethylnon or acequinocyl or fluacrypyrim.

(21) Mitochondrial complex I electron transport inhibitors, for example METI acaricides, e.g. fenazaquin, fenpyroximate, pyrimidifen, pyridaben, tebufenpyrad and tolfenpyrad or rotenone (Derris).

(22) Voltage-dependent sodium channel blockers, for example indoxacarb or metaflumizone.

(23) Inhibitors of acetyl CoA carboxylase, for example tetronic and tetramic acid derivatives, e.g. spirodiclofen, spiromesifen and spirotetramat.

(24) Mitochondrial complex IV electron transport inhibitors, for example phosphines, e.g. aluminium phosphide, calcium phosphide, phosphine and zinc phosphide, or cyanides, calcium cyanide, potassium cyanide and sodium cyanide.

(25) Mitochondrial complex II electron transport inhibitors, for example beta-keto nitrile derivatives, e.g. cyenopyrafen and cyflumetofen and carboxanilides, for example pyflubumide.

(28) Ryanodine receptor modulators, for example diamides, e.g. chlorantraniliprole, cyantraniliprole and flubendiamide, further active ingredients, for example afidopyropen, afoxolaner, azadirachtin, benclothiaz, benzoximate, bifenazate, broflanilide, bromopropylate, chinomethionat, chloroprallethrin, cryolite, cyclaniliprole, cycloxaprid, cyhalodiamide, dicloromezotiaz, dicofol, epsilon metofluthrin, epsilon momfluthrin, flometoquin, fluazaindolizine, fluensulfone, flufenerim, flufenoxystrobin, flufiprole, fluhexafon, fluopyram, fluralaner, fluxametamide, fufenozide, guadipyr, heptafluthrin, imidaclothiz, iprodione, kappa bifenthrin, kappa tefluthrin, lotilaner, meperfluthrin, paichongding, pyridalyl, pyrifluquinazon, pyriminostrobin, spirobudiclofen, tetramethylfluthrin, tetraniliprole, tetrachlorantraniliprole, tioxazafen, thiofluoximate, triflumezopyrim and iodomethane; additionally preparations based on *Bacillus firmus* (I-1582, BioNeem, Votivo), and the following compounds: 1-{2-fluoro-4-methyl-5-[(2,2,2-trifluoroethyl)sulphinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro [indole-3,4'-piperidine]-1(2H)-yl}(2-chloropyridin-4-yl) methanone (known from WO2003/106457) (CAS 637360-23-7), 2-chloro-N-[2-{1-[(2E)-3-(4-chlorophenyl)prop-2-en-1-yl]piperidin-4-yl}-4-(trifluoromethyl)phenyl] isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethylcarbonate (known from EP 2647626) (CAS-1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS Reg. No. 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoropropan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)benzamide, 4-[5-(3,5-dichlorophenyl)-4,5-dihydro-5-(trifluoromethyl)-3-isoxazolyl]-2-methyl-N-(trans-1-oxido-3-thietanyl)benzamide and 4-[(5S)-5-(3,5-dichlorophenyl)-4,5-dihydro-5-(trifluoromethyl)-3-isoxazolyl]-2-methyl-N-(cis-1-oxido-3-thietanyl)benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl)sulphinyl]propanamide, (+)-N-[3-chloro-1-(3-pyridinyl)-1H-pyrazol-4-yl]-N-ethyl-3-[(3,3,3-trifluoropropyl)sulphinyl]propanamide and (−)-N-[3-chloro-1-(3-pyridinyl)-1H-pyrazol-4-yl]-N-ethyl-3-[(3,3,3-trifluoropropyl)sulphinyl]propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl)sulphinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl)amino]carbonyl]-6-methylphenyl]-1-(3-chloro-2-pyridinyl)-3-(fluoromethoxy)-1H-pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl)pyrimidine (known from CN 101337940 A) (CAS 1108184-52-6); (2E)- and 2(Z)-2-[2-(4-cyanophenyl)-1-[3-(trifluoromethyl)phenyl]ethylidene]-N-[4-(difluoromethoxy)phenyl]hydrazinecarboxamide (known from CN 101715774 A) (CAS 1232543-85-9); cyclopropanecarboxylic acid 3-(2,2-dichloroethenyl)-2,2-dimethyl-4-(1H-benzimidazol-2-yl)phenyl ester (known from CN 103524422 A) (CAS 1542271-46-4); (4aS)-7-chloro-2,5-dihydro-2-[[(methoxycarbonyl) [4-[(trifluoromethyl)thio]phenyl]amino]carbonyl]indeno[1,2-e][1,3,4]oxadiazine-4a(3H)-carboxylic acid methyl ester (known from CN 102391261 A) (CAS 1370358-69-2); 6-deoxy-3-O-ethyl-2,4-di-O-methyl-1-[N-[4-[1-[4-(1,1,2,2,2-pentafluoroethoxy)phenyl]-1H-1,2,4-triazole-3-yl]phenyl]carbamate]-α-L-mannopyranose (known from US 2014/0275503 A1) (CAS 1181213-14-8); 8-(2-cyclopropylmethoxy-4-trifluoromethylphenoxy)-3-(6-trifluoromethylpyridazin-3-yl)-3-azabicyclo[3.2.1]octane (CAS 1253850-56-4), (8-anti)-8-(2-cyclopropylmethoxy-4-trifluoromethylphenoxy)-3-(6-trifluoromethylpyridazin-3-yl)-3-azabicyclo[3.2.1]octane (CAS 933798-27-7), (8-syn)-8-(2-cyclopropylmethoxy-4-trifluoromethylphenoxy)-3-(6-trifluoromethylpyridazin-3-yl)-3-azabicyclo[3.2.1]octane (known from WO 2007040280 A1, WO 2007040282 A1) (CAS 934001-66-8) and N-[3-chloro-1-(3-pyridinyl)-1H-pyrazol-4-yl]-N-ethyl-3-[(3,3,3-trifluoropropyl)thio]propanamide (known from WO 2015/058021 A1, WO 2015/058028 A1) (CAS 1477919-27-9).

Fungicides

The active compounds specified herein by their common name are known and described, for example, in "Pesticide Manual" (16th Ed. British Crop Protection Council) or searchable on the internet (for example: http://www.alanwood.net/pesticides).

All the mixing components mentioned in classes (1) to (15), as the case may be, may form salts with suitable bases or acids if they are capable of doing so on the basis of their functional groups. All the fungicidal mixing components mentioned of classes (1) to (15), as the case may be, may include tautomeric forms.

1) Ergosterol biosynthesis inhibitors, for example (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulphate, (1.012) ipconazole, (1.013) metconazole, (1.014) myclobutanil, (1.015) paclobutrazol, (1.016) prochloraz, (1.017) propiconazole, (1.018) prothioconazole, (1.019) pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-difluorophenyl)-1,2-oxazol-4-yl](pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)-2-(2,4-difluorophenyl)oxiran-2-yl]methyl}-1H-1,2,4-triazol-5-yl thiocyanate, (1.041) 1-{[rel(2R,3S)-3-(2-chlorophenyl)-2-(2,4-difluorophenyl)oxiran-2-yl]methyl J}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3- thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) 2-[4-(4-chlorophenoxy)-2-(trifluoromethyl)phenyl]-1-(1H-1,2,4-triazol-1-yl)propan-2-ol, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulphanyl)-1-{[3-(2-chlorophenyl)-2-(2,4-difluorophenyl)oxiran-2-yl]methyl}-1H-1,2,4-triazole, (1.061) 5-(allylsulphanyl)-1-{[rel(2R,3R)-3-(2-chlorophenyl)-2-(2,4-difluorophenyl)oxiran-2-yl]methyl}-1H-1,2,4-triazole, (1.062) 5-(allylsulphanyl)-1-{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulphanyl}phenyl)-N-ethyl-N-methylimidoformamide, (1.064) N'-(2,5-dimethyl-4-{[3-(2,2,2-trifluoroethoxy)phenyl]sulphanyl}phenyl)-N-ethyl-N-methylimidoformamide, (1.065) N'-(2,5-dimethyl-4-{[3-(2,2,3,3-tetrafluoropropoxy)phenyl]sulphanyl}phenyl)-N-ethyl-N-methylimidoformamide, (1.066) N'-(2,5-dimethyl-4-{[3-(pentafluoroethoxy)phenyl]sulphanyl}phenyl)-N-ethyl-N-methylimidoformamide, (1.067) N'-(2,5-dimethyl-4-{3-[(1,1,2,2-tetrafluoroethyl)sulphanyl]phenoxy}phenyl)-N-ethyl-N-methylimidoformamide, (1.068) N'-(2,5-dimethyl-4-{3-[(2,2,2-trifluoroethyl)sulphanyl]phenoxy}phenyl)-N-ethyl-N-methylimidoformamide, (1.069) N'-(2,5-dimethyl-4-{3-[(2,2,3,3-tetrafluoropropyl)sulphanyl]phenoxy}phenyl)-N-ethyl-N-methylimidoformamide, (1.070) N'-(2,5-dimethyl-4-{3-[(pentafluoroethyl)sulphanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulphanyl}-2,5-dimethylphenyl)-N-ethyl-N-methylimidoformamide, (1.073) N'-(4-{3-[(difluoromethyl)sulphanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-[(1S)-1-(3,5-difluorophenyl)ethoxy]-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide.

2) Inhibitors of the respiratory chain in complex I or II, for example (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of the syn-epimeric racemate 1RS,4SR,9RS and the anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3S)-1,1,3-trimethyl-2,3-dihydro-1H-inden-4-yl]-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro- 2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-H-pyrazole-4-carboxamide, (2.056) N-cyclopropyl-N-(2-cyclopropylbenzyl)-3-(difluoromethyl)-5-fluoro-1-methyl-1H-pyrazole-4-carboxamide.

3) Inhibitors of the respiratory chain in complex III, for example (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadon, (3.010) fenamidon, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-{2-[(2,5-dimethylphenoxy)methyl]phenyl}-2-methoxy-N-methylacetamide, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methylacetamide, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide.

4) Mitosis and cell division inhibitors, for example (4.001) carbendazim, (4.002) diethofencarb, (4.003) ethaboxam, (4.004) fluopicolid, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine.

5) Compounds having capacity for multisite activity, for example (5.001) Bordeaux mixture, (5.002) captafol, (5.003) captan, (5.004) chlorthalonil, (5.005) copper hydroxide (5.006) copper naphthenate, (5.007) copper oxide, (5.008) copper oxychloride, (5.009) copper(2+) sulphate, (5.010) dithianon, (5.011) dodin, (5.012) folpet, (5.013) mancozeb, (5.014) maneb, (5.015) metiram, (5.016) zinc metiram, (5.017) copper oxine, (5.018) propineb, (5.019) sulphur and sulphur preparations including calcium polysulphide, (5.020) thiram, (5.021) zineb, (5.022) ziram.

6) Compounds capable of triggering host defence, for example (6.001) acibenzolar-S-methyl, (6.002) isotianil, (6.003) probenazole, (6.004) tiadinil.

7) Amino acid and/or protein biosynthesis inhibitors, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinoline.

(8) ATP production inhibitors, for example (8.001) silthiofam.

9) Cell wall synthesis inhibitors, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, (9.009) (2Z)-3-(4-tert-butylphenyl)-3-(2-chloropyridin-4-yl)-1-(morpholin-4-yl)prop-2-en-1-one.

10) Lipid and membrane synthesis inhibitors, for example (10.001) propamocarb, (10.002) propamocarb hydrochloride, (10.003) tolclofos-methyl.

11) Melanin biosynthesis inhibitors, for example (11.001) tricyclazole, (11.002) 2,2,2-trifluoroethyl {3-methyl-1-[(4-methylbenzoyl)amino]butan-2-yl}carbamate.

12) Nucleic acid synthesis inhibitors, for example (12.001) benalaxyl, (12.002) benalaxyl-M (kiralaxyl), (12.003) metalaxyl, (12.004) metalaxyl-M (mefenoxam).

13) Signal transduction inhibitors, for example (13.001) fludioxonil, (13.002) iprodione, (13.003) procymidone, (13.004) proquinazid, (13.005) quinoxyfen, (13.006) vinclozolin.

14) Compounds that can act as uncouplers, for example (14.001) fluazinam, (14.002) meptyldinocap.

15) Further compounds, for example (15.001) abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenon, (15.017) mildiomycin, (15.018) natamycin, (15.019) nickel dimethyldithiocarbamate, (15.020) nitrothal-isopropyl, (15.021) oxamocarb, (15.022) oxathiapiprolin, (15.023) oxyfenthiin, (15.024) pentachlorophenol and salts, (15.025) phosphonic acid and salts thereof, (15.026) propamocarb-fosetylate, (15.027) pyriofenone (chlazafenone) (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.033) 2-(6-benzylpyridin-2-yl)quinazoline, (15.034) 2,6-dimethyl-1H,5H-[1,4]dithiino[2,3-c:5,6-c']dipyrrole-1,3,5,7(2H,6H)-tetrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl]quinazoline, (15.039) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulphonate, (15.040) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulphonate, (15.041) 2-{2-[(7,8-difluoro-2-methylquinolin-3-yl)oxy]-6-fluorophenyl}propan-2-ol, (15.042) 2-{2-fluoro-6-[(8-fluoro-2-methylquinolin-3-yl)oxy]phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulphonate, (15.044) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulphonate, (15.045) 2-phenylphenol and salts thereof, (15.046) 3-(4,4,5-trifluoro-3,3-dimethyl-3,4-dihydroisoquinolin-1-yl)quinoline, (15.047) 3-(4,4-difluoro-3,3-dimethyl-3,4-dihydroisoquinolin-1-yl)quinoline, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butyric acid, (15.050) 5-amino-1,3,4-thiadiazole-2-thiol, (15.051) 5-chloro-N'-phenyl-N'-(prop-2-yn-1-yl)thiophene 2-sulphonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulphate (2:1), (15.061) tert-butyl {6-[({[(1-methyl-1H-tetrazol-5-yl) (phenyl)methylene]amino}oxy)methyl]pyridin-2-yl}carbamate.

Biological Pesticides as Mixing Components

The compounds of the formula (I) can be combined with biological pesticides.

Biological pesticides especially include bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, especially *B. cereus* strain CNCM I-1562 or *Bacillus firmus*, strain I-1582 (Accession number CNCM I-1582) or *Bacillus pumilus*, especially strain GB34 (Accession No. ATCC 700814) and strain QST2808 (Accession No. NRRL B-30087), or *Bacillus subtilis*, especially strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, especially *B. thuringiensis* subspecies *israelensis* (serotype H-14), strain AM65-52 (Accession No. ATCC 1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans*, *Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii*, (formerly known as *Verticillium lecanii*), in particular strain KVO1, *Metarhizium anisopliae*, in particular strain F52 (DSM3884/ATCC 90448), *Metschnikowia fructicola*, in particular strain NRRL Y-30752, *Paecilomyces fumosoroseus* (new: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum* rifai T39 (Accession Number CNCM I-952).

Examples of viruses which are used or can be used as biological pesticides are:

*Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include:

*Agrobacterium* spp., *Azorhizobium caulinodans*, *Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum*, *Glomus* spp., *Laccaria* spp., *Lactobacillus buchneri*, *Paraglomus* spp., *Pisolithus tinctorus*,

*Pseudomonas* spp., *Rhizobium* spp., especially *Rhizobium trifolii*, *Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:

*Allium sativum, Artemisia absinthium*, azadirachtin, Biokeeper WP, *Cassia nigricans, Celastrus angulatus, Chenopodium anthelminticum*, chitin, Armour-Zen, *Dryopteris filix-mas, Equisetum arvense*, Fortune Aza, Fungastop, Heads Up (*Chenopodium quinoa* saponin extract), pyrethrum/pyrethrins, *Quassia amara, Quercus, Quillaja, Regalia*, "Requiem™ Insecticide", rotenone, ryania/ryanodine, *Symphytum officinale, Tanacetum vulgare*, thymol, Triact 70, TriCon, *Tropaeulum majus, Urtica dioica*, Veratrin, *Viscum album*, Brassicaceae extract, especially oilseed rape powder or mustard powder.

Safeners as Mixing Components

The compounds of the formula (I) can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya beans, potatoes, sugar beet, sugar cane, tomatoes, bell peppers, cucumbers, melons, carrots, water melons, onions, lettuce, spinach, leeks, beans, *Brassica oleracea* (e.g. cabbage) and other vegetable species, cotton, tobacco, oilseed rape, and also fruit plants (the fruits being apples, pears, citrus fruits and grapes). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plants shall be understood to mean all development stages such as seed, seedlings, young (immature) plants, up to and including mature plants. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested plants or harvested plant parts and vegetative and generative propagation material, for example cuttings, tubers, rhizomes, slips and seeds.

The treatment according to the invention of the plants and parts of plants with the compounds of the formula (I) is effected directly or by allowing the compounds to act on the surroundings, the habitat or the storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and their parts in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") and which have been obtained by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better storage life and/or processability of the harvested products. Further and particularly emphasized examples of such properties are increased resistance of the plants against animal and microbial pests, such as insects, arachnids, nematodes, mites, slugs and snails, owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof), and also increased resistance of the plants against phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain herbicidally active compounds, for example imidazolinones, sulphonylureas, glyphosate or phosphinothricin (for example the "PAT" gene). The genes which impart the desired properties ("traits") in question may also be present in combinations with one another in the transgenic plants. Examples of transgenic plants mentioned include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (the fruits being apples, pears, citrus fruits and grapevines), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The plants and plant parts are treated with the compounds of the formula (I) directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, meaning that the compounds of the formula (I) are applied to the foliage, in which case the treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) according to the invention are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. Nevertheless, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active ingredient used so as to provide optimum protection for the seed and the germinating plant from attack by animal pests, but without damage to the plant itself by the active ingredient used. In particular, methods for the treatment of seed should also take account of the intrinsic insecticidal or nematicidal properties of pest-resistant or -tolerant transgenic plants in order to achieve optimal protection of the seed and also the germinating plant with a minimum expenditure on pesticides.

The present invention therefore in particular also relates to a method for the protection of seed and germinating plants from attack by pests, by treating the seed with one of the compounds of the formula (I). The method according to the invention for protecting seed and germinating plants against attack by pests further comprises a method in which the seed is treated simultaneously in one operation or sequentially with a compound of the formula (I) and a mixing component. It further also comprises a method where the seed is treated at different times with a compound of the formula (I) and a mixing component.

The invention likewise relates to the use of the compounds of the formula (I) for the treatment of seed for protecting the seed and the resulting plant from animal pests.

The invention further relates to seed which has been treated with a compound of the formula (I) according to the invention for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and mixing components may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages that occur when a compound of the formula (I) acts systemically is that the treatment of the seed protects not only the seed itself but also the plants resulting therefrom, after emergence, from animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Furthermore, compounds of the formula (I) can be employed in combination with compositions of signalling technology, leading to better colonization by symbionts such as, for example, *rhizobia*, mycorrhizae and/or endophytic bacteria or fungi, and/or to optimized nitrogen fixation.

The compounds of the formula (I) are suitable for protection of seed of any plant variety which is used in agriculture, in the greenhouse, in forests or in horticulture. More particularly, this is the seed of cereals (for example wheat, barley, rye, millet and oats), maize, cotton, soya beans, rice, potatoes, sunflowers, coffee, tobacco, canola, oilseed rape, beets (for example sugar beets and fodder beets), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape, vegetables and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate from microorganisms such as *Bacillus, Rhizobium, Pseudomonas, Serratia, Trichoderma, Clavibacter, Glomus* or *Gliocladium*. The present invention is particularly suitable for treatment of transgenic seed which comprises at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been soaked, for example in water, until it reaches a certain stage of the rice embryo ("pigeon breast stage") which results in stimulation of germination and more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active ingredients which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed-dressing formulations, such as solutions, emulsions, suspensions, powders, foams, slurries or other coating compositions for seed, and also ULV formulations.

These formulations are prepared in a known manner, by mixing the compounds of the formula (I) with customary additives, for example customary extenders and solvents or diluents, dyes, wetting agents, dispersants, emulsifiers, antifoams, preservatives, secondary thickeners, adhesives, gibberellins, and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of active agrochemical ingredients. Usable with preference are alkyl naphthalenesulphonates, such as diisopropyl or diisobutyl naphthalenesulphonates.

Suitable dispersants and/or emulsifiers which may be present in the seed-dressing formulations usable in accordance with the invention are all nonionic, anionic and cationic dispersants customary for the formulation of active agrochemical ingredients. Nonionic or anionic dispersants or mixtures of nonionic or anionic dispersants can be used with preference. Suitable nonionic dispersants especially include ethylene oxide/propylene oxide block polymers, alkylphenol polyglycol ethers and tristyrylphenol polyglycol ethers, and the phosphated or sulphated derivatives thereof. Suitable anionic dispersants are especially lignosulphonates, polyacrylic acid salts and arylsulphonate-formaldehyde condensates.

Antifoams which may be present in the seed-dressing formulations usable in accordance with the invention are all foam-inhibiting substances customary for the formulation of active agrochemical ingredients. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions.

Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute use forms thereof, can also be used to dress seed of transgenic plants.

For the treatment of seed with the seed-dressing formulations usable in accordance with the invention, or the use forms prepared therefrom through the addition of water, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed-dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term "endoparasite" includes especially helminths and protozoa, such as coccidia. Ectoparasites are typically and preferably arthropods, especially insects or acarids.

In the field of veterinary medicine, the compounds of the formula (I) having favourable endotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals, such as sheep, goats, horses, donkeys, camels, buffalo, rabbits, reindeer, fallow deer and especially cattle and pigs; or poultry such as turkeys, ducks, geese and especially chickens; or fish or crustaceans, for example in aquaculture; or, as the case may be, insects such as bees.

Domestic animals include, for example, mammals, such as hamsters, guinea pigs, rats, mice, chinchillas, ferrets, and particularly dogs, cats, caged birds; reptiles, amphibians or aquarium fish.

In a specific embodiment, the compounds of the formula (I) are administered to mammals.

In another specific embodiment, the compounds of the formula (I) are administered to birds, namely caged birds or particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal husbandry is enabled and better animal well-being is achievable.

In relation to the field of animal health, the term "control" or "controlling" in the present context means that the compounds of the formula (I) are effective in reducing the incidence of the particular parasite in an animal infected with such parasites to an innocuous degree. More specifically, "controlling" in the present context means that the compounds of the formula (I) kill the respective parasite, inhibit its growth, or inhibit its proliferation.

The arthropods include, for example, but are not limited to, from the order of Anoplurida, for example, *Haematopinus* spp., *Linognathus* spp., *Pediculus* spp., *Phtirus* spp. and *Solenopotes* spp.;

from the order of Mallophagida and the suborders Amblycerina and Ischnocerina, for example, *Bovicola* spp., *Damalina* spp., *Felicola* spp.; *Lepikentron* spp., *Menopon* spp., *Trichodectes* spp., *Trimenopon* spp., *Trinoton* spp., *Werneckiella* spp;

from the order of Diptera and the suborders Nematocerina and Brachycerina, for example, *Aedes* spp., *Anopheles* spp., *Atylotus* spp., *Braula* spp., *Calliphora* spp., *Chrysomyia* spp., *Chrysops* spp., *Culex* spp., *Culicoides* spp., *Eusimulium* spp., *Fannia* spp., *Gasterophilus* spp., *Glossina* spp., *Haematobia* spp., *Haematopota* spp., *Hippobosca* spp., *Hybomitra* spp., *Hydrotaea* spp., *Hypoderma* spp., *Lipoptena* spp., *Lucilia* spp., *Lutzomyia* spp., *Melophagus* spp., *Morellia* spp., *Musca* spp., *Odagmia* spp., *Oestrus* spp., *Philipomyia* spp., *Phlebotomus* spp., *Rhinoestrus* spp., *Sarcophaga* spp., *Simulium* spp., *Stomoxys* spp., *Tabanus* spp., *Tipula* spp., *Wilhelmia* spp., *Wohlfahrtia* spp.;

from the order of Siphonapterida, for example, *Ceratophyllus* spp., *Ctenocephalides* spp., *Pulex* spp., *Tunga* spp., *Xenopsylla* spp.;

from the order of Heteropterida, for example, *Cimex* spp., *Panstrongylus* spp., *Rhodnius* spp., *Triatoma* spp.; and also nuisance and hygiene pests from the order Blattarida.

In addition, in the case of the arthropods, mention should be made by way of example, without limitation, of the following Acari:

from the subclass of Acari (Acarina) and the order of Metastigmata, for example from the family of Argasidae such as *Argas* spp., *Ornithodorus* spp., *Otobius* spp., from the family of Ixodidae such as *Amblyomma* spp., *Dermacentor* spp., *Haemaphysalis* spp., *Hyalomma* spp., *Ixodes* spp., *Rhipicephalus* (*Boophilus*) *spp.*, *Rhipicephalus* spp. (the original genus of multi-host ticks); from the order of Mesostigmata such as *Dermanyssus* spp., *Ornithonyssus* spp., *Pneumonyssus* spp., *Raillietia* spp., *Sternostoma* spp., *Tropilaelaps* spp., *Varroa* spp.; from the order of the Actinedida (Prostigmata), for example, *Acarapis* spp., *Cheyle-* *tiella* spp., *Demodex* spp., *Listrophorus* spp., *Myobia* spp., *Neotrombicula* spp., *Ornithocheyletia* spp., *Psorergates* spp., *Trombicula* spp.; and from the order of the Acaridida (Astigmata), for example, *Acarus* spp., *Caloglyphus* spp., *Chorioptes* spp., *Cytodites* spp., *Hypodectes* spp., *Knemidocoptes* spp., *Laminosioptes* spp., *Notoedres* spp., *Otodectes* spp., *Psoroptes* spp., *Pterolichus* spp., *Sarcoptes* spp., *Trixacarus* spp., *Tyrophagus* spp.

Examples of parasitic protozoa include, but are not limited to:

Mastigophora (Flagellata), such as:

Metamonada: from the order of Diplomonadida, for example, *Giardia* spp., *Spironucleus* spp. Parabasala: from the order of Trichomonadida, for example, *Histomonas* spp., *Pentatrichomonas* spp., *Tetratrichomonas* spp., *Trichomonas* spp., *Tritrichomonas* spp.

Euglenozoa: from the order of Trypanosomatida, for example, *Leishmania* spp., *Trypanosoma* spp.

Sarcomastigophora (Rhizopoda) such as Entamoebidae, for example, *Entamoeba* spp., *Centramoebidae, for example Acanthamoeba* sp., *Euamoebidae*, e.g. *Hartmanella* sp.

Alveolata such as Apicomplexa (Sporozoa): e.g. *Cryptosporidium* spp.; from the order of Eimeriida, for example, *Besnoitia* spp., *Cystoisospora* spp., *Eimeria* spp., *Hammondia* spp., *Isospora* spp., *Neospora* spp., *Sarcocystis* spp., *Toxoplasma* spp.; from the order of Adeleida, for example, *Hepatozoon* spp., *Klossiella* spp.; from the order of Haemosporida, for example, *Leucocytozoon* spp., *Plasmodium* spp.; from the order of Piroplasmida, for example, *Babesia* spp., *Ciliophora* spp., *Echinozoon* spp., *Theileria* spp.; from the order of Vesibuliferida, for example, *Balantidium* spp., *Buxtonella* spp.

Microspora such as *Encephalitozoon* spp., *Enterocytozoon* spp., *Globidium* spp., *Nosema* spp., and also, for example, *Myxozoa* spp.

The helminths that are pathogenic to humans or animals include, for example, Acanthocephala, Nematoden, Pentastoma and Platyhelminthes (e.g. Monogenea, cestodes and trematodes).

Illustrative helminths include, but are not limited to:

Monogenea: for example: *Dactylogyrus* spp., *Gyrodactylus* spp., *Microbothrium* spp., *Polystoma* spp., *Troglecephalus* spp.

Cestodes: from the order of Pseudophyllidea, for example: *Bothridium* spp., *Diphyllobothrium* spp., *Diplogonoporus* spp., *Ichthyobothrium* spp., *Ligula* spp., *Schistocephalus* spp., *Spirometra* spp.

From the order of Cyclophyllida, for example: *Andyra* spp., *Anoplocephala* spp., *Avitellina* spp., *Bertiella* spp., *Cittotaenia* spp., *Davainea* spp., *Diorchis* spp., *Diplopylidium* spp., *Dipylidium* spp., *Echinococcus* spp., *Echinocotyle* spp., *Echinolepis* spp., *Hydatigera* spp., *Hymenolepis* spp., *Joyeuxiella* spp., *Mesocestoides* spp., *Moniezia* spp., *Paranoplocephala* spp., *Raillietina* spp., *Stilesia* spp., *Taenia* spp., *Thysaniezia* spp., *Thysanosoma* spp.

Trematodes: from the class of Digenea, for example: *Austrobilharzia* spp., *Brachylaima* spp., *Calicophoron* spp., *Catatropis* spp., *Clonorchis* spp. *Collyriclum* spp., *Cotylophoron* spp., *Cyclocoelum* spp., *Dicrocoelium* spp., *Diplostomum* spp., *Echinochasmus* spp., *Echinoparyphium* spp., *Echinostoma* spp., *Eurytrema* spp., *Fasciola* spp., *Fasciolides* spp., *Fasciolopsis* spp., *Fischoederius* spp., *Gastrothylacus* spp., *Gigantobilharzia* spp., *Gigantocotyle* spp., *Heterophyes* spp., *Hypoderaeum* spp., *Leucochloridium* spp., *Metagonimus* spp., *Metorchis* spp., *Nanophyetus* spp., *Notocotylus* spp., *Opisthorchis* spp., *Ornithobilharzia* spp., *Paragonimus* spp., *Paramphistomum* spp., *Plagiorchis* spp.,

*Posthodiplostomum* spp., *Prosthogonimus* spp., *Schistosoma* spp., *Trichobilharzia* spp., *Troglotrema* spp., *Typhlocoelum* spp.

Nematodes: from the order of Trichinellida, for example: *Capillaria* spp., *Trichinella* spp., *Trichomosoides* spp., *Trichuris* spp.

From the order of Tylenchida, for example: *Micronema* spp., *Parastrangyloides* spp., *Strongyloides* spp.

From the order of Rhabditina, for example: *Aelurostrongylus* spp., *Amidostomum* spp., *Ancylostoma* spp., *Angiostrongylus* spp., *Bronchonema* spp., *Bunostomum* spp., *Chabertia* spp., *Cooperia* spp., *Cooperioides* spp., *Crenosoma* spp., *Cyathostomum* spp., *Cyclococercus* spp., *Cyclodontostomum* spp., *Cylicocyclus* spp., *Cylicostephanus* spp., *Cylindropharynx* spp., *Cystocaulus* spp., *Dictyocaulus* spp., *Elaphostrongylus* spp., *Filaroides* spp., *Globocephalus* spp., *Graphidium* spp., *Gyalocephalus* spp., *Haemonchus* spp., *Heligmosomoides* spp., *Hyostrongylus* spp., *Marshallagia* spp., *Metastrongylus* spp., *Muellerius* spp., *Necator* spp., *Nematodirus* spp., *Neostrongylus* spp., *Nippostrongylus* spp., *Obeliscoides* spp., *Oesophagodontus* spp., *Oesophagostomum* spp., *Ollulanus* spp.; *Ornithostrongylus* spp., *Oslerus* spp., *Ostertagia* spp., *Paracooperia* spp., *Paracrenosoma* spp., *Parafilaroides* spp., *Parelaphostrongylus* spp., *Pneumocaulus* spp., *Pneumostrongylus* spp., *Poteriostomum* spp., *Protostrongylus* spp., *Spicocaulus* spp., *Stephanurus* spp., *Strongylus* spp., *Syngamus* spp., *Teladorsagia* spp., *Trichonema* spp., *Trichostrongylus* spp., *Triodontophorus* spp., *Troglostrongylus* spp., *Uncinaria* spp.

From the order of Spirurida, for example: *Acanthocheilonema* spp., *Anisakis* spp., *Ascaridia* spp.; *Ascaris* spp., *Ascarops* spp., *Aspiculuris* spp., *Baylisascaris* spp., *Brugia* spp., *Cercopithifilaria* spp., *Crassicauda* spp., *Dipetalonema* spp., *Dirofilaria* spp., *Dracunculus* spp.; *Draschia* spp., *Enterobius* spp., *Filaria* spp., *Gnathostoma* spp., *Gongylonema* spp., *Habronema* spp., *Heterakis* spp.; *Litomosoides* spp., *Loa* spp., *Onchocerca* spp., *Oxyuris* spp., *Parabronema* spp., *Parafilaria* spp., *Parascaris* spp., *Passalurus* spp., *Physaloptera* spp., *Probstmayria* spp., *Pseudofilaria* spp., *Setaria* spp., *Skjrabinema* spp., *Spirocerca* spp., *Stephanofilaria* spp., *Strongyluris* spp., *Syphacia* spp., *Thelazia* spp., *Toxascaris* spp., *Toxocara* spp., *Wuchereria* spp.

Acanthocephala: from the order of Oligacanthorhynchida, for example: *Macracanthorhynchus* spp., *Prosthenorchis* spp.; from the order of Moniliformida, for example: *Moniliformis* spp.

From the order of Polymorphida, for example: *Filicollis* spp.; from the order of Echinorhynchida, for example *Acanthocephalus* spp., *Echinorhynchus* spp., *Leptorhynchoides* spp.

Pentastoma: from the order of Porocephalida, for example, *Linguatula* spp.

In the veterinary field and in animal husbandry, the compounds of the formula (I) are administered by methods generally known in the art, such as via the enteral, parenteral, dermal or nasal route in the form of suitable preparations. Administration may be prophylactic, metaphylactic or therapeutic.

Thus, one embodiment of the present invention refers to the compounds of the formula (I) for use as a medicament.

A further aspect relates to the compounds of the formula (I) for use as an antiendoparasitic agent. A further specific aspect of the invention relates to the compounds of the formula (I) for use as an antithelminthic agent, especially for use as a nematicide, platyxelminthicide, acanthocephalicide or pentastomicide.

A further specific aspect of the invention relates to the compounds of the formula (I) for use as an antiprotozoic agent.

A further aspect relates to the compounds of the formula (I) for use as an antiectoparasitic agent, especially an arthropodicide, very particularly an insecticide or an acaricide.

Further aspects of the invention are veterinary medicine formulations comprising an effective amount of at least one compound of the formula (I) and at least one of the following: a pharmaceutically acceptable excipient (e.g. solid or liquid diluents), a pharmaceutically acceptable auxiliary (e.g. surfactants), especially a pharmaceutically acceptable excipient used conventionally in veterinary medicine formulations and/or a pharmaceutically acceptable auxiliary conventionally used in veterinary medicine formulations.

A related aspect of the invention is a method for production of a veterinary medicine formulation as described here, which comprises the step of mixing at least one compound of the formula (I) with pharmaceutically acceptable excipients and/or auxiliaries, especially with pharmaceutically acceptable excipients used conventionally in veterinary medicine formulations and/or auxiliaries used conventionally in veterinary medicine formulations.

Another specific aspect of the invention is veterinary medicine formulations selected from the group of ectoparasiticidal and endoparasiticidal formulations, especially selected from the group of anthelmintic, antiprotozoic and arthropodicidal formulations, very particularly selected from the group of nematicidal, platyhelminthicidal, acanthocephalidicidal, pentastomicidal, insecticidal and acaricidal formulations, according to the aspects mentioned, and methods for production thereof.

Another aspect relates to a method for treatment of a parasitic infection, especially an infection caused by a parasite selected from the group of the ectoparasites and endoparasites mentioned here, by use of an effective amount of a compound of the formula (I) in an animal, especially a nonhuman animal, having a need therefor.

Another aspect relates to a method for treatment of a parasitic infection, especially an infection caused by a parasite selected from the group of the ectoparasites and endoparasites mentioned here, by use of a veterinary medicine formulation as defined here in an animal, especially a nonhuman animal, having a need therefor.

Another aspect relates to the use of the compounds of the formula (I) in the treatment of a parasite infection, especially an infection caused by a parasite selected from the group of the ectoparasites and endoparasites mentioned here, in an animal, especially a nonhuman animal.

In the present context of animal health or veterinary medicine, the term "treatment" includes prophylactic, metaphylactic and therapeutic treatment.

In a particular embodiment, in this way, mixtures of at least one compound of the formula (I) with other active compounds, especially with endo- and ectoparasiticides, are provided for the field of veterinary medicine.

In the field of animal health, "mixture" means not just that two (or more) different active ingredients are formulated in a common formulation and are correspondingly employed together, but also relates to products comprising formulations separated for each active ingredient. Accordingly, when more than two active ingredients are to be employed, all active ingredients can be formulated in a common formulation or all active ingredients can be formulated in separate formulations; likewise conceivable are mixed forms in which some of the active ingredients are formulated together and some of the active ingredients are formulated separately. Separate formulations allow the separate or successive application of the active ingredients in question.

The active compounds specified here by their "common names" are known and are described, for example, in the "Pesticide Manual" (see above) or can be searched for on the Internet (e.g.: http://www.alanwood.net/pesticides).

Illustrative active ingredients from the group of the ectoparasiticides as mixing components, without any intention that this should constitute a restriction, include the insecticides and acaricides listed in detail above. Further usable active ingredients are listed below in accordance with the abovementioned classification based on the current IRAC Mode of Action Classification Scheme: (1) acetylcholinesterase (AChE) inhibitors; (2) GABA-gated chloride channel blockers; (3) sodium channel modulators; (4) nicotinic acetylcholine receptor (nAChR) competitive modulators; (5) nicotinic acetylcholine receptor (nAChR) allosteric modulators; (6) glutamate-gated chloride channel (GluCl) allosteric modulators; (7) juvenile hormone mimetics; (8) miscellaneous non-specific (multi-site) inhibitors; (9) chordotonal organ modulators; (10) mite growth inhibitors; (12) inhibitors of mitochondrial ATP synthase, such as ATP disruptors; (13) uncouplers of oxidative phosphorylation via disruption of the proton gradient; (14) nicotinic acetylcholine receptor channel blockers; (15) inhibitors of chitin biosynthesis, type 0; (16) inhibitors of chitin biosynthesis, type 1; (17) moulting disruptors (especially in Diptera); (18) ecdysone receptor agonists; (19) octopamine receptor agonists; (21) mitochondrial complex I electron transport inhibitors; (25) mitochondrial complex II electron transport inhibitors; (20) mitochondrial complex III electron transport inhibitors; (22) voltage-dependent sodium channel blockers; (23) inhibitors of acetyl CoA carboxylase; (28) ryanodine receptor modulators;

active ingredients having unknown or non-specific mechanisms of action, e.g. fentrifanil, fenoxacrim, cycloprene, chlorobenzilate, chlordimeform, flubenzimin, dicyclanil, amidoflumet, quinomethionat, triarathene, clothiazoben, tetrasul, potassium oleate, petroleum, metoxadiazone, gossyplur, flutenzine, brompropylate, cryolite;

compounds from other classes, for example butacarb, dimetilan, cloethocarb, phosphocarb, pirimiphos(-ethyl), parathion(-ethyl), methacrifos, isopropyl o-salicylate, trichlorfon, sulprofos, propaphos, sebufos, pyridathion, prothoate, dichlofenthion, demeton-S-methyl sulphone, isazofos, cyanofenphos, dialifos, carbophenothion, autathiofos, aromfenvinfos(-methyl), azinphos(-ethyl), chlorpyrifos(-ethyl), fosmethilan, iodofenphos, dioxabenzofos, formothion, fonofos, flupyrazofos, fensulfothion, etrimfos; organochlorine compounds, for example camphechlor, lindane, heptachlor; or phenylpyrazoles, e.g. acetoprole, pyrafluprole, pyriprole, vaniliprole, sisapronil; or isoxazolines, e.g. sarolaner, afoxolaner, lotilaner, fluralaner;

pyrethroids, e.g. (cis-, trans-)metofluthrin, profluthrin, flufenprox, flubrocythrinate, fubfenprox, fenfluthrin, protrifenbut, pyresmethrin, RU15525, terallethrin, cis-resmethrin, heptafluthrin, bioethanomethrin, biopermethrin, fenpyrithrin, cis-cypermethrin, cis-permethrin, clocythrin, cyhalothrin (lambda-), chlovaporthrin, or halogenated hydrocarbon compounds (HCHs), neonicotinoids, e.g. nithiazine dicloromezotiaz, triflumezopyrim macrocyclic lactones, e.g. nemadectin, ivermectin, latidectin, moxidectin, selamectin, eprinomectin, doramectin, emamectin benzoate; milbemycin oxime triprene, epofenonane, diofenolan;

biologicals, hormones or pheromones, for example natural products, e.g. thuringiensin, codlemone or neem components dinitrophenols, e.g. dinocap, dinobuton, binapacryl;

benzoylureas, e.g. fluazuron, penfluron, amidine derivatives, e.g. chlormebuform, cymiazole, demiditraz beehive *varroa* acaricides, for example organic acids, e.g. formic acid, oxalic acid.

Illustrative active ingredients from the group of the endoparasiticides, as mixing components, include, but are not limited to, active anthelmintic ingredients and active antiprotozoic ingredients.

The anthelmintically active compounds include but are not limited to the following nematicidally, trematicidally and/or cestocidally active compounds:

from the class of the macrocyclic lactones, for example: eprinomectin, abamectin, nemadectin, moxidectin, doramectin, selamectin, lepimectin, latidectin, milbemectin, ivermectin, emamectin, milbemycin;

from the class of the benzimidazoles and probenzimidazoles, for example: oxibendazole, mebendazole, triclabendazole, thiophanate, parbendazole, oxfendazole, netobimin, fenbendazole, febantel, thiabendazole, cyclobendazole, cambendazole, albendazole sulfoxide, albendazole, flubendazole;

from the class of the depsipeptides, preferably cyclic depsipetides, especially 24-membered cyclic depsipeptides, for example: emodepside, PF1022A;

from the class of the tetrahydropyrimidines, for example: morantel, pyrantel, oxantel;

from the class of the imidazothiazoles, for example: butamisole, levamisole, tetramisole;

from the class of the aminophenylamidines, for example: amidantel, deacylated amidantel (dAMD), tribendimidine;

from the class of the aminoacetonitriles, for example: monepantel;

from the class of the paraherquamides, for example: paraherquamide, derquantel;

from the class of the salicylanilides, for example: tribromsalan, bromoxanide, brotianide, clioxanide, closantel, niclosamide, oxyclozanide, rafoxanide;

from the class of the substituted phenols, for example: nitroxynil, bithionol, disophenol, hexachlorophen, niclofolan, meniclopholan;

from the class of the organophosphates, for example: trichlorfon, naphthalofos, dichlorvos/DDVP, crufomate, coumaphos, haloxon;

from the class of the piperazinones/quinolines, for example: praziquantel, epsiprantel;

from the class of the piperazines, for example: piperazine, hydroxyzine;

from the class of the tetracyclines, for example: tetracycline, chlorotetracycline, doxycycline, oxytetracycline, rolitetracycline;

from various other classes, for example: bunamidine, niridazole, resorantel, omphalotin, oltipraz, nitroscanate, nitroxynil, oxamniquin, mirasan, miracil, lucanthon, hycanthon, hetolin, emetin, diethylcarbamazine, dichlorophen, diamfenetide, clonazepam, bephenium, amoscanate, clorsulon.

Active antiprotozoic ingredients include, but are not limited to, the following active ingredients: from the class of the triazines, for example: diclazuril, ponazuril, letrazuril, toltrazuril;

from the class of polyether ionophores, for example: monensin, salinomycin, maduramicin, narasin;

from the class of the macrocyclic lactones, for example: milbemycin, erythromycin;

from the class of the quinolones, for example: enrofloxacin, pradofloxacin;

from the class of the quinines, for example: chloroquin;

from the class of the pyrimidines, for example: pyrimethamine;

from the class of the sulphonamides, for example: sulfaquinoxaline, trimethoprim, sulfaclozin;

from the class of the thiamines, for example: amprolium;

from the class of the lincosamides, for example: clindamycin;

from the class of the carbanilides, for example: imidocarb;

from the class of the nitrofurans, for example: nifurtimox;

from the class of the quinazolinone alkaloids, for example: halofuginone;

from various other classes, for example: oxamniquin, paromomycin;

from the class of the vaccines or antigens from microorganisms, for example: *Babesia canis rossi*, *Eimeria tenella*, *Eimeria praecox*, *Eimeria necatrix*, *Eimeria mitis*, *Eimeria maxima*, *Eimeria brunetti*, *Eimeria acervulina*, *Babesia canis vogeli*, *Leishmania infantum*, *Babesia canis canis*, *Dictyocaulus viviparus*.

All the mixing components mentioned, as the case may be, may also form salts with suitable bases or acids if they are capable of doing so on the basis of their functional groups.

Vector Control

The compounds of the formula (I) can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host. The pathogens can be transmitted either mechanically (for example trachoma by non-stinging flies) onto a host or after injection into a host (for example malaria parasites by mosquitoes).

Examples of vectors and the diseases or pathogens they transmit are:

1) mosquitoes

*Anopheles*: malaria, filariasis;

*Culex*: Japanese encephalitis, filariasis, other viral diseases, transmission of other worms;

*Aedes*: yellow fever, dengue fever, further viral disorders, filariasis;

Simuliidae: transmission of worms, especially *Onchocerca volvulus*;

Psychodidae: transmission of leishmaniasis

2) Lice: skin infections, epidemic typhus;

3) Fleas: plague, endemic typhus, tapeworms;

4) Flies: sleeping sickness (trypanosomiasis); cholera, other bacterial diseases;

5) Mites: acariosis, epidemic typhus, rickettsialpox, tularaemia, Saint Louis encephalitis, tick-borne encephalitis (TBE), Crimean-Congo haemorrhagic fever, borreliosis;

6) Ticks: borellioses such as *Borrelia bungdorferi* sensu lato., *Borrelia duttoni*, tick-borne encephalitis, Q fever (*Coxiella burnetii*), babesioses (*Babesia canis canis*), ehrlichiosis.

Examples of vectors in the context of the present invention are insects, for example aphids, flies, leafhoppers or *thrips*, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, Psychodidae such as *Phlebotomus, Lutzomyia*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forests, in gardens and in leisure facilities, and also in the protection of materials and stored products.

Protection of Industrial Materials

The compounds of the formula (I) are suitable for protecting industrial materials against attack or destruction by insects, for example from the orders of Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) take the form of a ready-to-use pesticide, meaning that they can be applied to the material in question without further modifications. Useful further insecticides or fungicides especially include those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active compounds, as antifouling agents.

Control of Animal Pests in the Hygiene Sector

The compounds of the formula (I) are suitable for controlling animal pests in the hygiene sector. More particularly, the invention can be used in the domestic protection sector, in the hygiene protection sector and in the protection of stored products, particularly for control of insects, arachnids, ticks and mites encountered in enclosed spaces, for example dwellings, factory halls, offices, vehicle cabins, animal breeding facilities. For controlling animal pests, the compounds of the formula (I) are used alone or in combination with other active compounds and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.
Description of the Processes and Intermediates The compounds of the formula (I-A) in which Q represents oxygen can be synthesized, for example, by the process shown in Scheme 1. The compounds of the formula (I-B) in which Q represents sulphur can be obtained from compounds of the formula (I-A), for example according to Scheme 2. In the processes shown in Schemes 1 and 2, the radicals W, Y, V, A, $L^1$ and $L^2$ used in the formulae in each case have, unless indicated otherwise, the meaning given in the ranges of preference (1) to (5).

Compounds of the formula (I-A) can be synthesized as shown in Scheme 1 by initially reacting imidazolecarboxylic acids of the formula (II) with aminopyridines of the formula (III) to give compounds of the formula (IV) (cf. amidation process). Compounds of the formula (IV) are then deprotonated in analogy with known processes with a strong base such as, for example, n-butyllithium, lithium diisopropylamine or lithium tert-butoxide at low temperatures (−75 to −100° C.) in solvents such as, for example, tetrahydrofuran or diethyl ether, and then reacted with a chlorinating agent such as, for example, hexachloroethane of the formula (V) to give chloroimidazoles of the formula (VI) (cf. EP1988081; US20050250948). The chloroimidazoles of the formula (VI) can then be reacted with a nitrogen nucleophile of the formula (VII) to give compounds of the formula (I-1). Here, the compounds of the formula (VII) may optionally have to be deprotonated using a base. Bases which may be mentioned by way of example are: potassium hydroxide, potassium tert-butoxide, triethylamine, likewise all customary inorganic or organic bases, for example organic amines such as diisopropylethylamine, N-methylmorpholine, pyridine or N,N-dimethylaminopyridine, alkali metal carbonates and alkaline earth metal carbonates such as lithium carbonate, sodium carbonate, potassium carbonate or cesium carbonate; alkali metal bicarbonates such as sodium bicarbonate or potassium bicarbonate. Numerous reaction conditions have been described for the substitution of chlorine atoms in the 2-position of imidazoles by various amino compounds [cf., for example, US2005250948; WO2010144338; Jablonski, J. A. et al., Bioorg. Med. Chem. Lett. 2009, 19, 903-907; US2009186879].

Scheme 1

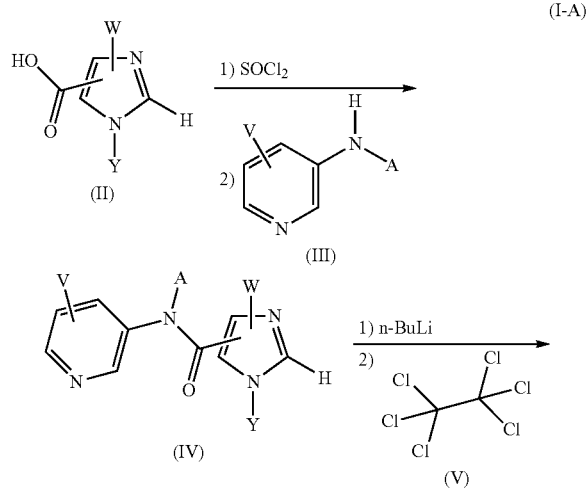

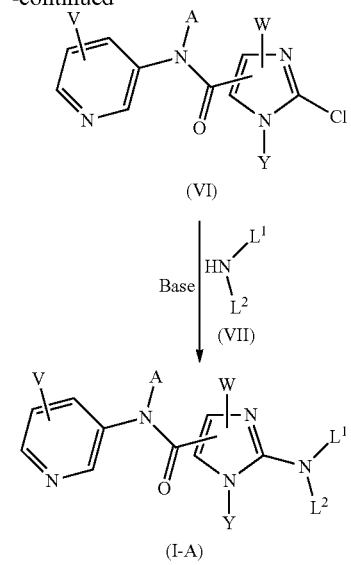

The imidazolylcarboxylic acids of the formula (II) required for the process are commercially available or can be prepared, for example, by processes known from the literature, e.g. H. Rapoport et. al.; Synthesis 1988, 10, 767-771, BASF Aktiengesellschaft patent: U.S. Pat. No. 4,864,030 A1, 1989, Takeda Pharmaceutical Company Limited patent: EP2530078 A1, 2012, TAISHO PHARMACEUTICAL CO., LTD. patent: US2012/10414 A1, 2012, Subrayan, Ramachandran P.; Thurber, Ernest L.; Rasmussen, Paul G. Tetrahedron, 1994, 50, 2641-2656.

The 3-aminopyridines of the formula (III) required for the process are commercially available or can be prepared, for example, by processes known from the literature, e.g. Liu, Zhen-Jiang; Vors, Jean-Pierre; Gesing, Ernst R. F.; Bolm, Carsten, Advanced Synthesis and Catalysis, 2010, 352, 3158-3162, BAYER CROPSCIENCE AG patent: US2010/305124 A1, 2010, Shafir, Alexandr; Buchwald, Stephen L., Journal of the American Chemical Society, 2006, 128, 8742-8743.

The NH compounds (for example alkylamines, dialkylamines, cyclic amines, hydrazines, pyrazoles, imidazoles, triazoles etc.) of the formula (VIII) required for the process are commercially available or can be prepared by general processes known in organic chemistry.

Thioamides of the formula (I-B) can be synthesized as shown in Scheme 2 by reacting compounds of the formula (I-A) with a sulphurizing agent such as, for example, diphosphorus pentasulphide or Lawesson's reagent (cf., for example, C. P. Dell in *Comprehensive Organic Functional Group Transformations*, Vol. 5, Ed.: A. R. Katrizky, O. Meth-Cohn, C. W. Rees, Pergamon, Oxford, 1995, S. 565-628; M. Jesberger, T. P. Davis, L. Barner, Synthesis 2003, 13, 1929) analogously to generally known processes.

Scheme 2

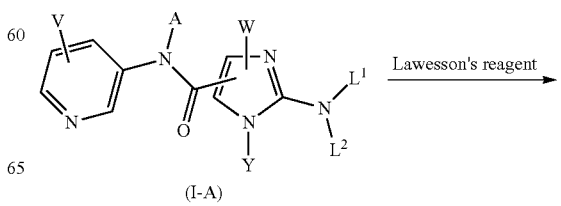

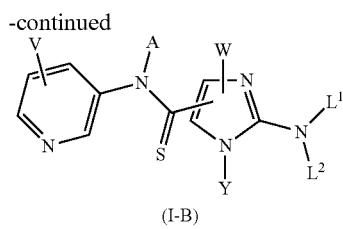

(I-B)

Amidation Process

The compounds of the formula (IV) in the process according to the invention can be synthesized using amidation reactions known from literature or analogously to the explicitly mentioned examples.

A number of reaction conditions have been described for the amidation step, for example G. Benz in Comprehensive Organic Synthesis, 1$^{st}$ Ed., Pergamon Press, Oxford, 1991, Vol. 6, pp. 381-417; P. D. Bailey et al. in Comprehensive Organic Functional Group Transformation, 1st Ed., Elsevier Science Ltd., Oxford, 1995, Vol. 5, pp. 257-308 and R. C. Larock in Comprehensive Organic Transformations, 2nd Ed., Wiley-VCH, New York, Weinheim, 1999, pp. 1929-1994. Some of these reactions proceed via intermediate carbonyl chlorides, which can be employed in isolated form or in in-situ-generated form.

The amidation reactions are optionally carried out in the presence of a condensing agent, optionally in the presence of an acid acceptor and optionally in the presence of a solvent.

Useful condensing agents are all the condensing agents typically usable for such amidation reactions. Examples include activators such as phosgene, phosphorus trichloride, phosphorus oxychloride, oxalyl chloride, oxalyl bromide or thionyl chloride; carbodiimides such as N,N'-dicyclohexyl-carbodiimide (DCC) and 1-(3-dimethylaminopropyl)-3-ethylcarbodiimide (EDCI), or other customary condensing agents such as phosphorus pentoxide, polyphosphoric acid, N,N'-carbonyldiimidazole, 2-chloropyridine 1-methoiodide (Mukaiyama's reagent), 2-ethoxy-N-ethoxycarbonyl-1,2-dihydroquinoline (EEDQ), triphenylphosphine/carbon tetrachloride, bromotripyrrolidinophosphonium hexafluorophosphate (BROP), O-(1H-benzotriazol-1-yloxy)tris(dimethylamino)phosphonium hexafluorophosphate (BOP), N,N,N',N'-bis(tetramethylene)chlorouronium tetrafluoroborate, O-(1H-benzotriazol-1-yl)-N,N,N',N'-tetramethyluronium hexafluorophosphate (HBTU), O-(1H-benzotriazol-1-yl)-N,N,N',N'-bis(tetramethylene)uronium hexafluorophosphate, O-(1H-benzotriazol-1-yl)-N,N,N',N'-tetramethyluronium tetrafluoroborate (TBTU), O-(1H-benzotriazol-1-yl)-N,N,N',N'-bis(tetramethylene)uronium tetrafluoroborate, O-(7-azabenzotriazol-1-yl)-N,N,N',N'-tetramethyluronium hexafluorophosphate (HATU), 1-hydroxybenzotriazole (HOBt) and 4-(4,6-dimethoxy-1,3,5-triazin-2-yl)-4-methylmorpholinium salt (DMT.MM), usually available as a chloride. These reagents can be used separately or in combination.

Suitable acid acceptors are all customary inorganic or organic bases, for example organic amines such as triethylamine, diisopropylethylamine, N-methylmorpholine, pyridine or N,N-dimethylaminopyridine, alkali metal and alkaline earth metal carbonates such as lithium carbonate, sodium carbonate, potassium carbonate or caesium carbonate; alkali metal bicarbonates such as sodium bicarbonate or potassium bicarbonate. The amidation reaction in the processes according to the invention is optionally carried out in the presence of a suitable reaction auxiliary such as, for example, N,N-dimethylformamide or N,N-dimethylaminopyridine. Suitable solvents or diluents are all inert organic solvents, for example aliphatic or aromatic hydrocarbons (such as petroleum ether, toluene, cyclohexane), halogenated hydrocarbons (such as chlorotoluene, dichlorobenzene, dichloromethane, chloroform, 1,2-dichloroethane), ethers (such as diethyl ether, dioxane, tetrahydrofuran, 1,2-dimethoxyethane), esters (such as ethyl or methyl acetate), nitrohydrocarbons (such as nitromethane, nitroethane, nitrobenzene), nitriles (such as acetonitrile, propionitrile, butyronitrile, benzonitrile), amides (such as N,N-dimethylformamide, N,N-dimethylacetamide, N-methylformanilide, N-methylpyrrolidone, hexamethylphosphoramide), and also dimethyl sulphoxide or water or mixtures of the solvents mentioned.

It is also possible to use mixed anhydrides for preparation of compounds of the formula (III) (cf. J. Am. Chem. Soc. 1967, 5012). In this process, it is possible to use chloroformic esters, for example methyl chloroformate, ethyl chloroformate, isobutyl chloroformate and isopropyl chloroformate. Likewise, it is possible for this purpose to use diethylacetyl chloride, trimethylacetyl chloride and similar compounds.

The invention also provides intermediates of the formula (VI)

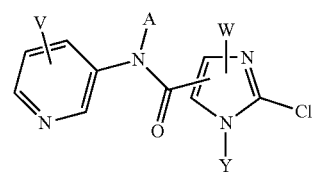

(VI)

where the radicals have the meanings according to one of the ranges of preference (1-1) to (5-1) or (1-2) to (5-2) and especially preferably the meaning according to range of preference (5-1) or (5-2).

PREPARATION EXAMPLES

The preparation and use examples which follow illustrate the invention without limiting it.

Synthesis Example No. 1

N,1-dimethyl-N-(pyridin-3-yl)-2-[3-(trifluoromethyl)-1H-pyrazol-1-yl]-1H-imidazole-5-carboxamide (Compound No. I-1-007)

Step 1: N,1-Dimethyl-N-(pyridin-3-yl)-1H-imidazole-5-carboxamide

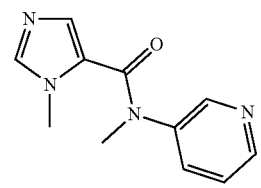 [SMILES: CN(C(=O)c1cncn1C)c1cccnc1]

12.71 g (104.7 mmol) of thionyl chloride were added to a suspension of 12 g (95.2 mmol) of 1-methylimidazole-5-carboxylic acid in 72 ml of toluene, and the mixture was stirred at 130° C. overnight. The reaction mixture was concentrated under reduced pressure. A solution of 10.3 g (95.2 mmol) of 3-methylaminopyridine in 72 ml of pyridine was added to the residue, and the resulting reaction mixture was heated at 115° C. for 4 h. The mixture was then once more concentrated under reduced pressure and the residue was purified by column chromatography on silica gel using the mobile phase acetonitrile/methanol 3:1. This gave 8.1 g (39.3% of theory) of the title compound and 9.5 g (37.1% of theory) of the HCl salt of the title compound.

HPLC-MS: log P[n]=0.44; mass (m/z): 217.1; $^1$H-NMR (CD$_3$CN, 400 MHz); δ=3.39 (s, 3H), 3.81 (s, 3H), 6.17 (s, 1H), 7.36-7.40 (m, 2H), 7.67-7.70 (m, 1H), 8.41 (m, 1 H) 8.47 (m, 1H) ppm.

Step 2: 2-Chloro-N, 1-dimethyl-N-(pyridin-3-yl)-1H-imidazole-5-carboxamide

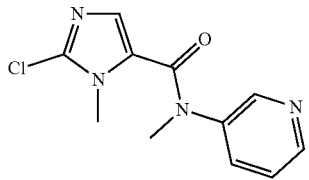 [SMILES: CN(C(=O)c1cnc(Cl)n1C)c1cccnc1]

10.0 g (46.2 mmol) of N,1-dimethyl-N-(pyridin-3-yl)-1H-imidazole-5-carboxamide were dissolved in 150 ml of dry THF and cooled to −78° C. 20.34 ml (50.8 mmol) of a 2.5 molar solution of n-BuLi in n-hexane were added dropwise over a period of 5 minutes, and the mixture was stirred for another 30 minutes at −78° C. 12.0 g (50.8 mmol) of hexachloroethane, dissolved in 100 ml of THF, were then added dropwise over 5 minutes. The mixture was stirred at −78° C. for a further 45 minutes and then warmed to room temperature over 60 minutes. The mixture was poured into 400 ml of saturated ammonium chloride solution and extracted repeatedly with dichloromethane. The organic phases were combined, washed with a little water, and dried with magnesium sulphate. The solvent was distilled off and the residue was purified by preparative reversed phase HPLC using the mobile phase water/acetonitrile. This gave 7.27 g (62% of theory) of 2-chloro-N, 1-dimethyl-N-(pyridin-3-yl)-1H-imidazole-5-carboxamide.

HPLC-MS: log P[n]=0.88; mass (m/z): 251.1; $^1$H-NMR (D$^6$-DMSO, 400 MHz); δ=3.37 (s, 3H), 3.75 (s, 3H), 6.20 (s, 1H), 7.45 (m, 1H), 7.86 (m, 1H), 8.49 (m, 1 H) 8.53 (m, 1H) ppm.

Step 3: N,1-dimethyl-N-(pyridin-3-yl)-2-[3-(trifluoromethyl)-1H-pyrazol-1-yl]-1H-imidazole-5-carboxamide (compound No. I-1-007)

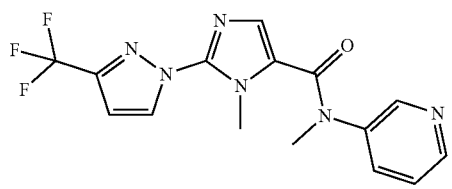 [SMILES: CN(C(=O)c1cnc(-n2ccc(C(F)(F)F)n2)n1C)c1cccnc1]

2-Chloro-N,1-dimethyl-N-(pyridin-3-yl)-1H-imidazole-5-carboxamide (150 mg, 0.59 mmol) was initially charged in dimethylformamide (5.0 ml), and cesium carbonate (389.9 mg, 1.19 mmol) was added. The reaction mixture was stirred at 120° C. overnight and the solvent was then distilled off completely under reduced pressure. The residue was chromatographed on silica gel using the mobile phase ethyl acetate/methanol (80:20). This gave 61 mg (29.1% of theory) of N,1-dimethyl-N-(pyridin-3-yl)-2-[3-(trifluoromethyl)-1H-pyrazol-1-yl]-1H-imidazole-5-carboxamide.

HPLC-MS: log P[n]=1.87; mass (m/z): 351.1; $^1$H-NMR (D$^6$-DMSO, 400 MHz); δ=3.42 (s, 3H), 3.81 (s, 3H), 6.28 (s, 1H), 6.83 (m, 1H), 7.39 (m, 1H), 7.73 (m, 1H), 8.08 (m, 1H), 8.49 (m, 2 H) ppm.

Synthesis Example No. 2

N,1-Dimethyl-2-(morpholin-4-yl)-N-(pyridin-3-yl)-1H-imidazole-5-carboxamide (compound No. I-1-009)

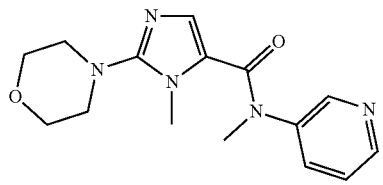 [SMILES: CN(C(=O)c1cnc(N2CCOCC2)n1C)c1cccnc1]

2-Chloro-N,1-dimethyl-N-(pyridin-3-yl)-1H-imidazole-5-carboxamide (150 mg, 0.59 mmol) and morpholine (216 mg, 2.48 mmol) were stirred at 100° C. overnight. The mixture was poured into water and extracted repeatedly with ethyl acetate. The combined organic phases were dried over magnesium sulphate, the solvent was distilled off under reduced pressure and the residue was purified by preparative reversed phase HPLC using the mobile phase water/acetonitrile. This gave 135 mg (75.8% of theory) of N, 1-dimethyl-2-(morpholin-4-yl)-N-(pyridin-3-yl)-1H-imidazole-5-carboxamide.

HPLC-MS: log P[n]=0.85; mass (m/z): 302.1; $^1$H-NMR (CD$_3$CN, 400 MHz); δ=3.26 (m, 2H), 3.30 (s, 3H), 3.44 (m, 2H), 3.57 (s, 3H), 3.80 (m, 2H), 3.93 (m, 2H), 5.90 (s, 1H), 7.6-8.0 (m, 2H), 8.38-8.47 (m, 1H), 8.59-8.67 (m, 1 H) ppm.

Further compounds of the formula (I) prepared analogously to the examples given above are listed in Table 1.

Table 1

Compounds of the Formula (I-1)

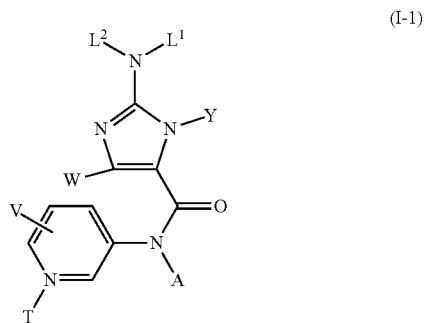

(I-1)

in which T represents a free electron pair and the other substituents have the meanings given in the table:

| Ex. No. | L¹-N-L² | Y | A | V | W | Logp [n][a)] |
|---|---|---|---|---|---|---|
| I-1-00 | pyrrole | $CH_3$ | $CH_3$ | H | H | 1.27 |
| I-1-002 | pyrazole | $CH_3$ | $CH_3$ | H | H | 1.01 |
| I-1-003 | 3-cyanopyrazole | $CH_3$ | $CH_3$ | H | H | 1.31 |
| I-1-004 | 3-chloropyrazole | $CH_3$ | $CH_3$ | H | H | 1.48 |
| I-1-005 | 4-chloropyrazole | $CH_3$ | $CH_3$ | H | H | 1.49 |
| I-1-006 | 4-trifluoromethylpyrazole | $CH_3$ | $CH_3$ | H | H | 1.82 |
| I-1-007 | 3-trifluoromethylpyrazole | $CH_3$ | $CH_3$ | H | H | 1.87 |
| I-1-008 | 4-cyanopyrazole | $CH_3$ | $CH_3$ | H | H | 1.14 |
| I-1-009 | morpholine | $CH_3$ | $CH_3$ | H | H | 0.85 |
| I-1-010 | 4-trifluoromethylimidazole | $CH_3$ | $CH_3$ | H | H | 1.38 |
| I-1-011 | 3-methylthio-1,2,4-triazole | $CH_3$ | $CH_3$ | H | H | 1.27 |
| I-1-012 | 3-methylthiopyrazole | $CH_3$ | $CH_3$ | H | H | 1.57 |

-continued
| Ex. No. | L¹-N-L² | Y | A | V | W | Logp [n][a] |
|---|---|---|---|---|---|---|
| I-1-013 | 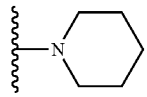 | $CH_3$ | $CH_3$ | H | H | 1.53 |
| I-1-014 | 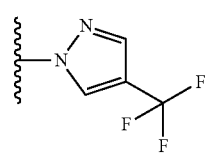 [SMILES: *n1cc(C(F)(F)F)cn1] | $CH_3$ | $C_2H_5$ | H | H | 2.09 |
| I-1-015 | 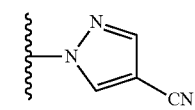 [SMILES: *n1cc(C#N)cn1] | $CH_3$ | $C_2H_5$ | H | H | 1.42 |
| I-1-016 |  | $CH_3$ | $CH_3$ | H | H | 1.87 |
| I-1-017 | 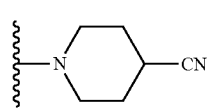 | $CH_3$ | $CH_3$ | H | H | 1.16 |
| I-1-018 | 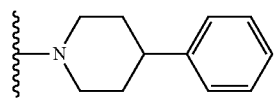 | $CH_3$ | $CH_3$ | H | H | 2.38 |
| I-1-019 | 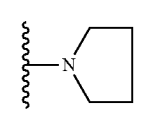 | $CH_3$ | $CH_3$ | H | H | 1.19 |
| I-1-020 | 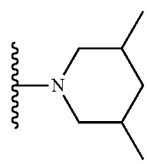 [SMILES: *N1CC(C)CC(C)C1] | $CH_3$ | $CH_3$ | H | H | 2.21 |
| I-1-021 | 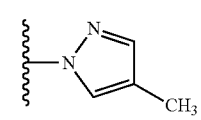 | $CH_3$ | $CH_3$ | H | H | 1.29 |
| I-1-022 | 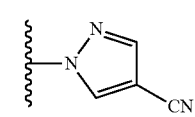 | $CH_3$ |  | H | H | 1.4 |
| I-1-023 | 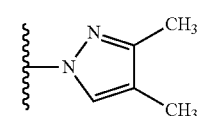 | $CH_3$ | $CH_3$ | H | H | 1.42 |
| I-1-024 | 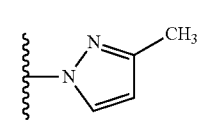 | $CH_3$ | $CH_3$ | H | H | 1.18 |
| I-1-025 | 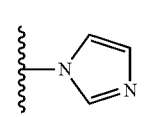 | $CH_3$ | $CH_3$ | H | H | 0.56 |

-continued

| Ex. No. | L¹-N-L² | Y | A | V | W | Logp [n][a)] |
|---------|---------|---|---|---|---|---------|
| I-1-026 | (1-(3-chloro-1,2,4-triazolyl)) | CH₃ | CH₃ | H | H | 1.17 |
| I-1-027 | (1-(4,5,6-cyclopentane-fused pyrazolyl)) | CH₃ | CH₃ | H | H | 1.5 |
| I-1-028 | (1-(5-amino-4-cyanopyrazolyl)) | CH₃ | CH₃ | H | H | 0.78 |
| I-1-029 | (1-(3-cyanopyrazolyl)) | CH₃ | C₂H₅ | H | H | 1.53 |
| I-1-030 | (1-(4-isopropylpyrazolyl)) | CH₃ | CH₃ | H | H | 1.84 |
| I-1-031 | (1-(3-cyano-1,2,4-triazolyl)) | CH₃ | CH₃ | H | H | 1.22 |

TABLE 2

¹H NMR data of selected examples from Table 1 [b)]

Example I-1-001: ¹H-NMR(400.0 MHz. d₆-DMSO): δ = 8.313(1.1); 7.941(1.1); 7.921(1.3); 7.887(0.4); 7.871(0.4); 7.140(3.4); 6.290(5.7); 6.240(0.4); 3.938(2.9); 3.670(16.0); 3.403(17.1); 3.315(45.9); 3.225(0.4); 2.891(0.5); 2.731(0.5); 2.675(1.7); 2.671(2.3); 2.666(1.7); 2.576(0.7); 2.558(1.0); 2.510(135.7); 2.506(266.3); 2.502(355.6); 2.497(274.4); 2.493(144.5); 2.456(0.4); 2.333(1.5); 2.328(2.1); 2.324(1.6); 2.117(0.3); 1.140(0.7); 0.146(2.0); 0.033(0.7); 0.028(0.7); 0.008(17.1); 0.000(428.7); −0.008(18.8); −0.150(2.0)

Example I-1-002: ¹H-NMR(400.0 MHz. d₆-DMSO): δ = 8.578(0.8); 8.510(1.1); 8.312(4.7); 8.192(2.1); 8.185(2.1); 7.918(0.8); 7.897(1.0); 7.866(2.3); 7.862(2.5); 7.840(0.7); 7.489(0.8); 7.478(0.8); 7.469(0.9); 7.455(1.0); 7.443(0.7); 7.433(0.6); 7.421(0.5); 6.561(1.5); 6.556(1.9); 6.550(1.5); 6.484(1.4); 6.274(2.3); 3.936(8.9); 3.795(16.0); 3.469(0.4); 3.433(0.5); 3.427(0.5); 3.410(14.5); 3.402(9.1); 3.382(1.0); 3.363(2.6); 3.355(2.0); 3.343(2.8); 3.314(1369.0); 3.278(1.0); 3.270(0.5); 3.253(0.4); 3.243(0.4); 2.895(0.6); 2.885(0.3); 2.784(0.4); 2.772(0.3); 2.740(0.3); 2.675(7.9); 2.670(11.0); 2.666(8.4); 2.637(0.8); 2.621(0.7); 2.593(1.0); 2.523(27.6); 2.519(41.7); 2.510(558.5); 2.506(1165.3); 2.501(1606.2); 2.496(1235.8); 2.492(633.2); 2.447(0.8); 2.432(0.5); 2.407(0.9); 2.332(7.6); 2.328(10.8); 2.323(8.1); 0.146(1.5); 0.008(9.5); 0.000(316.0); −0.008(12.1); −0.150(1.4)

Example I-1-003: ¹H-NMR(400.0 MHz. CD3CN): δ = 8.483(2.0); 8.127(2.6); 8.121(2.6); 7.744(1.2); 7.724(1.3); 7.410(1.0); 7.398(1.1); 7.390(1.0); 7.378(0.9); 6.976(2.6); 6.970(2.5); 6.293(2.9); 5.447(16.0); 3.827(14.2); 3.429(14.1); 2.174(2.6); 1.952(2.6); 1.951(2.6); 1.946(4.4); 1.941(5.8); 1.935(4.2); 1.929(2.2); 0.000(24.6)

Example I-1-004: ¹H-NMR(400.0 MHz. CD3CN): δ = 8.491(1.3); 8.488(1.4); 8.479(1.7); 8.475(2.8); 8.467(2.0); 7.950(2.8); 7.943(2.8); 7.741(0.7); 7.737(0.9); 7.734(0.9); 7.730(0.7); 7.720(0.8); 7.716(1.0); 7.714(1.0); 7.710(0.8); 7.404(1.1); 7.392(1.1); 7.383(1.0); 7.371(1.0); 6.481(2.7); 6.475(2.7); 6.244(2.9); 5.447(3.2); 3.817(16.0); 3.756(0.6); 3.421(15.9); 3.387(0.6); 3.260(0.5); 2.156(17.7); 1.958(0.6); 1.952(3.6); 1.946(6.7); 1.940(9.0); 1.933(6.1); 1.927(3.1); 0.008(0.7); 0.000(18.4); −0.009(0.7)

Example I-1-005: ¹H-NMR(400.0 MHz. CD3CN): δ = 8.492(1.1); 8.488(1.2); 8.480(1.2); 8.476(1.5); 8.472(1.8); 8.466(1.7); 8.051(3.8); 7.756(3.2); 7.744(0.7); 7.740(0.8); 7.737(0.8); 7.734(0.7); 7.723(0.8); 7.720(0.9); 7.717(0.9); 7.713(0.8); 7.406(1.0); 7.394(1.0); 7.386(0.9); 7.374(0.8); 6.249(2.7); 5.446(12.0); 3.814(16.0); 3.420(15.6); 2.155(6.6); 1.964(0.3); 1.958(0.8); 1.952(4.7); 1.946(8.7); 1.939(11.9); 1.933(8.3); 1.927(4.3); 0.008(0.8); 0.000(23.7); −0.009(1.0)

Example I-1-006: ¹H-NMR(400.0 MHz. CD3CN): δ = 8.496(1.3); 8.481(2.2); 8.474(1.8); 8.407(2.8); 8.061(3.1); 7.755(0.8); 7.751(1.0); 7.748(1.0); 7.745(0.8); 7.734(0.9); 7.730(1.1); 7.728(1.1); 7.724(0.8); 7.414(1.1); 7.402(1.1); 7.393(1.0); 7.381(0.9); 6.282(2.8); 5.448(2.8); 3.823(16.0); 3.428(15.7); 2.889(0.5); 2.772(0.4); 2.188(7.1); 1.964(0.4); 1.958(0.9); 1.952(4.6); 1.946(8.2); 1.940(10.9); 1.934(7.3); 1.928(3.7); 1.100(0.5); 1.084(0.5); 0.000(21.1); −0.008(0.7)

Example I-1-007: ¹H-NMR(400.0 MHz. CD3CN): δ = 8.498(1.6); 8.495(1.7); 8.483(3.7); 8.477(2.5); 8.098(2.0); 8.094(2.0); 7.751(0.9); 7.747(1.1); 7.745(1.1); 7.741(0.9); 7.731(1.0); 7.727(1.2); 7.724(1.2); 7.721(1.0); 7.411(1.2); 7.410(1.1); 7.399(1.3); 7.391(1.2); 7.379(1.1); 6.842(2.3); 6.836(2.3); 6.284(3.0); 3.817(16.0); 3.429(15.9); 2.145(5.5); 1.963(0.4); 1.952(4.4); 1.945(7.9); 1.939(10.3); 1.933(7.2); 1.927(3.7); 0.008(2.2); 0.000(23.1)

Example I-1-008: ¹H-NMR(400.0 MHz. CD3CN): δ = 8.533(0.4); 8.525(4.0); 8.497(1.3); 8.494(1.3); 8.485(1.4); 8.482(1.6);

TABLE 2-continued

¹H NMR data of selected examples from Table 1 [b]

8.473(1.9); 8.468(1.8); 8.124(3.5); 7.960(0.5); 7.952(0.5); 7.750(0.7); 7.746(0.8); 7.744(0.8); 7.740(0.7); 7.730(0.8); 7.726(0.9); 7.723(0.9); 7.720(0.7); 7.412(1.0); 7.400(1.0); 7.392(0.9); 7.380(0.9); 6.283(2.3); 3.815(16.0); 3.426(15.4); 3.336(0.4); 3.261(2.2); 2.763(0.8); 2.468(0.4); 2.173(192.4); 2.120(0.5); 2.114(0.6); 2.107(0.7); 2.101(0.5); 1.964(2.4); 1.958(5.9); 1.952(34.5); 1.946(62.9); 1.940(84.8); 1.934(57.6); 1.928(29.2); 1.774(0.4); 1.768(0.5); 1.271(0.6); 0.146(0.8); 0.008(7.4); 0.000(170.6); −0.009(6.3); −0.150(0.8)

Example I-1-009: ¹H-NMR(601.6 MHz. CD3CN): δ = 19.985(0.6); 9.485(0.7); 8.922(1.3); 8.845(1.0); 8.676(1.1); 8.609(0.8); 8.463(0.9); 8.405(0.7); 8.000(1.8); 7.952(0.8); 7.894(0.8); 7.621(0.8); 6.998(1.2); 6.714(1.0); 3.925(6.5); 3.815(5.5); 3.798(5.1); 3.678(6.6); 3.646(2.6); 3.595(2.7); 3.531(9.1); 3.454(5.1); 3.382(2.3); 3.307(5.2); 3.303(8.2); 3.168(6.7); 2.926(4.9); 2.859(9.1); 2.692(16.0); 1.976(9.8); 1.972(10.9); 1.968(9.3); 1.087(0.5)

Example I-1-010: ¹H-NMR(400.0 MHz. CD3CN): δ = 8.509(1.0); 8.506(1.0); 8.497(1.0); 8.494(1.0); 8.477(1.3); 8.471(1.3); 7.899(1.6); 7.806(0.4); 7.803(1.3); 7.800(1.8); 7.797(1.2); 7.767(0.6); 7.763(0.7); 7.760(0.7); 7.756(0.7); 7.746(0.7); 7.742(0.8); 7.740(0.7); 7.736(0.7); 7.428(0.8); 7.426(0.8); 7.416(0.8); 7.414(0.8); 7.408(0.7); 7.406(0.7); 7.396(0.7); 7.394(0.7); 6.278(1.6); 3.671(16.0); 3.425(15.1); 2.178(39.1); 1.964(0.5); 1.958(1.1); 1.952(8.8); 1.946(16.4); 1.940(22.8); 1.934(15.6); 1.927(7.9); 1.100(2.4); 1.084(2.3); 0.008(2.0); 0.000(58.8); −0.009(1.9)

Example I-1-011: ¹H-NMR(400.0 MHz. CD3CN): δ = 8.545(3.8); 8.498(1.1); 8.486(1.1); 8.482(1.2); 8.473(1.4); 8.468(1.5); 7.753(0.6); 7.749(0.7); 7.747(0.7); 7.743(0.6); 7.733(0.7); 7.729(0.8); 7.726(0.8); 7.722(0.7); 7.415(0.8); 7.413(0.8); 7.403(0.8); 7.401(0.8); 7.394(0.8); 7.393(0.7); 7.382(0.7); 7.381(0.7); 6.282(2.0); 5.447(2.9); 3.814(15.4); 3.756(0.5); 3.426(14.9); 3.388(0.5); 2.611(16.0); 2.523(0.4); 2.170(160.1); 2.107(0.4); 1.964(1.5); 1.958(2.9); 1.952(21.7); 1.946(40.4); 1.940(55.7); 1.934(37.8); 1.928(19.1); 0.008(1.9); 0.000(64.7); −0.009(2.1)

Example I-1-012: ¹H-NMR(400.0 MHz. CD3CN): δ = 8.487(1.1); 8.483(1.2); 8.475(2.6); 8.468(1.7); 7.939(2.5); 7.933(2.6); 7.742(0.6); 7.739(0.7); 7.736(0.7); 7.732(0.7); 7.722(0.7); 7.718(0.8); 7.716(0.8); 7.712(0.7); 7.470(0.6); 7.405(0.8); 7.404(0.9); 7.394(0.8); 7.392(0.9); 7.385(0.8); 7.384(0.8); 7.372(0.8); 6.403(2.5); 6.397(2.5); 6.306(0.4); 6.302(0.4); 6.234(2.8); 5.218(1.0); 5.094(0.5); 3.852(15.1); 3.420(14.8); 3.121(0.4); 2.758(0.4); 2.541(16.0); 2.416(0.8); 2.404(0.5); 2.381(2.6); 2.379(2.9); 2.372(0.9); 2.355(0.5); 2.350(0.5); 2.196(13.3); 1.959(0.5); 1.953(3.5); 1.947(6.5); 1.940(9.0); 1.934(6.2); 1.928(3.1); 1.269(0.4); 0.000(8.8)

Example I-1-013: ¹H-NMR(400.0 MHz. d6-DMSO): δ = 8.497(2.7); 8.490(2.7); 8.477(1.6); 8.474(1.9); 8.465(1.7); 8.462(1.9); 7.837(0.9); 7.833(1.1); 7.831(1.2); 7.827(1.0); 7.816(1.0); 7.813(1.2); 7.806(1.0); 7.457(1.4); 7.445(1.4); 7.436(1.3); 7.424(1.2); 5.915(5.4); 5.756(2.3); 3.522(16.0); 3.338(15.8); 3.321(27.8); 2.923(3.1); 2.911(4.3); 2.897(3.5); 2.506(15.6); 2.501(22.0); 2.497(17.4); 1.617(0.7); 1.589(3.2); 1.578(2.6); 1.512(1.5); 1.501(1.4); 0.781(0.3); 0.008(0.4); 0.000(9.6); −0.008(0.5)

Example I-1-014: ¹H-NMR(400.0 MHz. d6-DMSO): δ = 8.926(3.2); 8.539(2.6); 8.526(1.4); 8.343(4.0); 7.916(0.9); 7.912(1.1); 7.906(0.9); 7.895(1.0); 7.891(1.2); 7.889(1.2); 7.505(1.2); 7.493(1.2); 7.485(1.1); 7.473(1.0); 6.274(2.7); 3.915(0.9); 3.897(3.0); 3.879(3.0); 3.862(1.0); 3.837(0.6); 3.763(16.0); 3.317(72.3); 3.283(0.4); 2.671(0.6); 2.506(71.2); 2.501(95.3); 2.497(73.5); 2.328(0.6); 1.147(3.4); 1.129(7.3); 1.112(3.3); 0.008(2.5); 0.000(53.7)

Example I-1-015: 1H-NMR(400.0 MHz. d6-DMSO):
δ = 9.09(4.9); 8.546(2.24); 8.538(2.81); 8.533(1.75); 8.525(1.69); 8.521(1.63); 8.465(4.85); 7.916(0.78); 7.912(0.96); 7.91 (0.91); 7.906(0.79); 7.896(0.9); 7.892(1.02); 7.889(1.02); 7.885(0.85); 7.504(1.16); 7.492(1.17); 7.484(1.1); 7.472(1.06); 6.281(2.27); 4.346(1.23); 4.335(1.28); 3.914(0.81); 3.896(2.67); 3.878(2.71); 3.861(0.85); 3.794(0.37); 3.784(0.4); 3.779(0.59); 3.765(16); 3.754(0.56); 3.324(4.47); 2.512(5.8); 2.508(12.14); 2.503(16.16); 2.499(11.5); 2.494(5.45); 1.144(3.13); 1.127(7.09); 1.109(3.04); 1.046(9.45); 1.031(9.35); 0(9.17); −0.008(0.33)

Example I-1-016: ¹H-NMR(400.0 MHz. d6-DMSO): δ = 8.495(2.2); 8.489(2.3); 8.476(1.5); 8.472(1.7); 8.464(1.6); 8.461(1.7); 7.834(0.8); 7.831(1.0); 7.828(1.0); 7.824(0.9); 7.814(0.9); 7.810(1.1); 7.808(1.1); 7.804(0.9); 7.456(1.2); 7.444(1.2); 7.435(1.1); 7.423(1.1); 5.912(5.3); 5.753(0.5); 3.518(16.0); 3.337(15.6); 3.317(32.1); 3.192(1.3); 3.161(1.5); 2.712(0.9); 2.707(1.0); 2.682(1.8); 2.676(1.9); 2.652(0.9); 2.646(0.8); 2.524(0.8); 2.506(36.3); 2.501(51.1); 2.497(39.3); 2.493(19.8); 1.646(1.1); 1.619(1.2); 1.614(1.2); 1.490(0.3); 1.480(0.4); 1.472(0.4); 1.463(0.5); 1.454(0.4); 1.291(0.5); 1.282(0.5); 1.260(1.0); 1.251(1.1); 1.230(0.9); 1.222(0.9); 1.201(0.3); 0.933(5.9); 0.916(5.6); 0.008(1.0); 0.000(30.1); −0.008(1.3)

Example I-1-018: ¹H-NMR(400.0 MHz. d6-DMSO): δ = 8.512(2.4); 8.506(2.4); 8.485(1.7); 8.482(1.8); 8.473(1.8); 8.470(1.8); 8.314(0.4); 8.025(2.5); 7.850(0.9); 7.846(1.1); 7.843(1.0); 7.839(0.9); 7.829(1.1); 7.825(1.1); 7.823(1.2); 7.819(1.0); 7.466(1.3); 7.455(1.3); 7.446(1.2); 7.434(1.1); 7.326(1.0); 7.318(1.0); 7.307(3.1); 7.300(2.5); 7.290(3.8); 7.279(4.2); 7.274(4.8); 7.253(2.8); 7.249(3.0); 7.232(1.4); 7.223(0.7); 7.216(1.2); 7.212(1.8); 7.208(1.1); 7.195(2.8); 7.189(0.7); 7.178(1.1); 5.947(5.7); 4.330(0.4); 4.325(0.4); 4.319(0.4); 4.298(0.4); 4.293(0.4); 4.288(0.4); 3.800(0.4); 3.794(0.4); 3.789(0.4); 3.767(0.4); 3.762(0.5); 3.756(0.4); 3.575(16.0); 3.350(16.6); 3.317(113.0); 3.173(0.5); 3.165(0.4); 3.141(0.8); 3.134(0.8); 3.108(0.4); 3.101(0.4); 2.881(0.7); 2.850(1.0); 2.844(1.1); 2.828(0.9); 2.814(0.7); 2.805(0.5); 2.796(0.7); 2.788(0.4); 2.766(0.4); 2.710(0.4); 2.702(0.6); 2.675(1.7); 2.670(2.3); 2.666(1.4); 2.661(1.1); 2.645(1.0); 2.638(1.0); 2.622(0.3); 2.524(3.1); 2.519(5.0); 2.510(67.0); 2.506(141.1); 2.501(197.5); 2.497(147.5); 2.492(70.8); 2.332(0.8); 2.328(1.1); 2.323(0.8); 1.841(0.5); 1.834(0.5); 1.817(2.0); 1.810(2.5); 1.798(3.3); 1.790(2.7); 1.771(1.1); 1.762(1.0); 1.550(0.7); 1.539(0.6); 1.519(0.6); 1.507(0.5); 1.477(0.3); 1.445(0.6); 1.434(0.6); 1.414(0.5); 1.403(0.5); 0.146(0.5); 0.008(3.7); 0.000(109.9); −0.009(3.8); −0.150(0.5)

Example I-1-019: ¹H-NMR(400.0 MHz. d6-DMSO): δ = 8.486(2.0); 8.480(2.0); 8.460(1.5); 8.456(1.6); 8.448(1.6); 8.444(1.6); 8.313(0.5); 7.821(0.8); 7.817(0.9); 7.814(0.9); 7.811(0.8); 7.800(0.9); 7.797(1.0); 7.794(1.0); 7.790(0.9); 7.448(1.1); 7.436(1.1); 7.428(1.0); 7.416(1.0); 5.895(5.8); 3.547(16.0); 3.332(15.8); 3.316(32.2); 3.303(2.6); 3.292(2.0); 3.286(5.8); 3.269(2.1); 2.675(0.6); 2.670(0.6); 2.666(0.4); 2.524(1.5); 2.519(2.2); 2.510(31.6); 2.506(67.0); 2.501(94.5); 2.496(70.6); 2.492(33.9); 2.332(0.4); 2.328(0.6); 2.323(0.4); 1.832(2.1); 1.823(2.1); 1.815(5.7); 1.807(2.1); 1.798(2.0); 1.561(0.4); 0.008(1.5); 0.000(47.5); −0.009(1.6)

Example I-1-020: ¹H-NMR(400.0 MHz. d6-DMSO): δ = 8.497(0.6); 8.490(2.8); 8.484(2.4); 8.474(2.0); 8.471(1.9); 8.463(2.0); 8.459(1.8); 8.313(0.4); 7.832(1.8); 7.828(1.2); 7.826(1.0); 7.822(0.9); 7.812(1.2); 7.805(1.7); 7.802(0.9); 7.456(1.3); 7.444(1.4); 7.435(1.3); 7.424(1.2); 5.913(5.5); 5.906(1.2); 3.549(2.9); 3.518(16.0); 3.339(19.0); 3.317(77.1); 3.155(1.2); 3.128(1.3); 2.675(0.6); 2.670(0.8); 2.666(0.6); 2.610(0.3); 2.524(2.1); 2.510(40.6); 2.506(83.5); 2.501(115.5); 2.497(86.2); 2.492(41.4); 2.332(0.5); 2.328(0.7); 2.324(0.5); 2.247(1.3); 2.219(2.3); 2.189(1.5); 1.756(1.0); 1.749(1.1); 1.726(1.5); 1.718(1.2); 1.700(0.6); 1.363(0.3); 1.349(0.5); 0.980(2.0); 0.963(2.0); 0.870(0.4); 0.853(0.5); 0.836(10.4); 0.820(10.3); 0.764(1.6); 0.747(1.5); 0.654(0.8); 0.624(0.7); 0.008(2.1); 0.000(60.4); −0.009(2.2)

Example I-1-021: 1 H-NMR(400.0 MHz. d6-DMSO):
δ = 8.572(2.06); 8.566(2.11); 8.505(1.45); 8.502(1.53); 8.493(1.55); 8.49(1.49); 7.94(3.22); 7.913(0.84); 7.91(1.02); 7.903 (0.82); 7.893(0.94); 7.889(1.08); 7.887(1.06); 7.883(0.88); 7.679(3.82); 7.625(0.66); 7.485(1.15); 7.473(1.16); 7.464(1.1); 7.453(1.04); 7.188(0.57); 7.185(0.58); 6.847(0.61); 6.844(0.6); 6.247(3.04); 5.756(10.05); 3.798(16); 3.662(3.33); 3.403(14.59); 3.321(41.24); 2.67(0.74); 2.506(97.87); 2.501(127.31); 2.497(94.18); 2.333(0.55); 2.328(0.73); 2.324(0.55); 2.094 (2.3); 2.074(10.47); 0.146(0.61); 0.008(5.91); 0(135.75); −0.008(6.47); −0.15(0.6)

Example I-1-022: 1H-NMR(400.0 MHz. d6-DMSO):
δ = 9.138(5.04); 8.576(2.35); 8.57(2.38); 8.514(1.66); 8.511(1.72); 8.502(1.82); 8.499(1.81); 8.48(4.97); 8.141(0.63);

TABLE 2-continued

1H NMR data of selected examples from Table 1 b)

7.873(0.94); 7.869(1.19); 7.867(1.16); 7.863(0.93); 7.853(1.07); 7.849(1.28); 7.847(1.29); 7.843(0.99); 7.496(1.29); 7.484(1.28);
7.476(1.26); 7.464(1.19); 6.938(2.34); 5.755(15.9); 3.744(16); 3.732(1.3); 3.424(0.64); 3.416(0.85); 3.407(1.23); 3.398
(0.88); 3.389(0.67); 3.379(0.42); 3.321(1.59); 2.506(20.92); 2.502(27.82); 2.498(21.37); 2.074(2.06); 0.89(0.53); 0.872(2.32);
0.858(2.38); 0.854(2.06); 0.841(0.68); 0.608(0.7); 0.595(2.09); 0.589(2.34); 0.586(2.16); 0.581(2.03); 0.568(0.59);
0.008(0.84); 0(19.56); −0.008(0.97)
Example I-1-023: 1H-NMR(400.0 MHz. $d_6$-DMSO):
δ = 8.562(2.48); 8.556(2.53); 8.5(1.69); 8.497(1.88); 8.488(1.75); 8.485(1.82); 7.897(1.18); 7.893(1.01); 7.882(1.01);
7.876(1.29); 7.873(1.05); 7.834(3.4); 7.479(1.35); 7.467(1.36); 7.458(1.31); 7.446(1.19); 6.212(3.64); 4.098(0.51); 4.085(0.53);
3.817(16); 3.579(0.33); 3.411(0.62); 3.396(14.94); 3.375(0.43); 3.321(24.41); 3.175(2.52); 3.162(2.48); 2.671(0.34);
2.506(39.91); 2.501(52.02); 2.497(40.53); 2.328(0.33); 2.18(14.65); 2.09(0.49); 1.99(12); 1.914(0.58); 0(21.58)
Example I-1-024: 1H-NMR(400.0 MHz. $d_6$-DMSO):
δ = 8.57(1.63); 8.564(1.67); 8.53(0.44); 8.524(0.47); 8.504(1.18); 8.5(1.36); 8.492(1.3); 8.489(1.32); 8.047(1.87); 8.041(1.94);
7.911(0.64); 7.908(0.79); 7.905(0.79); 7.901(0.72); 7.891(0.73); 7.887(0.82); 7.885(0.87); 7.881(0.73); 7.483(0.89);
7.47(0.98); 7.463(0.91); 7.45(0.88); 6.348(1.95); 6.342(2); 6.235(2.41); 6.208(0.54); 5.756(16); 3.811(12.36); 3.755(0.58);
3.749(3.73); 3.415(0.65); 3.402(11.54); 3.375(3.56); 3.32(25.51); 2.67(0.4); 2.51(25.65); 2.506(51.18); 2.501(67.9); 2.497
(51.03); 2.328(0.39); 2.269(10.65); 0.008(1.84); 0(44.91); −0.008(2.59)
Example I-1-025: 1H-NMR(400.0 MHz. $d_6$-DMSO):
δ = 8.576(1.94); 8.57(1.98); 8.523(1.38); 8.52(1.48); 8.512(1.45); 8.508(1.44); 8.062(2.36); 7.928(0.83); 7.924(0.99);
7.922(1); 7.918(0.89); 7.908(0.95); 7.904(1.07); 7.901(1.12); 7.898(0.93); 7.609(2.44); 7.5(1.17); 7.488(1.18); 7.48(1.11);
7.468(1.05); 7.136(2.23); 6.276(2.27); 5.756(3.47); 3.666(16); 3.409(14.91); 3.33(47.46); 2.511(11.43); 2.506(22.93);
2.502(30.49); 2.497(22.91); 2.493(11.75); 0.008(0.56); 0(14.89); −0.008(0.68)
Example I-1-026: 1H-NMR(400.0 MHz. $d_6$-DMSO):
δ = 9.182(0.34); 9.159(6.04); 9.134(0.38); 8.585(2.05); 8.579(2.06); 8.515(1.46); 8.512(1.66); 8.504(1.59); 8.5(1.63);
7.933(0.8); 7.929(0.95); 7.926(0.96); 7.922(0.87); 7.912(0.93); 7.908(1.03); 7.906(1.06); 7.902(0.91); 7.49(1.16); 7.478(1.16);
7.47(1.09); 7.458(1.02); 6.37(1.46); 3.818(2.05); 3.755(16); 3.639(1.15); 3.426(0.67); 3.415(14.38); 3.319(35.08); 3.174(0.6);
3.162(0.58); 2.675(0.62); 2.67(0.84); 2.666(0.64); 2.524(2.77); 2.51(52.45); 2.506(107.24); 2.501(143.05); 2.497(105.63);
2.492(52.77); 2.333(0.62); 2.328(0.86); 2.324(0.63); 0.008(1.65); 0(46.68); −0.008(1.76)
Example I-1-027: 1H-NMR(400.0 MHz. $d_6$-DMSO):
δ = 8.568(3.96); 8.562(4.1); 8.503(2.85); 8.491(2.91); 7.909(1.44); 7.904(1.84); 7.899(1.56); 7.888(1.65); 7.883(2.05);
7.879(1.67); 7.733(2.65); 7.522(4.63); 7.484(2.11); 7.472(2.16); 7.464(2.09); 7.452(1.91); 6.264(3.13); 6.219(2.65); 3.855(16);
3.814(12.54); 3.401(21.22); 3.324(62.51); 3.175(0.92); 3.162(0.91); 2.763(1.32); 2.746(2.44); 2.727(1.71); 2.708(1.64);
2.69(2.81); 2.671(2.42); 2.646(1.37); 2.628(2.5); 2.61(2.47); 2.592(2.23); 2.574(1.9); 2.506(53.39); 2.502(69.77);
2.498(51.89); 2.468(1.27); 2.45(0.43); 2.405(0.62); 2.387(1.62); 2.369(2); 2.351(1.24); 2.333(0.65); 0(57.19)
Example I-1-028: 1H-NMR(400.0 MHz. $d_6$-DMSO):
δ = 8.627(5.21); 8.56(3.59); 8.554(2.67); 8.528(0.44); 8.523(0.41); 8.5(2.4); 8.497(2.48); 8.488(2.28); 7.898(1.68); 7.881(1.61);
7.878(1.69); 7.477(1.6); 7.464(1.9); 7.456(1.51); 7.445(1.28); 6.242(3.41); 6.208(0.32); 6.084(5.36); 5.756(0.58);
3.807(16); 3.748(1.56); 3.694(0.38); 3.446(0.51); 3.394(15.21); 3.375(2.46); 3.328(29.27); 3.321(64.19); 2.67(0.66);
2.505(105.11); 2.501(111.87); 2.328(0.64); 1.237(0.38); 0.146(0.32); 0.006(27.04); 0(66.97); −0.15(0.36)
Example I-1-029: 1H-NMR(400.0 MHz. $d_6$-DMSO):
δ = 8.556(0.32); 8.544(2.61); 8.537(276); 8.53(2.16); 8.522(4.8); 8.516(3.81); 7.913(0.88); 7.909(1.09); 7.907(1.09);
7.904(0.95); 7.893(1.03); 7.887(1.19); 7.883(0.95); 7.5(1.33); 7.488(1.33); 7.48(1.24); 7.468(1.12); 7-29(3.16); 7.284(3.14);
6.296(2.49); 3.917(1); 3.899(3.01); 3.881(3.02); 3.863(1); 3.809(0.36); 3.778(16); 3.754(1.13); 3.732(0.37); 3.704(0.66);
3.32(42.95); 3.174(0.68); 3.162(0.68); 2.67(0.62); 2.666(0.47); 2.506(81.79); 2.502(106.33); 2.497(79.85); 2.328(0.62);
1.146(3.44); 1.128(7.54); 1.11(3.52); 0.008(0.9); 0(19.74)
Example I-1-030: 1H-NMR(400.0 MHz. $d_6$-DMSO):
δ = 8.574(2.04); 8.568(2.06); 8.504(1.4); 8.501(1.5); 8.492(1.47); 8.489(1.46); 8.043(2.66); 8.036(2.66); 7.916(0.77);
7.912(0.95); 7.91(0.92); 7.906(0.8); 7.896(0.88); 7.892(1); 7.89(0.99); 7.886(0.8); 7.485(1.09); 7.473(1.08); 7.464(1.02); 7.453
(0.95); 6.414(2.69); 6.408(2.67); 6.234(2.96); 3.815(14.68); 3.404(13.75); 3.32(97.79); 3.008(0.37); 2.991(0.94); 2.974(1.27);
2.956(0.99); 2.939(0.4); 2.675(0.66); 2.67(0.89); 2.666(0.68); 2.506(121.42); 2.501(158.45); 2.497(116.77);
2.332(0.7); 2.328(0.93); 2.324(0.69); 1.252(16); 1.234(15.75); 0.008(0.78); 0(21.82); −0.008(0.96)
Example I-1-031: 1H-NMR(601.6 MHz. $d_6$-DMSO):
δ = 9.506(0.41); 9.465(5.89); 8.589(2.13); 8.586(2.18); 8.514(1.63); 8.512(1.69); 8.506(1.68); 8.504(1.62); 7.931(0.92);
7.929(1.12); 7.927(1.09); 7.925(0.97); 7.918(1.02); 7.915(1.15); 7.914(1.15); 7.911(0.96); 7.486(1.22); 7.485(1.2); 7.478(1.21);
7.472(1.22); 7.471(1.18); 7.464(1.12); 6.43(0.8); 3.85(1.32); 3.818(0.49); 3.781(16); 3.433(0.6); 3.424(14.14); 3.314(1.82);
2.508(4.44); 2.505(8.94); 2.502(12.04); 2.499(9.08); 2.496(4.57)

a) The log P values reported in the tables and preparation examples above were determined in accordance with EEC directive 79/831 Annex V.A8 by HPLC (High Performance Liquid Chromatography) using a reversed-phase column (C18). Temperature 43° C. The calibration is effected with unbranched alkan-2-ones (having 3 to 16 carbon atoms), for which the log P values are known.

The determination of the M+ by LC-MS in the acidic range was carried out at pH 2.7 using the mobile phases 0.1% aqueous formic acid and acetonitrile (contains 0.1% formic acid); linear gradient from 10% acetonitrile to 95% acetonitrile, instrument: Agilent 1100 LC system, Agilent MSD system, HTS PAL.

The determination of the M+ by LC-MS in the neutral range was carried out at pH 7.8 using the mobile phases 0.001 molar aqueous ammonium bicarbonate solution and acetonitrile; linear gradient from 10% acetonitrile to 95% acetonitrile.

The log P values for the acidic range (as log P [a]) and/or for the neutral range (as log P [n]) were stated in the tables and preparation examples above.

b) The determination of the 1H NMR data was effected with a Bruker Avance 400 equipped with a sample flow head (capacity 60 μl), with tetramethylsilane as reference (0.0) and the solvents $CD_3CN$, $CDCl_3$ or $D_6$-DMSO.

The NMR data of selected examples are listed either in conventional form (δ values, multiplet splitting, number of hydrogen atoms) or as NMR peak lists.

NMR Peak List Method

The 1H NMR data of selected examples are stated in the form of 1H NMR peak lists. For each signal peak, first the δ value in ppm and then the signal intensity in round brackets are listed. The δ value—signal intensity number pairs for different signal peaks are listed with separation from one another by semicolons.

The peak list for one example therefore has the form:

$\delta_1$ (intensity$_1$); $\delta_2$ (intensity$_2$); . . . ; $\delta_i$ (intensity$_i$); . . . ; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

Calibration of the chemical shift of $^1$H NMR spectra is accomplished using tetramethylsilane and/or the chemical shift of the solvent, particularly in the case of spectra which are measured in DMSO. Therefore, the tetramethylsilane peak may but need not occur in NMR peak lists.

The lists of the $^1$H NMR peaks are similar to the conventional $^1$H-NMR printouts and thus usually contain all peaks listed in a conventional NMR interpretation.

In addition, like conventional $^1$H NMR printouts, they may show solvent signals, signals of stereoisomers of the target compounds which are likewise provided by the invention, and/or peaks of impurities.

In the reporting of compound signals within the delta range of solvents and/or water, our lists of $^1$H NMR peaks show the standard solvent peaks, for example peaks of DMSO in DMSO-D$_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in this case to identify the reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the peak picking in question in conventional $^1$H NMR interpretation.

Further details of $^1$H NMR peak lists can be found in the Research Disclosure Database Number 564025.

USE EXAMPLES

The examples which follow demonstrate the insecticidal and acaricidal action of the compounds according to the invention. In these examples, the compounds according to the invention cited relate to the compounds listed in Table 1 with the corresponding reference numerals (No.):

*Boophilus microplus*—Injection Test

Solvent: dimethyl sulphoxide

To produce a suitable preparation of active compound, 10 mg of active compound are mixed with 0.5 ml of solvent and the concentrate is diluted with solvent to the desired concentration.

1 µl of the active compound solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 80% at an application rate of 20 µg/animal: I-1-031

*Myzus Persicae*—Oral Test

Solvent: 100 parts by weight of acetone

To produce a suitable preparation of active compound, 1 part by weight of active compound is dissolved using the specified parts by weight of solvent and made up with water until the desired concentration is attained.

50 µl of the active compound preparation are transferred into microtitre plates and made up to a final volume of 200 µl with 150 µl of IPL41 insect medium (33%+15% sugar). Subsequently, the plates are sealed with parafilm, which a mixed population of green peach aphids (*Myzus persicae*) within a second microtitre plate is able to puncture and imbibe the solution through it.

After 5 days, the efficacy in % is determined. 100% means that all the aphids have been killed; 0% means that no aphids have been killed.

In this test, for example, the following compounds from the preparation examples show an efficacy of 100% at an application rate of 20 ppm: I-1-001, I-1-002, I-1-003, I-1-004, I-1-005, I-1-006, I-1-007, I-1-008, I-1-009, I-1-010, I-1-011, I-1-012, I-1-013, I-1-014, I-1-015, I-1-016, I-1-017, I-1-018, I-1-019, I-1-020, I-1-021, I-1-022

*Myzus persicae*—Spray Test

Solvents: 78 parts by weight of acetone 1.5 parts by weight of dimethylformamide Emulsifier: alkylaryl polyglycol ether To produce a suitable active ingredient formulation, 1 part by weight of active ingredient is dissolved with the stated parts by weight of solvent and made up with water containing an emulsifier concentration of 1000 ppm until the desired concentration is attained. To produce further test concentrations, the formulation is diluted with emulsifier-containing water.

Discs of Chinese cabbage leaves (*Brassica pekinensis*) infested by all stages of the green peach aphid (*Myzus persicae*) are sprayed with an active compound formulation of the desired concentration.

After 5-6 days, the efficacy in % is determined. 100% means that all the aphids have been killed; 0% means that no aphids have been killed.

In this test, for example, the following compounds from the preparation examples show an efficacy of 100% at an application rate of 500 g/ha: I-1-004, I-1-006, I-1-007, I-1-008, I-1-009, I-1-010, I-1-011, I-1-013, I-1-017, I-1-018, I-1-019, I-1-020, I-1-021 In this test, for example, the following compounds from the preparation examples show an efficacy of 90% at an application rate of 500 g/ha: I-1-001, I-1-002, I-1-003, I-1-005, I-1-012, I-1-014, I-1-015, I-1-016, I-1-022

*Tetranychus urticae*—Spray Test, OP-Resistant

Solvents: 78.0 parts by weight of acetone 1.5 parts by weight of dimethylformamide Emulsifier: alkylaryl polyglycol ether To produce a suitable preparation of active compound, 1 part by weight of active compound is dissolved using the specified parts by weight of solvent and made up with water containing an emulsifier concentration of 1000 ppm until the desired concentration is attained. To produce further test concentrations, the formulation is diluted with emulsifier-containing water.

Discs of bean leaves (*Phaseolus vulgaris*) infested with all stages of the greenhouse red spider mite (*Tetranychus urticae*) are sprayed with an active compound formulation of the desired concentration.

After 6 days, the efficacy in % is determined. 100% means that all the spider mites have been killed; 0% means that no spider mites have been killed.

In this test, for example, the following compounds from the preparation examples show an efficacy of 90% at an application rate of 500 g/ha: I-1-009, I-1-015.

DEPOSITION EXAMPLES

*Myzus persicae*—Spray Test (MYZUPE)
Solvents: 78.0 parts by weight of acetone
1.5 parts by weight of dimethylformamide
Emulsifier: alkylaryl polyglycol ether To produce a suitable preparation of active compound, 1 part by weight of active compound is dissolved using the specified parts by weight of solvent and made up with water containing an emulsifier concentration of 1000 ppm until the desired concentration is attained. To produce further test concentrations, the formulation is diluted with emulsifier-containing water.

Discs of Chinese cabbage leaves (*Brassica pekinensis*) infested by all stages of the green peach aphid (*Myzus persicae*) are sprayed with an active compound preparation of the desired concentration.

After the desired period of time (dat), the efficacy in % is determined. 100% means that all the aphids have been killed; 0% means that no aphids have been killed.

In this test, for example, the following compounds of the Preparation Examples show superior efficacy to the prior art: see Table 3

*Myzus persicae*—Oral Test (MYZUPE O)
Solvent: 100 parts by weight of acetone

To produce a suitable preparation of active compound, 1 part by weight of active compound is dissolved using the specified parts by weight of solvent and made up with water until the desired concentration is attained.

50 μl of the active compound preparation are transferred into microtitre plates and made up to a final volume of 200 μl with 150 μl of IPL41 insect medium (33%+15% sugar). Subsequently, the plates are sealed with parafilm, which a mixed population of green peach aphids (*Myzus persicae*) within a second microtitre plate is able to puncture and imbibe the solution through it.

After the desired period of time (dat), the efficacy in % is determined. 100% means that all the aphids have been killed; 0% means that no aphids have been killed.

In this test, for example, the following compounds of the Preparation Examples show superior efficacy to the prior art: see Table 3

*Tetranychus urticae*—Spray Test; OP Resistant (TETRUR)
Solvents: 78.0 parts by weight of acetone
1.5 parts by weight of dimethylformamide
Emulsifier: alkylaryl polyglycol ether To produce a suitable preparation of active compound, 1 part by weight of active compound is dissolved using the specified parts by weight of solvent and made up with water containing an emulsifier concentration of 1000 ppm until the desired concentration is attained. To produce further test concentrations, the formulation is diluted with emulsifier-containing water.

Discs of bean leaves (*Phaseolus vulgaris*) which are infested by all stages of the greenhouse red spider mite (*Tetranychus urticae*) are sprayed with an active compound preparation of the desired concentration.

After the desired period of time (dat), the efficacy in % is determined. 100% means that all the spider mites have been killed; 0% means that none of the spider mites have been killed.

In this test, for example, the following compounds of the Preparation Examples show superior efficacy to the prior art: see Table 3

TABLE 3

| Substance | Structure | Animal species | Concentration | % efficacy | dat |
|---|---|---|---|---|---|
| Ex. No. 14 WO2011/009804 prior art | 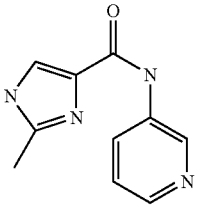 | MYZUPE MYZUPE O  TETRUR | 100 g of ai/ha 4 ppm 0.8 ppm 500 g/ha | 0 0 0 0 | 5/6 dat 5 dat 5 dat 6 dat |
| Ex. No. 13 WO2011/009804 prior art | 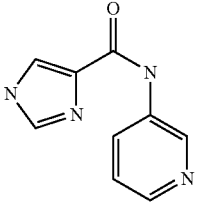 [SMILES: O=C(Nc1cccnc1)c1c[nH]cn1] | MYZUPE MYZUPE O  TETRUR | 100 g of ai/ha 4 ppm 0.8 ppm 500 g/ha | 0 0 0 0 | 6 dat 5 dat 5 dat 6 dat |
| Ex. No. I-1-001 according to the invention | 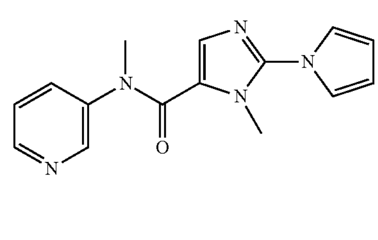 [SMILES: CN(C(=O)c1cnc(-n2cccc2)n1C)c1cccnc1] | MYZUPE MYZUPE O | 100 g of ai/ha 4 ppm 0.8 ppm | 90 100 100 | 6 dat 5 dat 5 dat |

TABLE 3-continued

| Substance | Structure | Animal species | Concentration | % efficacy | dat |
|---|---|---|---|---|---|
| Ex. No. I-1-004 according to the invention | 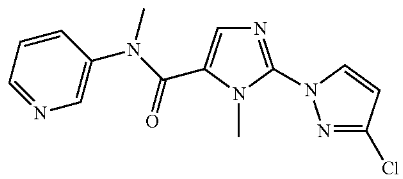 [SMILES: CN(C(=O)c1cnc(-n2ccc(Cl)n2)n1C)c1cccnc1] | MYZUPE<br>MYZUPE O | 100 g of ai/ha<br>4 ppm<br>0.8 ppm | 90<br>100<br>100 | 6 dat<br>5 dat<br>5 dat |
| Ex. No. I-1-006 according to the invention | 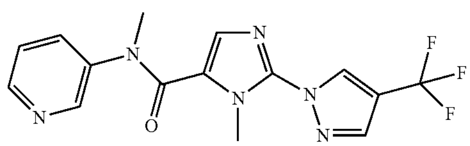 [SMILES: CN(C(=O)c1cnc(-n2cc(C(F)(F)F)cn2)n1C)c1cccnc1] | MYZUPE<br>MYZUPE O | 100 g of ai/ha<br>0.8 ppm | 100<br>100 | 6 dat<br>5 dat |
| Ex. No. I-1-009 according to the invention | 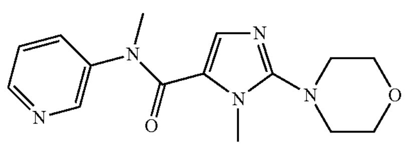 [SMILES: CN(C(=O)c1cnc(N2CCOCC2)n1C)c1cccnc1] | MYZUPE<br>MYZUPE O<br>TETRUR | 100 g of ai/ha<br>0.8 ppm<br>500 g/ha | 70<br>70<br>90 | 6 dat<br>5 dat<br>6 dat |
| Ex. No. I-1-010 according to the invention | 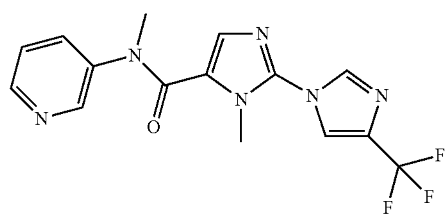 [SMILES: CN(C(=O)c1cnc(-n2cnc(C(F)(F)F)c2)n1C)c1cccnc1] | MYZUPE<br>MYZUPE O | 100 g of ai/ha<br>4 ppm<br>0.8 ppm | 70<br>100<br>100 | 6 dat<br>5 dat<br>5 dat |
| Ex. No. I-1-011 according to the invention | 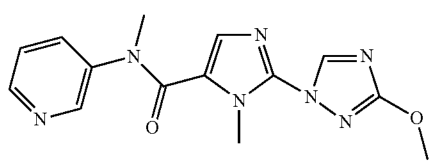 [SMILES: COc1ncn(-c2ncc(C(=O)N(C)c3cccnc3)n2C)n1] | MYZUPE<br>MYZUPE O | 100 g of ai/ha<br>4 ppm<br>0.8 ppm | 70<br>90<br>90 | 5 dat<br>5 dat<br>5 dat |
| Ex. No. I-1-015 according to the invention | 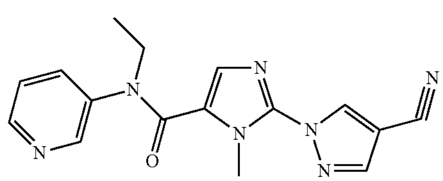 [SMILES: CCN(C(=O)c1cnc(-n2cc(C#N)cn2)n1C)c1cccnc1] | MYZUPE O<br>TETRUR | 4 ppm<br>0.8 ppm<br>500 g/ha | 100<br>100<br>90 | 5 dat<br>5 dat<br>6 dat |
| Ex. No. I-1-017 according to the invention | 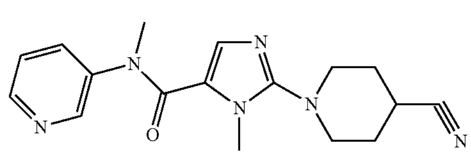 [SMILES: CN(C(=O)c1cnc(N2CCC(C#N)CC2)n1C)c1cccnc1] | MYZUPE<br>MYZUPE O | 100 g of ai/ha<br>4 ppm<br>0.8 ppm | 90<br>100<br>100 | 5 dat<br>5 dat<br>5 dat |

The invention claimed is:
1. Compound of formula (I)

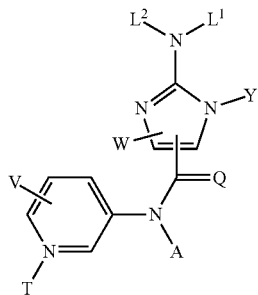

in which
Q represents oxygen or sulphur,
V represents a radical from the group consisting of hydrogen, halogen, alkyl, haloalkyl, alkoxy, haloalkoxy and cyano,
W represents a radical from the group consisting of hydrogen, halogen, alkyl, haloalkyl, alkoxy, haloalkoxy and cyano,
Y represents a radical from the group consisting of hydrogen, cyano, optionally substituted alkyl, alkenyl or alkynyl, optionally substituted cycloalkyl which is optionally interrupted by heteroatoms, optionally substituted cycloalkylalkyl which is optionally interrupted by heteroatoms, arylalkyl or hetarylalkyl,
A represents a radical from the group consisting of hydrogen, optionally substituted alkyl, alkenyl or alkynyl and optionally substituted cycloalkyl or cycloalkylalkyl which are optionally interrupted by heteroatoms,
T represents oxygen or an electron pair,
$L^1$ represents a radical from the group consisting of hydrogen, optionally substituted alkyl, alkenyl, alkynyl, or cycloalkyl and represents the radicals $C(O)R^2$, $C(O)N(R^3)(R^4)$, $C(O)OR^5$ and $SO_2R^6$,
$L^2$ represents a radical from the group consisting of hydrogen, $N(R^{3a})(R^{4a})$, optionally substituted alkyl, alkenyl, alkynyl or alkoxy, optionally substituted cycloalkyl or cycloalkylalkyl which is optionally interrupted by heteroatoms, and optionally substituted aryl, arylalkyl, hetaryl or hetarylalkyl, or
$L^1$ and $L^2$ represent, together with the nitrogen atom to which they are attached, an optionally substituted saturated, partially saturated or aromatic heterocycle having 3 to 7 ring atoms which can optionally be interrupted by further heteroatoms and/or by one or two C=O groups,
$R^2$ represents a radical from the group consisting of hydrogen, optionally substituted alkyl, alkenyl or alkynyl, optionally substituted cycloalkyl, optionally substituted aryl or hetaryl and optionally substituted arylalkyl or hetarylalkyl,
$R^3$ and $R^4$ each independently of one another represent a radical from the group consisting of hydrogen, optionally substituted alkyl, alkenyl or alkynyl, optionally substituted saturated or unsaturated cycloalkyl, cycloalkylalkyl, aryl, hetaryl, arylalkyl or hetarylalkyl, or
$R^3$ and $R^4$ together form an optionally substituted three- to seven-membered aliphatic ring which optionally contains a nitrogen, sulphur or oxygen atom, $R^{3a}$ represents a radical from the group consisting of hydrogen, optionally substituted alkyl, optionally substituted cycloalkyl, aryl, hetaryl, arylalkyl or hetarylalkyl,
$R^{4a}$ represents a radical from the group consisting of hydrogen, optionally substituted alkyl, optionally substituted $C_3$-$C_6$-cycloalkyl and represents the radicals $C(O)R^2$, $C(O)OR^5$ and $SO_2R^6$,
$R^5$ represents optionally substituted alkyl, alkenyl or alkynyl, optionally substituted cycloalkyl or cycloalkylalkyl,
$R^6$ represents a radical from the group consisting of optionally substituted alkyl, alkenyl or alkynyl, optionally substituted cycloalkyl cycloalkylalkyl, aryl, arylalkyl, hetaryl or hetarylalkyl
And/or a salt thereof.
2. Compound according to claim 1 in which
Q represents oxygen or sulphur,
V represents a radical from the group consisting of hydrogen, halogen, $C_1$-$C_4$-alkyl, $C_1$-$C_4$-haloalkyl, $C_1$-$C_4$-alkoxy, $C_1$-$C_4$-haloalkoxy and cyano,
W represents a radical from the group consisting of hydrogen, halogen, $C_1$-$C_4$-alkyl, $C_1$-$C_4$-haloalkyl, $C_1$-$C_4$-alkoxy, $C_1$-$C_4$-haloalkoxy and cyano,
Y represents a radical from the group consisting of hydrogen, $C_1$-$C_6$-alkyl, $C_3$-$C_6$-alkenyl or $C_3$-$C_6$-alkynyl, optionally mono- to polysubstituted independently of one another by halogen, $C_1$-$C_4$-alkoxy, $C_1$-$C_4$-alkyl-S(O)$_n$— or cyano, $C_3$-$C_8$-cycloalkyl, optionally mono- to disubstituted independently of one another by halogen, $C_1$-$C_4$-alkyl, $C_1$-$C_4$-haloalkyl, $C_1$-$C_4$-alkoxy or cyano, straight-chain or branched $C_3$-$C_8$-cycloalkyl-$C_1$-$C_4$-alkyl, optionally interrupted once or twice independently of one another by O, S(O)$_n$, CO or NR$^{4a}$ and optionally mono- to tetrasubstituted independently of one another by halogen, $C_1$-$C_4$-alkyl, $C_1$-$C_4$-haloalkyl, $C_1$-$C_4$-alkoxy or cyano, aryl-$C_1$-$C_4$-alkyl or hetaryl-$C_1$-$C_4$-alkyl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, nitro or cyano,
A represents a radical from the group consisting of hydrogen, $C_1$-$C_6$-alkyl, $C_3$-$C_6$-alkenyl or $C_3$-$C_6$-alkynyl, optionally mono- to polysubstituted independently of one another by halogen, $C_1$-$C_4$-alkoxy, $C_1$-$C_4$-alkyl-S(O)$_n$— or cyano and $C_3$-$C_6$-cycloalkyl, optionally mono- or disubstituted independently of one another by halogen, $C_1$-$C_4$-alkyl, $C_1$-$C_4$-haloalkyl, $C_1$-$C_4$-alkoxy or cyano and $C_1$-$C_6$-alkyl, $C_3$-$C_6$-alkenyl or $C_3$-$C_6$-alkynyl optionally mono- to polysubstituted independently of one another by halogen, $C_1$-$C_4$-alkoxy, $C_1$-$C_4$-alkyl-S(O)$_n$- or cyano and straight-chain or branched $C_3$-$C_8$-cycloalkyl-$C_1$-$C_4$-alkyl, optionally mono- to disubstituted independently of one another by halogen, $C_1$-$C_4$-alkyl, $C_1$-$C_4$-haloalkyl, $C_1$-$C_4$-alkoxy or cyano,
T represents oxygen or an electron pair,
$L^1$ represents a radical from the group consisting of hydrogen, $C_1$-$C_4$-alkyl, $C_3$-$C_6$-alkenyl or $C_3$-$C_6$-alkynyl, optionally mono- to trisubstituted independently of one another by halogen, $C_1$-$C_4$-alkoxy, $C_1$-$C_4$-alkyl-S(O)$_n$— or cyano, $C_3$-$C_6$-cycloalkyl, optionally mono- to disubstituted independently of one another by halogen, $C_1$-$C_4$-alkyl, $C_1$-$C_4$-haloalkyl, $C_1$-$C_4$-alkoxy, or cyano and represents the radicals $C(O)R^2$, $C(O)N(R^3)(R^4)$, $C(O)OR^5$ and $SO_2R^6$, $L^2$ represents a radical from the group consisting of hydrogen, —N(R$^{3a}$)(R$^{4a}$), $C_1$-$C_4$-alkyl, $C_3$-$C_6$-alkenyl, $C_3$-$C_6$-alkynyl or $C_1$-$C_4$-alkoxy, optionally mono- to trisubstituted independently of one another by halogen, $C_1$-$C_4$-alkoxy, $C_1$-$C_4$-alkyl-S(O)$_n$— or cyano, straight-chain or branched $C_3$-$C_8$-cycloalkyl or $C_3$-$C_8$-cycloalkyl-$C_1$-$C_4$-alkyl, optionally interrupted once or twice independently of one another by O, S(O)$_n$, CO or NR$^{4a}$ and optionally mono- to tetrasubstituted independently of one another by halogen, $C_1$-$C_4$-alkyl, $C_1$-$C_4$-haloalkyl, $C_1$-$C_4$-alkoxy or cyano, aryl, hetaryl, arylalkyl or hetarylalkyl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, nitro or cyano, or $L^1$ and $L^2$ together with N represent a heterocycle from the group U-1 to U-36,

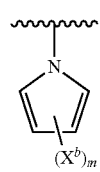

U-1

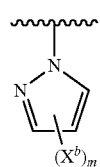

U-2

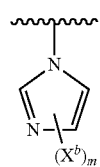

U-3

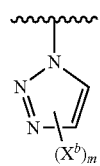

U-4

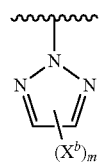

U-5

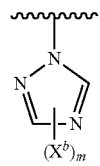

U-6

-continued

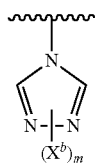

U-7

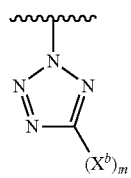

U-8

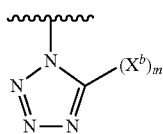

U-9

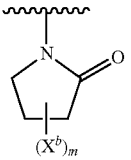

U-10

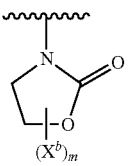

U-11

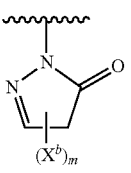

U-12

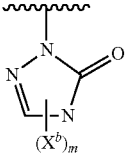

U-13

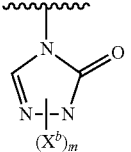

U-14

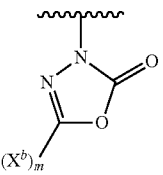

U-15

| | |
|---|---|
| U-16 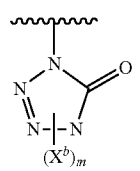 | U-25 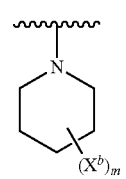 |
| U-17 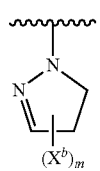 | U-26 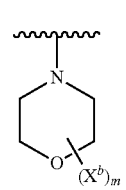 |
| U-18 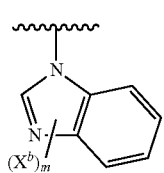 | U-27 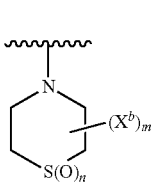 |
| U-19 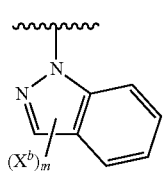 | U-28 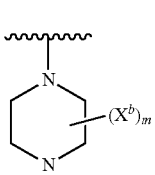 |
| U-20 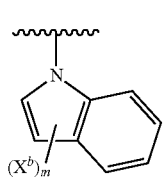 | U-29 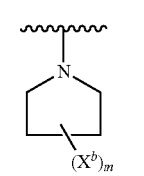 |
| U-21 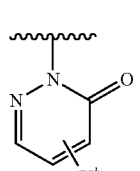 | U-30 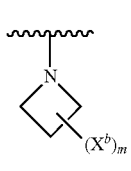 |
| U-22 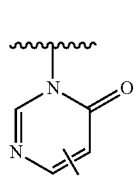 | U-31 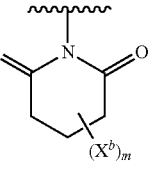 |
| U-23 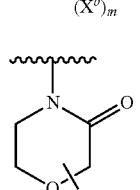 | U-32 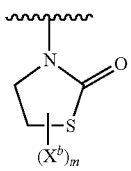 |
| U-24 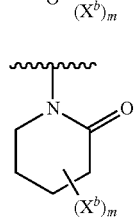 | U-33 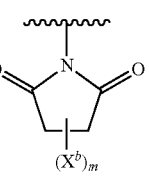 |

-continued

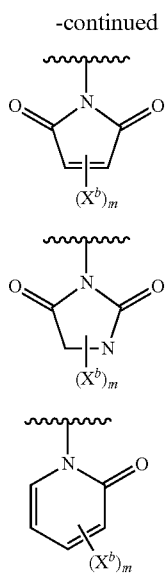

U-34

U-35

U-36

$X_b$ represents a radical from the group consisting of halogen, nitro, cyano, amino, C1-C4-alkyl, C3-C6-cycloalkyl, C1-C5-haloalkyl, C1-C4-alkoxy, C1-C4-haloalkoxy, C3-C6-halocycloalkyl, C1-C4-alkoxy-C1-C4-alkyl, cyano-C1-C4-alkyl, C3-C6-cycloalkyl-C1-C4-alkyl, C2-C6-alkenyl, C3-C6-alkynyl, C1-C4-alkyl-S(O)n—, C1-C4-alkylcarbonyl, C1-C6-haloalkylcarbonyl, C1-C6-alkoxycarbonyl, C1-C6-alkylaminocarbonyl, di-(C1-C6)alkylaminocarbonyl, C1-C6-alkylcarbonylamino, aryl and hetaryl, where the substituents aryl and hetaryl may optionally be mono- or polysubstituted by identical or different substituents from the group consisting of halogen, cyano, nitro, C1-C6-alkyl, C2-C6-alkenyl, C2-C6-alkynyl, C1-C4-alkoxy, C1-C4-haloalkyl, C1-C6-haloalkoxy and C1-C4-alkylthio and where the ring nitrogen atoms in U-13, U-14, U-16 and U-28 are not substituted by halogen, nitro, cyano, C1-C4-alkoxy, C1-C4-haloalkoxy, C1-C4-alkoxy-C1-C4-alkyloxy, or $X^b$ represents a C2-C5-carbon chain which optionally contains 1 heteroatom from the group consisting of N, S and O, which is attached at two adjacent ring positions and which forms an aliphatic, aromatic, heteroaromatic or heterocyclic ring, in which case m equals 2

$R^2$ represents a radical from the group consisting of hydrogen, $C_1$-$C_8$-alkyl, $C_3$-$C_8$-alkenyl or $C_3$-$C_8$-alkynyl, optionally mono- to polysubstituted independently of one another by halogen, $C_1$-$C_4$-alkoxy or $C_1$-$C_4$-alkyl-S(O)$_n$—, $C_3$-$C_8$-cycloalkyl, optionally mono- to disubstituted independently of one another by halogen, $C_1$-$C_4$-alkyl, $C_1$-$C_4$-haloalkyl, $C_1$-$C_4$-alkoxy or cyano, aryl or hetaryl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, nitro or cyano and straight-chain or branched aryl-$C_1$-$C_4$-alkyl or hetaryl-$C_1$-$C_4$-alkyl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, nitro or cyano, $R^3$, $R^4$ independently of one another represent a radical from the group consisting of hydrogen, $C_1$-$C_8$-alkyl, $C_3$-$C_8$-alkenyl or $C_3$-$C_8$-alkynyl, optionally mono- to polysubstituted independently of one another by halogen, $C_1$-$C_4$-alkoxy or $C_1$-$C_4$-alkyl-S(O)$_n$—, $C_3$-$C_8$-cycloalkyl, optionally mono- to disubstituted independently of one another by halogen, $C_1$-$C_4$-alkyl, $C_1$-$C_4$-haloalkyl, $C_1$-$C_4$-alkoxy or cyano, aryl or hetaryl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, nitro or cyano and straight-chain or branched aryl-$C_{1-C_4}$-alkyl or hetaryl-$C_1$-$C_4$-alkyl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, nitro or cyano, $R^{3a}$ represents a radical from the group consisting of hydrogen, $C_1$-$C_8$-alkyl, optionally mono- to polysubstituted independently of one another by halogen, cyano or $C_1$-$C_4$-alkoxy, $C_3$-$C_8$-cycloalkyl, optionally mono- to disubstituted independently of one another by halogen, $C_1$-$C_4$-alkyl, $C_1$-$C_4$-haloalkyl or $C_1$-$C_4$-alkoxy, aryl or hetaryl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, nitro or cyano and straight-chain or branched aryl-$C_1$-$C_4$-alkyl or hetaryl-$C_1$-$C_4$-alkyl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, nitro or cyano, $R^{4a}$ represents a radical from the group consisting of hydrogen, $C_1$-$C_4$-alkyl, optionally mono- to polysubstituted independently of one another by halogen or $C_1$-$C_4$-alkoxy, $C_3$-$C_6$-cycloalkyl, optionally mono- to disubstituted independently of one another by halogen, $C_1$-$C_4$-alkyl, $C_1$-$C_4$-haloalkyl or $C_1$-$C_4$-alkoxy and represents the radicals C(O)$R^2$, C(O)$R^5$ and SO$_2R^6$, $R^5$ represents $C_1$-$C_8$-alkyl, $C_3$-$C_8$-alkenyl or $C_3$-$C_8$-alkynyl, optionally mono- to polysubstituted independently of one another by halogen, $C_1$-$C_4$-alkoxy or $C_1$-$C_4$-alkyl-S(O)$_n$—, $C_3$-$C_8$-cycloalkyl, optionally mono- to disubstituted independently of one another by halogen, $C_1$-$C_4$-alkyl, $C_1$-$C_4$-haloalkyl, $C_1$-$C_4$-alkoxy or cyano, $R^6$ represents a radical from the group consisting of $C_1$-$C_8$-alkyl, $C_3$-$C_8$-alkenyl or $C_3$-$C_8$-alkynyl, optionally mono- to polysubstituted independently of one another by halogen, $C_1$-$C_4$-alkoxy or $C_1$-$C_4$-alkyl-S(O)$_n$—, $C_3$-$C_8$-cycloalkyl, optionally mono- to disubstituted independently of one another by halogen, $C_1$-$C_4$-alkyl, $C_1$-$C_4$-haloalkyl, $C_1C_4$-alkoxy or cyano, aryl or hetaryl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, nitro or cyano, m represents a number 0, 1, 2 or 3, n represents a number 0, 1 or 2, and/or a salt thereof.

3. Compound according to claim 2 in which

Q represents oxygen,

V represents a radical from the group consisting of hydrogen, fluorine, chlorine, bromine, methyl and ethyl, W represents a radical from the group consisting of hydrogen, fluorine, chlorine, bromine, cyano and methyl, Y represents a radical from the group consisting of hydrogen, $C_1$-$C_4$-alkyl, $C_3$-$C_4$-alkenyl or $C_3$-$C_4$-alkynyl, optionally mono- to pentasubstituted independently of one another by fluorine, chlorine, bromine, methoxy or ethoxy, and $C_3$-$C_6$-cycloalkyl, optionally mono- to disubstituted independently of one another by fluorine, chlorine, bromine, methyl, ethyl, trifluoromethyl, methoxy, ethoxy or cyano, A represents a radical from the group consisting of hydrogen, $C_1$-$C_6$-alkyl, $C_3$-$C_6$-alkenyl or $C_3$-$C_6$-alkynyl, optionally mono- to pentasubstituted independently of one another by fluorine, chlorine, bromine, methoxy, ethoxy or cyano, and $C_3$-$C_6$-cycloalkyl, optionally mono- to disubstituted independently of one another by fluorine, chlorine, bromine, methyl, ethyl, trifluoromethyl, methoxy, ethoxy or cyano, T represents an electron pair, $L^1$ and $L^2$ represent, together with N, a heterocycle from the group U-1, U-2, U-3, U-4, U-5, U-6, U-7, U-25, U-26, U-27, U-28, U-29 and U-30, $X^b$ represents a radical from the group consisting of halogen, nitro, cyano, amino, $C_1$-$C_4$-alkyl, $C_3$-$C_6$-cycloalkyl, $C_1$-$C_2$-haloalkyl, $C_1$-$C_4$-alkoxy, $C_1$-$C_4$-haloalkoxy, $C_3$-$C_6$-halocycloalkyl, $C_1$-$C_4$-alkoxy-$C_1$-$C_4$-alkyl, $C_1$-$C_6$-alkylthio, $C_1$-$C_4$-alkoxycarbonyl, $C_1$-$C_4$-alkylaminocarbonyl, $C_1$-$C_6$-alkylsulphonyl, $C_1$-$C_6$-alkylcarbonylamino and phenyl, where phenyl may optionally be mono- to trisubstituted by fluorine, chlorine, bromine, methyl, ethyl, difluoromethyl, trifluoromethyl, methoxy, ethoxy, Me-S(O)$_n$—, Et-S(O)$_n$—, difluoromethoxy, trifluoromethoxy, trifluoromethyl-S(O)$_n$—, difluoroethyl-S(O)$_n$—, trifluoroethyl-S(O)$_n$—, nitro or cyano, or $X^b$ represents a $C_3$-$C_5$-carbon chain, which is attached to two adjacent ring positions and forms an aliphatic ring, in which case m is equal to 2, m represents a number 0, 1 or 2, n represents a number 0, 1 or 2, and/or a salt thereof.

4. Compound according to claim 2 of the formula (I-1)

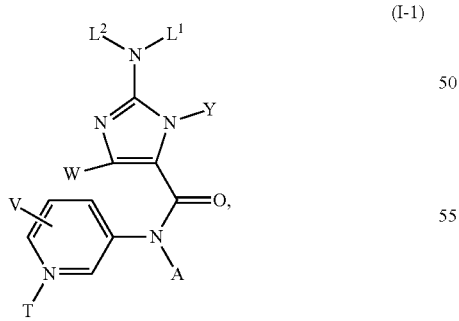

(I-1)

where

V represents a radical from the group consisting of hydrogen, fluorine, chlorine, methyl and cyano, W represents a radical from the group consisting of hydrogen, fluorine, chlorine, bromine and methyl, Y represents a radical from the group consisting of methyl, ethyl, propyl, allyl or propargyl, optionally mono- to trisubstituted independently of one another by fluorine, methoxy, ethoxy or cyano, A represents a radical from the group consisting of hydrogen; methyl, ethyl, propyl, allyl, propargyl or cyclopropyl, optionally mono- to trisubstituted independently of one another by fluorine, methoxy, ethoxy or cyano, T represents an electron pair, $L^1$ and $L^2$ represent, together with N, a heterocycle from the group U-1, U-2, U-3, U-4, U-5, U-6, U-7, U-25, U-26, U-27, U-29 and U-30, $X^b$ represents a radical from the group consisting of fluorine, chlorine, bromine, cyano, amino, methyl, ethyl, n- and isopropyl, cyclopropyl, trifluoromethyl, difluoromethyl, trifluoroethyl, methoxy, ethoxy, n- and isopropoxy, trifluoromethoxy, methoxymethyl, ethoxymethyl, methoxyethyl, ethoxyethyl, methyl-S(O)$_n$—, ethyl-S(O)$_n$—, methoxycarbonyl, ethoxycarbonyl, methylaminocarbonyl, methylcarbonylamino or phenyl, where phenyl may optionally be mono- to trisubstituted by fluorine, chlorine, bromine, methyl, ethyl, difluoromethyl, trifluoromethyl, methoxy, ethoxy, nitro or cyano, or $X^b$ represents a $C_3$-$C_4$-carbon chain, which is attached to two adjacent ring positions and forms an aliphatic ring, in which case m is equal to 2, m represents a number 0, 1 or 2, n represents a number 0, 1 or 2, and/or a salt thereof.

5. Compound according to claim 4 in which

V represents hydrogen,

W represents hydrogen,

Y represents a radical from the group consisting of hydrogen, methyl, ethyl, allyl and propargyl, A represents a radical from the group consisting of hydrogen, methyl, ethyl and cyclopropyl, T represents an electron pair, $L^1$ and $L^2$ represent, together with N, a heterocycle from the group U-1, U-2, U-3, U-6, U-25, U-26 and U-29, $X^b$ represents a radical from the group consisting of fluorine, chlorine, bromine, cyano, amino, methyl, ethyl, n- and isopropyl, trifluoromethyl, methoxy, ethoxy, methylthio and phenyl, where phenyl may optionally be mono- to trisubstituted by fluorine, chlorine, methyl or methoxy, or $X^b$ represents a $C_3$-$C_4$-carbon chain, which is attached to two adjacent ring positions and forms an aliphatic ring, in which case m is equal to 2, m represents a number 0, 1 or 2, and/or a salt thereof.

6. Compound according to claim 4 in which

V represents hydrogen,

W represents hydrogen,

Y represents methyl,

A represents methyl, ethyl or cyclopropyl,

T represents an electron pair, $L^1$ and $L^2$ represent, together with N, a heterocycle from the group consisting of U-1, U-2, U-3, U-6, U-25, U-26 and U-29, X$^b$ represents a radical from the group consisting of chlorine, cyano, amino, methyl, isopropyl, trifluoromethyl, methylthio and phenyl, or X$^b$ represents —(CH$_2$)$_3$—, which is attached to two adjacent ring positions and forms an aliphatic ring, in which case m is equal to 2, m represents a number 0, 1 or 2, and/or a salt thereof.

7. Composition, comprising at least one compound and/or salt according to claim 1 and one or more customary extenders and/or surfactants optionally for controlling animal pests.

8. Method for controlling animal pests, comprising allowing at least one compound and/or salt according to claim 1 or a composition thereof to act on the animal pests and/or a habitat thereof.

9. A product comprising at least one compound and/or salt according to claim 1 or a composition thereof for controlling animal pests.

10. Method according to claim 8, where surgical, therapeutic and diagnostic treatment of a human or animal body is excluded.

11. A product comprising at least one compound and/or salt according to claim 1 for protecting propagation material of one or more plants.

12. Agrochemical formulation comprising at least one compound and/or salt according to claim 1 in a biologically effective amount of from 0.00000001 to 98% by weight based on the weight of the agrochemical formulation, and one or more extenders and/or surfactants.

13. Agrochemical formulation according to claim 12, additionally comprising a further agrochemically active compound.

14. Intermediate of formula (VI)

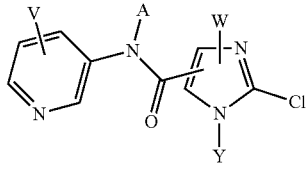

(VI)

Wherein

Q represents oxygen or sulphur,

V represents a radical from the group consisting of hydrogen, halogen, alkyl, haloalkyl, alkoxy, haloalkoxy and cyano, W represents a radical from the group consisting of hydrogen, halogen, alkyl, haloalkyl, alkoxy, haloalkoxy and cyano, Y represents a radical from the group consisting of hydrogen, cyano, optionally substituted alkyl, alkenyl or alkynyl, optionally substituted cycloalkyl which is optionally interrupted by heteroatoms, optionally substituted cycloalkylalkyl which is optionally interrupted by heteroatoms, arylalkyl or hetarylalkyl, A represents a radical from the group consisting of hydrogen, optionally substituted alkyl, alkenyl or alkynyl and optionally substituted cycloalkyl or cycloalkylalkyl which are optionally interrupted by heteroatoms, T represents oxygen or an electron pair, L$^1$ represents a radical from the group consisting of hydrogen, optionally substituted alkyl, alkenyl, alkynyl, or cycloalkyl and represents the radicals C(O)R$^2$, C(O)N(R$^3$)(R$^4$), C(O)OR$^5$ and SO$_2$R$^6$, L$^2$ represents a radical from the group consisting of hydrogen, N(R$^{3a}$)(R$^{4a}$), optionally substituted alkyl, alkenyl, alkynyl or alkoxy, optionally substituted cycloalkyl or cycloalkylalkyl which is optionally interrupted by heteroatoms, and optionally substituted aryl, arylalkyl, hetaryl or hetarylalkyl, or L$^1$ and L$^2$ represent, together with the nitrogen atom to which they are attached, an optionally substituted saturated, partially saturated or aromatic heterocycle having 3 to 7 ring atoms which can optionally be interrupted by further heteroatoms and/or by one or two C=O groups, R$^2$ represents a radical from the group consisting of hydrogen, optionally substituted alkyl, alkenyl or alkynyl, optionally substituted cycloalkyl, optionally substituted aryl or hetaryl and optionally substituted arylalkyl or hetarylalkyl, R$^3$ and R$^4$ each independently of one another represent a radical from the group consisting of hydrogen, optionally substituted alkyl, alkenyl or alkynyl, optionally substituted saturated or unsaturated cycloalkyl, cycloalkylalkyl, aryl, hetaryl, arylalkyl or hetarylalkyl, or R$^3$ and R$^4$ together form an optionally substituted three- to seven-membered aliphatic ring which optionally contains a nitrogen, sulphur or oxygen atom, R$^{3a}$ represents a radical from the group consisting of hydrogen, optionally substituted alkyl, optionally substituted cycloalkyl, aryl, hetaryl, arylalkyl or hetarylalkyl, R$^{4a}$ represents a radical from the group consisting of hydrogen, optionally substituted alkyl, optionally substituted C$_3$-C$_6$-cycloalkyl and represents the radicals C(O)R$^2$, C(O)OR$^5$ and SO$_2$R$^6$, R$^5$ represents optionally substituted alkyl, alkenyl or alkynyl, optionally substituted cycloalkyl or cycloalkylalkyl, R$^6$ represents a radical from the group consisting of optionally substituted alkyl, alkenyl or alkynyl, optionally substituted cycloalkyl cycloalkylalkyl, aryl, arylalkyl, hetaryl or hetarylalkyl and/or a salt thereof.

* * * * *